United States Patent
Aebi et al.

(10) Patent No.: US 8,063,042 B2
(45) Date of Patent: Nov. 22, 2011

(54) HETEROCYCLIC COMPOUNDS

(75) Inventors: Johannes Aebi, Binningen (CH); Alfred Binggeli, Binningen (CH); Luke Green, Basel (CH); Guido Hartmann, Loerrach (DE); Hans P. Maerki, Basel (CH); Patrizio Mattei, Riehen (CH); Fabienne Ricklin, Hombourg (FR)

(73) Assignee: Hoffmann-La Roche Inc., Nutley, NJ (US)

( * ) Notice: Subject to any disclaimer, the term of this patent is extended or adjusted under 35 U.S.C. 154(b) by 253 days.

(21) Appl. No.: 12/170,495

(22) Filed: Jul. 10, 2008

(65) Prior Publication Data

US 2009/0023713 A1 Jan. 22, 2009

(30) Foreign Application Priority Data

Jul. 19, 2007 (EP) .................................. 07112766

(51) Int. Cl.
*A61K 31/54* (2006.01)
*A61K 31/496* (2006.01)
*C07D 401/06* (2006.01)
*C07D 403/06* (2006.01)
*C07D 211/74* (2006.01)

(52) U.S. Cl. ........... 514/222.5; 514/253.01; 514/254.02; 544/8; 544/230; 544/360; 544/372; 546/16

(58) Field of Classification Search ................. None
See application file for complete search history.

(56) References Cited

U.S. PATENT DOCUMENTS

| 3,331,830 A | 7/1967 | Tomcufcik et al. |
| 3,634,411 A | 1/1972 | Fauran et al. |
| 2003/0144277 A1 | 7/2003 | Delucca |
| 2004/0102450 A1* | 5/2004 | Ewing et al. ............. 514/252.13 |
| 2007/0167470 A1 | 7/2007 | Chen |

FOREIGN PATENT DOCUMENTS

GB 2163153 2/1986

OTHER PUBLICATIONS

Wolff, Manfred E. Burger's Medicinal Chemistry, 5th Ed. Part 1, pp. 975-977 (1995).*
Banker et al. "Modern Pharmaceutics", 3rd Ed. p. 596 (1996).*
Guo, Z et al *Tetrahedron Asymmetry*, 17 (2006) 2015-2020 XP0025168176.
Seebach D et al *Helvetica Chimica Acta*, 70 (1987) 1605-1615 XP002516818.
Vice, S et al *Jour. of Organic Chem.* 66:7 (2001) 2487-2492 XP002516941.
Cao, J. et al. *J. Med. Chem.*. 47 (2004) 6128-6136.

* cited by examiner

*Primary Examiner* — Emily Bernhardt
(74) *Attorney, Agent, or Firm* — George W. Johnston; Patricia S. Rocha-Tramaloni

(57) ABSTRACT

The invention is concerned with novel heterocyclyl compounds of formula (I)

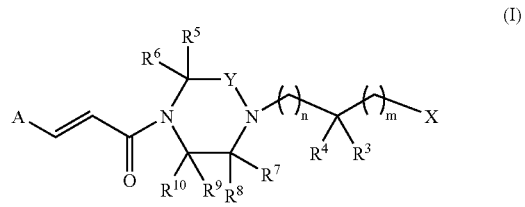

wherein A, X, Y, $R^3$, $R^4$, $R^5$, $R^6$, $R^7$, $R^8$, $R^9$, $R^{10}$, m and n are as herein defined, as well as physiologically acceptable salts thereof. These compounds are antagonists of CCR2 receptor, CCR5 receptor and/or CCR3 receptor and can be used as medicaments.

17 Claims, No Drawings

HETEROCYCLIC COMPOUNDS

PRIORITY TO RELATED APPLICATION(S)

This application claims the benefit of European Patent Application No. 07112766.6 filed Jul. 19, 2007, which is hereby incorporated by reference in its entirety.

SUMMARY OF THE INVENTION

The invention is concerned with novel heterocyclyl compounds of formula (I)

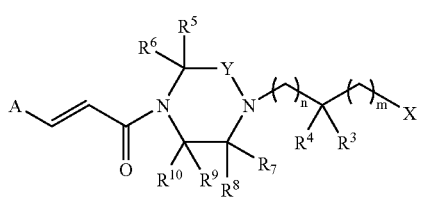

wherein A, X, Y, $R^3$, $R^4$, $R^5$, $R^6$, $R^7$, $R^8$, $R^9$, $R^{10}$, m and n are described herein.

BACKGROUND OF THE INVENTION

The compounds of formula (I) are CCR2 receptor (Chemokine Receptor 2/Monocyte chemotactic protein 1 receptor) antagonists and also CCR5 receptor (Chemokine Receptor 5) and/or CCR3 receptor (Chemokine Receptor 3) antagonists. Chemokines are a family of small, secreted proinflammatory cytokines functioning as chemoattractants for leukocytes. They promote trafficking of leukocytes from vascular beds into surrounding tissues in response to inflammatory signals. Chemotaxis starts upon chemokine binding to receptors (GPCRs) by initiating signaling pathways involving increased Ca-flux, inhibition of cAMP production, rearrangements of the cytoskeleton, activation of integrins and of cell motility processes and an increase in the expression of adhesion proteins.

Proinflammatory chemokines are considered to be involved in the development of atherosclerosis and other important diseases with inflammatory components like rheumatoid arthritis, asthma, multiple sclerosis, transplant rejection and ischemia reperfusion injury with specific prominent effects in nephropathy and peripheral vascular diseases. Monocyte Chemotactic protein 1 is considered to be the major stimulated chemokine mediating inflammatory processes in these diseases through the CCR2 receptor on monocytes and on some T lymphocytes. In addition MCP-1/CCR2 are in discussion to be related to the progression of the metabolic syndrome to more severe stages of obese and diabetic diseases.

CCR2 has also been linked to HIV infection, and consequently the course of autoimmune diseases, through its heterodimerization with CCR5 which has a role as coreceptor for viral entry into host cells.

Thus, CCR2 can be a target of a new medicine for treatment of peripheral vascular diseases, and more specifically for treatment of patients with critical limb ischemia. Furthermore, study results and experiences from the development of a new CCR2 medicine for this indication may facilitate a follow-up development for treatment of atherosclerosis. There is a large body of information from animal models of MCP-1 and CCR2 ko mice in wt or apoE–/– or LDL-R–/– backgrounds showing that the MCP-1/CCR2 pathway is essential for monocyte/macrophage recruitment, and also for intimal hyperplasia and the formation and stability of atherosclerotic lesions. In addition, numerous reports describe involvement of the MCP-1/CCR2 pathway in man post injury and in various inflammatory processes, including such in vascular beds.

DETAILED DESCRIPTION OF THE INVENTION

The invention is concerned with novel heterocyclyl compounds of formula (I),

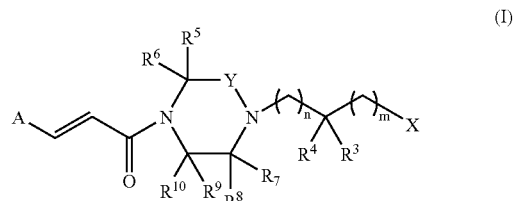

wherein
A is aryl or heteroaryl, said aryl and said heteroaryl being optionally substituted by one to three substituents independently selected from the group consisting of halogen, benzyloxy, heteroaryl-$C_{1-6}$ alkoxy, $C_{1-6}$ alkyl, $C_{1-6}$ alkoxy and halo $C_{1-6}$ alkoxy, or said aryl and said heteroaryl being optionally substituted by $C_{1-6}$ alkylenedioxy,
X is —N($R^1$)($R^2$) or —N$^+$($R^1$)($R^2$)($R^{11}$);
with (a) $R^1$ and $R^2$ independently selected from hydrogen, $C_{1-6}$ alkyl, $C_{3-6}$ alkenyl, $C_{3-6}$ alkynyl, hydroxy $C_{2-6}$ alkyl, $C_{1-6}$ alkoxy $C_{2-6}$ alkyl, $C_{3-7}$ cycloalkyl, $C_{3-7}$ cycloalkyl $C_{1-6}$alkyl, $C_{7-10}$ bicycloalkyl, phenyl $C_{1-3}$ alkyl, heteroaryl $C_{1-3}$ alkyl, heterocyclyl or heterocyclyl $C_{1-6}$ alkyl, in which the cycloalkyl of said $C_{3-7}$ cycloalkyl and said $C_{3-7}$ cycloalkyl $C_{1-6}$ alkyl, the phenyl of said phenyl $C_{1-3}$ alkyl, the heteroaryl of said heteroaryl $C_{1-3}$ alkyl and the heterocyclyl of said heterocyclyl and said heterocyclyl $C_{1-6}$ alkyl are optionally substituted by one to three substituents independently selected from the group consisting of $R^d$; or
(b) $R^1$ and $R^2$, together with the nitrogen atom to which they are attached, form a heterocyclyl optionally substituted by one to three substituents independently selected from the group consisting of $R^d$, and one of the ring carbon atoms of said heterocyclyl formed by $R^1$ and $R^2$ being optionally replaced with a carbonyl group; and/or one of the ring carbon atoms of the heterocyclyl formed by $R^1$ and $R^2$ may be a ring carbon atom of another ring which is $C_{3-7}$ cycloalkyl or heterocyclyl, one or two ring carbon atoms of said another ring being optionally replaced by a carbonyl group, and said another ring being optionally substituted by $C_{1-6}$ alkyl;
$R^3$ and $R^4$ are, independently hydrogen, hydroxy, $C_{1-6}$ alkyl, $C_{1-6}$ alkoxy, $C_{3-7}$ cycloalkyl, $C_{3-7}$ cycloalkyl $C_{1-6}$ alkyl, $C_{1-6}$ alkoxycarbonyl, carboxyl, carbamoyl, mono or di-$C_{1-6}$ alkyl substituted carbamoyl, $C_{1-6}$ alkoxycarbonyloxy, mono or di-$C_{1-6}$ alkyl substituted aminocarbonyloxy, hydroxy-$C_{1-6}$ alkyl, $C_{1-6}$ alkoxy-$C_{1-6}$ alkyl, halogen or halo $C_{1-6}$ alkyl; or
$R^3$ and $R^4$, together with the carbon atom to which they are attached, form $C_{3-7}$ cycloalkyl or heterocyclyl optionally substituted by one to three substituents independently selected from the group consisting of $C_{1-4}$ alkyl, halo $C_{1-4}$ alkyl and halogen;

Y is C(O) or S(O)$_2$;

R$^5$ and R$^6$ are independently hydrogen, C$_{1-6}$ alkyl or C$_{3-7}$ cycloalkyl, said C$_{1-6}$ alkyl and said C$_{3-7}$ cycloalkyl being optionally substituted by one to three substituents independently selected from the group consisting of amino, hydroxy, carboxyl, carbamoyl, mono or di-C$_{1-6}$ alkyl substituted carbamoyl and C$_{1-6}$ alkoxycarbonyl; or R$^5$ and R$^6$, together with the carbon atom to which they are attached, form C$_{3-7}$ cycloalkyl or heterocyclyl;

R$^7$, R$^8$, R$^9$ and R$^{10}$ are independently hydrogen, C$_{1-6}$ alkyl or C$_{3-7}$ cycloalkyl, said C$_{1-6}$ alkyl being optionally substituted by one to three substituents independently selected from the group consisting of hydroxy, C$_{1-6}$ alkoxy, carboxyl, carbamoyl, mono or di-C$_{1-6}$ alkyl substituted carbamoyl and C$_{1-6}$ alkoxycarbonyl, aryl and heteroaryl, in which said aryl and said heteroaryl are optionally substituted by one to three substituents independently selected from the group consisting of halogen, C$_{1-6}$ alkyl, halo C$_{1-6}$ alkyl, C$_{1-6}$ alkoxy and halo C$_{1-6}$ alkoxy;

R$^{11}$ is C$_{1-6}$alkyl;

R$^d$ is hydroxy, cyano, NR$^a$R$^b$, halogen, C$_{1-6}$ alkyl, halo C$_{1-4}$ alkyl, hydroxy C$_{1-6}$ alkyl, C$_{1-6}$ alkoxy, C$_{1-6}$ alkoxy C$_{1-6}$ alkyl, C$_{3-7}$ cycloalkyl, C$_{1-6}$ alkoxycarbonyl, acyl, —C(O)NR$^a$R$^b$, —NR$^a$—C(O)—R$^b$, —NR$^a$—C(O)—OR$^b$, —NR$^a$—C(O)—NR$^b$, —NR$^a$—SO$_2$—R$^b$, —NR$^a$—SO$_2$—NR$^b$R$^c$, —OC(O)NR$^a$R$^b$, —OC(O)OR$^a$, C$_{1-6}$ alkylsulfonyl, C$_{1-6}$ alkylsulfinyl, C$_{1-4}$ alkylthio, phenyl, phenyl C$_{1-3}$ alkyl, heteroaryl, heteroaryl C$_{1-3}$ alkyl or heterocyclyl, and the phenyl of said phenyl and said phenyl C$_{1-3}$ alkyl, the heteroaryl of said heteroaryl and said heteroaryl C$_{1-3}$ alkyl, and the heterocyclyl being optionally substituted by one to three substituents independently selected from the group consisting of hydroxy, cyano, NR$^a$R$^b$, halogen, C$_{1-6}$ alkyl, halo C$_{1-6}$ alkyl, hydroxy C$_{1-6}$ alkyl, C$_{1-6}$ alkoxycarbonyl, acyl, —C(O)NR$^a$R$^b$, —NR$^a$—C(O)—R$^b$, —NR$^a$—C(O)—OR$^b$, —NR$^a$—C(O)—NR$^b$, —NR$^a$—SO$_2$—R$^b$, —NR$^a$SO$_2$—NR$^b$R$^c$, —OC(O)NR$^a$R$^b$, —OC(O)OR$^a$, C$_{1-6}$ alkylsulfonyl, C$_{1-6}$ alkylsulfinyl and C$_{1-6}$ alkylthio, and one or two ring carbon atoms of the heterocyclyl being optionally replaced with a carbonyl group;

R$^a$, R$^b$ and R$^c$ are independently hydrogen or C$_{1-6}$ alkyl;

n is an integer of 0 to 3;

m is an integer of 0 to 3;

m+n is an integer of 1 to 5;

or prodrugs or pharmaceutically acceptable salts thereof.

Further, the invention is concerned with a process and an intermediate for the manufacture of the above compounds, pharmaceutical preparations which contain such compounds, the use of these compounds for the production of pharmaceutical preparations.

The present invention provides the novel compounds of formula (I) which are CCR2 receptor antagonists, with some antagonist activity also at CCR3 and CCR5.

Unless otherwise indicated, the following definitions are set forth to illustrate and define the meaning and scope of the various terms used to describe the invention herein.

The term "halogen" or "halo" means fluorine, chlorine, bromine and iodine, with chlorine and fluorine being preferred.

The term "C$_{1-6}$ alkyl", alone or in combination with other groups, means a branched or straight-chain monovalent alkyl radical, having one to six carbon atoms. This term is further exemplified by such radicals as methyl, ethyl, n-propyl, isopropyl, n-butyl, s-butyl, t-butyl. C$_{1-4}$ alkyl or C$_{1-3}$ alkyl is more preferred. The term "C$_{2-6}$ alkyl" means the same as "C$_{1-6}$ alkyl", except that C$_{2-6}$ alkyl has two to six carbon atoms.

The term "hydroxy C$_{1-6}$ alkyl" means C$_{1-6}$ alkyl substituted by one or more, preferably one hydroxy group(s).

The term "halo C$_{1-6}$ alkyl" means C$_{1-6}$ alkyl substituted by one or more same or different halogen atoms.

The term "C$_{1-2}$ alkylene" means a linear saturated divalent hydrocarbon radical of one to two carbon atoms, such as methylene, ethylene.

The term "C$_{3-7}$ cycloalkyl", alone or in combination with other groups, means a saturated monovalent mono-cyclic hydrocarbon radical of three to seven ring carbons, e.g., cyclopropyl, cyclobutyl, cyclohexyl.

The term "C$_{7-10}$ bicycloalkyl", alone or in combination with other groups, means a saturated monovalent cyclic hydrocarbon radical of seven to ten ring carbons, having two rings, in which two or more ring carbon atoms of one ring are ring carbon atoms of the other ring, e.g., bicyclo[2.2.1]heptyl.

The term "C$_{1-6}$ alkoxy", alone or in combination with other groups, means the group R'—O—, wherein R' is a 1-6 alkyl.

The term "halo C$_{1-6}$ alkoxy", alone or in combination with other groups, means C$_{1-6}$ alkoxy substituted by one or more, preferably one to three halogens.

The term "C$_{1-6}$ alkylenedioxy" means —O—C$_{1-6}$ alkyl-O—. Methylenedioxy or 1,2-ethylenedioxy are preferred.

The term "C$_{3-6}$ alkenyl", alone or in combination with other groups, means a straight-chain or branched hydrocarbon residue comprising a carbon-carbon double bond, having three to six carbon atoms, provided that the carbon atom of the attachment point of the C$_{3-6}$ alkenyl to the rest of the molecule is not bonded to another carbon atom of the C$_{3-6}$ alkenyl by a carbon-carbon double bond. An example of C$_{3-6}$ alkenyl is 2-propenyl.

The term "C$_{3-6}$-alkynyl", alone or in combination with other groups, means a straight-chain or branched hydrocarbon residue comprising a carbon-carbon triple bond, having three to six carbon atoms, provided that the carbon atom of the attachment point of the C$_{3-6}$ alkynyl to the rest of the molecule is not bonded to another carbon atom of the C$_{3-6}$ alkynyl by a carbon-carbon triple bond. An example of C$_{3-6}$ alkynyl is 2-propynyl.

The term "acyl" means R—C(O)—, in which R is C$_{1-6}$ alkyl, halo C$_{1-6}$ alkyl, C$_{3-7}$ cycloalkyl or C$_{3-7}$ cycloalkyl C$_{1-6}$ alkyl.

The term "heterocyclyl", alone or combination with other groups, means non-aromatic mono- or bi-cyclic radicals of four to nine ring atoms in which one to three ring atoms are heteroatoms independently selected from N, O and S(O)$_n$ (where n is an integer from 0 to 2), the remaining ring atoms being C.

The term "aryl", alone or combination with other groups, means phenyl or naphthyl. The term "heteroaryl", alone or combination with other groups, means a monocyclic or bicyclic radical of 5 to 10 ring atoms having one to three ring heteroatoms independently selected from N, O, and S, the remaining ring atoms being C.

The term "bicyclic radicals" means radicals having two rings, in which two or more ring atoms of one ring are ring carbon atoms of the other ring.

The term, "C$_{1-6}$ alkylsulfonyl", "C$_{1-6}$ alkylsulfinyl" and "C$_{1-6}$ alkylthio" means C$_{1-6}$ alkyl-SO$_2$—, C$_{1-6}$ alkyl-SO— and C$_{1-6}$ alkyl-S—, respectively.

Preferred radicals for the chemical groups whose definitions are given above are those specifically exemplified in Examples.

Compounds of formula (I) can form pharmaceutically acceptable acid addition salts. Examples of such pharmaceutically acceptable salts are salts of compounds of formula (I) with physiologically compatible mineral acids, such as hydrochloric acid, hydrobromic acid, sulphuric acid, sulphurous acid or phosphoric acid; or with organic acids, such as methanesulphonic acid, p-toluenesulphonic acid, acetic acid, lactic acid, trifluoroacetic acid, citric acid, fumaric acid, maleic acid, tartaric acid, succinic acid or salicylic acid. The term "pharmaceutically acceptable salts" refers to such salts.

"Optional" or "optionally" means that the subsequently described event or circumstance may but need not occur, and that the description includes instances where the event or circumstance occurs and instances in which it does not. For example, "aryl group optionally substituted with an alkyl group" means that the alkyl may but need not be present, and the description includes situations where the aryl group is substituted with an alkyl group and situations where the aryl group is not substituted with the alkyl group.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

Compounds that have the same molecular Formula but differ in the nature or sequence of bonding of their atoms or the arrangement of their atoms in space are termed "isomers." Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, if a carbon atom is bonded to four different groups, a pair of enantiomers is possible. An enantiomer can be characterized by the absolute configuration of its asymmetric center and is described by the R- and S-sequencing rules of Cahn, Ingold and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The compounds of formula (I) can possess one or more asymmetric centers. Unless indicated otherwise, the description or naming of a particular compound in the specification and claims is intended to include both individual enantiomers and mixtures, racemic or otherwise, thereof, as well as individual epimers and mixture thereof. The methods for the determination of stereochemistry and the separation of stereoisomers are well-known in the art (see discussion in Chapter 4 of "Advanced Organic Chemistry", 4th edition J. March, John Wiley and Sons, New York, 1992).

While the broadest definition of this invention is described before, certain compounds of formula (I) are preferred.

i) In the compounds of formula (I), A is preferably phenyl or naphthyl, said phenyl and said naphthyl being optionally substituted by one to three same or different halogens. Preferably A is phenyl substituted by one or two halogen atoms independently selected from the group consisting of chlorine and fluorine. More preferably A is phenyl substituted by two halogen atoms independently selected from the group consisting of chlorine and fluorine, at 3 and 4 positions of the phenyl group. A is especially phenyl substituted by two chlorine atoms or one chlorine atom and one fluorine atom at 3 and 4 positions of the phenyl group.

ii) In the compounds of formula (I), X is preferably —N($R^1$)($R^2$).

More preferably, X is —N($R^1$)($R^2$) and $R^1$ and $R^2$, together with the nitrogen atom to which they are attached, form heterocyclyl optionally substituted by one to three substituents independently selected from the group consisting of $R^d$, and one of the ring carbon atoms of said heterocyclyl formed by $R^1$ and $R^2$ being optionally replaced with a carbonyl group; and/or one of the ring carbon atoms of the heterocyclyl formed by $R^1$ and $R^2$ may be a ring carbon atom of another ring which is $C_{3-7}$ cycloalkyl or heterocyclyl, one or two ring carbon atoms of said other ring being optionally replaced by a carbonyl group, and said other ring being optionally substituted by $C_{1-6}$ alkyl.

The heterocyclyl formed by $R^1$ and $R^2$, together with the nitrogen atom to which they are attached, is preferably piperidyl or pyrrolidinyl, and said piperidyl and pyrrolidinyl being optionally substituted by one or two substituents independently selected from the group consisting of hydroxy, $C_{1-6}$ alkyl and hydroxy $C_{1-6}$ alkyl, and/or one of the ring carbon atoms of said piperidyl and pyrrolidinyl formed by $R^1$ and $R^2$ may be shared by $C_{3-7}$ cycloalkyl ring.

More preferably, the heterocyclyl formed by $R^1$ and $R^2$, together with the nitrogen atom to which they are attached, is piperidyl or pyrrolidinyl, and said piperidyl and pyrrolidinyl being optionally substituted by hydroxy or hydroxymethyl, and/or one of the ring carbon atoms of said piperidyl and pyrrolidinyl formed by $R^1$ and $R^2$ may be shared by a cyclopropan ring.

In the compounds of formula (I), especially (S)-2-hydroxymethyl-pyrrolidin-1-yl, piperidin-1-yl or (S)-4-hydroxy-6-aza-spiro[2,5]oct-6-yl is preferred as X.

iii) In the compounds of formula (I), m+n is preferably an integer of 1, 2 or 3, more preferably 2.

iv) In the compounds of formula (I), $R^3$ and $R^4$ is preferably hydrogen, and the other is hydrogen or hydroxy, more preferably both $R^3$ and $R^4$ are hydrogen.

v) In the compounds of formula (I), preferably, one or two of $R^5$, $R^6$, $R^7$, $R^8$, $R^9$ and $R^{10}$ are $C_{1-6}$ alkyl and the others are hydrogen, more preferably, one of $R^5$ and $R^6$ is hydrogen or $C_{1-6}$ alkyl, the other is hydrogen, and $R^7$, $R^8$, $R^9$ and $R^{10}$ are hydrogen. Further more preferably, one of $R^5$ and $R^6$ is methyl, the other is hydrogen, and $R^7$, $R^8$, $R^9$ and $R^{10}$ are hydrogen.

vi) In the compounds of formula (I), Y is preferably C(O).

vii) In the compounds of formula (I), Y is preferably $S(O)_2$.

viii) Another preferred compound of the invention is a compound of formula (I), which is 4-[(E)-3-(3,4-Dichloro-phenyl)-acryloyl]-1-[3-((S)-2-hydroxymethyl-pyrrolidin-1-yl)-propyl]-piperazin-2-one, 4-[(E)-3-(3,4-Dichloro-phenyl)-acryloyl]-1-[3-((S)-2-hydroxymethyl-pyrrolidin-1-yl)-propyl]-3-methyl-piperazin-2-one, (E)-3-(3,4-Dichloro-phenyl)-1-[1,1-dioxo-2-(3-piperidin-1-yl-propyl)-1-l-6-[1,2,5]thiadiazinan-5-yl]-propenone, 4-[(E)-3-(3,4-Dichlorophenyl)-acryloyl]-1-[3-((S)-4-hydroxy-6-aza-spiro[2.5]oct-6-yl)-propyl]-3-methyl-piperazin-2-one, 4-[(E)-3-(3-Chloro-4-fluoro-phenyl)-acryloyl]-1-[3-((S)-4-hydroxy-6-aza-spiro[2.5]oct-6-yl)-propyl]-3-methyl-piperazin-2-one, (S)-4-[(E)-3-(3-Chloro-4-fluoro-phenyl)-acryloyl]-1-[3-((S)-4-hydroxy-6-aza-spiro[2.5]oct-6-yl)-propyl]-3-methyl-piperazin-2-one, (S)-4-[(E)-3-(3-Chloro-phenyl)-acryloyl]-1-[3-((S)-4-hydroxy-6-aza-spiro[2.5]oct-6-yl)-propyl]-3-methyl-piperazin-2-one or (S)-4-[(E)-3-(3,4-Dichloro-phenyl)-acryloyl]-3-methyl-1-(3-piperidin-1-yl-propyl)-piperazin-2-one.

General Synthetic Procedures

The compounds of formula (I) can be prepared by methods known in the art or as described below or in analogy thereto. Unless otherwise indicated, $R^1, R^2, R^3, R^4, R^5, R^6, R^7, R^8, R^9, R^{10}, R^{11}$, Y, m, and n are as described above. Starting materials are either commercially available or can be prepared by methods known in the art.

Compounds of formula (I), wherein X is $—N(R^1)(R^2)$ and Y is C(O), are represented by formula (Ia). They can optionally be converted to compounds of formula (Ib), wherein X is $—N^+(R^1)(R^2)(R^{11})$ and Y is C(O), by alkylation with $R^{11}$—X, wherein X is bromine or iodine, in a solvent, such as methanol, as described in scheme 1. Similarly, compounds of formula (I), wherein X is $—N(R^1)(R^2)$ and Y is $S(O)_2$, are represented by formula (Ic) and can optionally be converted to compounds of formula (Id), wherein X is $—N^+(R^1)(R^2)(R^{11})$ and Y is $S(O)_2$ (scheme 1).

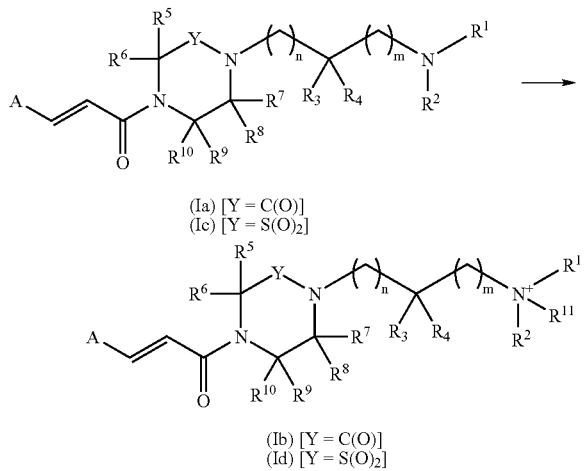

In Scheme 1, A, X, Y, $R^1, R^2, R^3, R^4, R^5, R^6, R^7, R^8, R^9, R^{10}$, m and n are as defined before.

Compounds of formula (Ia) can be produced as outlined in scheme 2. PG is a suitable protective group such as tert-butoxycarbonyl or benzyloxycarbonyl, LG is a leaving group such as chlorine, bromine, iodine, or methanesulfonyloxy.

In step a, scheme 2, protected piperazinone 1 is reacted with alkylating agent 2 in the presence of a base, e.g., sodium hydride or potassium tert-butylate, in a solvent such as N,N-dimethylformamide, N,N-dimethylacetamide or tetrahydrofuran, at temperatures between 0° C. and 100° C.

In step b, scheme 2, the protective group of 3 is removed using methods known in the art, thus leading to secondary amine 4. In the case where PG is tert-butoxycarbonyl, suitable deprotection reagents and conditions are strong acids such as hydrogen chloride or trifluoroacetic acid in a solvent such as 1,4-dioxane or dichloromethane, at or below room temperature. In the case where PG is benzyloxycarbonyl, the protective group is removed by hydrogenation at pressures between 1 and 100 bar, at temperatures between 0° C. and 100° C., in solvents such as methanol, ethanol, or ethyl acetate.

In step c, scheme 2, secondary amine 4 is converted to compound of general formula (Ia) through reaction with cinnamic acid derivative 5, using methods well known to someone skilled in the art e.g. amide formation using a coupling reagent. The reaction is typically carried out in aprotic solvents such as dichloromethane, tetrahydrofuran, N,N-dimethylformamide, N-methylpyrrolidinone and mixtures thereof at temperatures between 0° C. and 80° C. in the presence or absence of a base such as triethylamine, diisopropylethylamine, 4-methylmorpholine, and/or 4-(dimethylamino)pyridine. Typically used coupling agents are N,N'-dicyclohexylcarbodiimide, 1-(3-dimethylaminopropyl)-3-ethyl-carbodimide hydrochloride, O-(benzotriazol-1-yl)-N,N,N',N'-tetramethyluronium hexafluoro-phosphate, O-(7-azabenzotriazol-1-yl)-N,N,N',N'-tetramethyluronium hexafluoro-phosphate and bromo-tris-pyrrolidino-phosphonium hexafluorophosphate. Alternatively, this reaction can be performed in two steps involving first formation of the acyl halide derivative of 5 and subsequent coupling reaction with amine 4 in the presence of a base. Typically employed reagents for the formation of the acyl chloride are thionyl chloride, phosphorous pentachloride, oxalyl chloride or cyanuric chloride, and the reaction is generally conducted in the absence of a solvent or in the presence of an aprotic solvent like dichloromethane, toluene or acetone. A base can optionally be added, like for example pyridine, triethylamine, diisopropylethylamine or 4-methylmorpholine, and catalytic amounts of N,N-dimethylformamide may be used. The obtained acyl chloride can be isolated or reacted as such with amine 4 in an aprotic solvent, like dichloromethane, tetrahydrofuran or acetone, in the presence of a base. Typical bases are triethylamine, 4-methylmorpholine, pyridine, diisopropylethylamine or 4-(dimethylamino)pyridine or mixtures thereof.

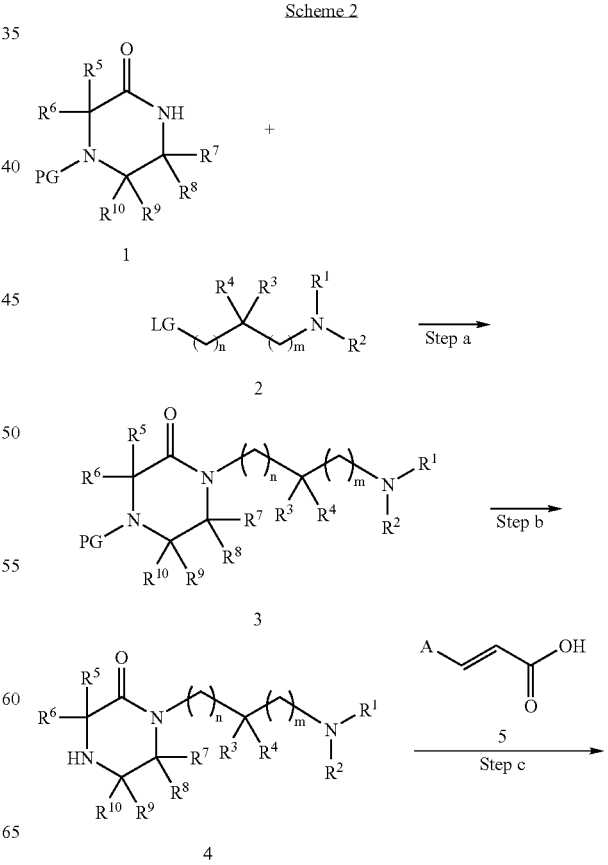

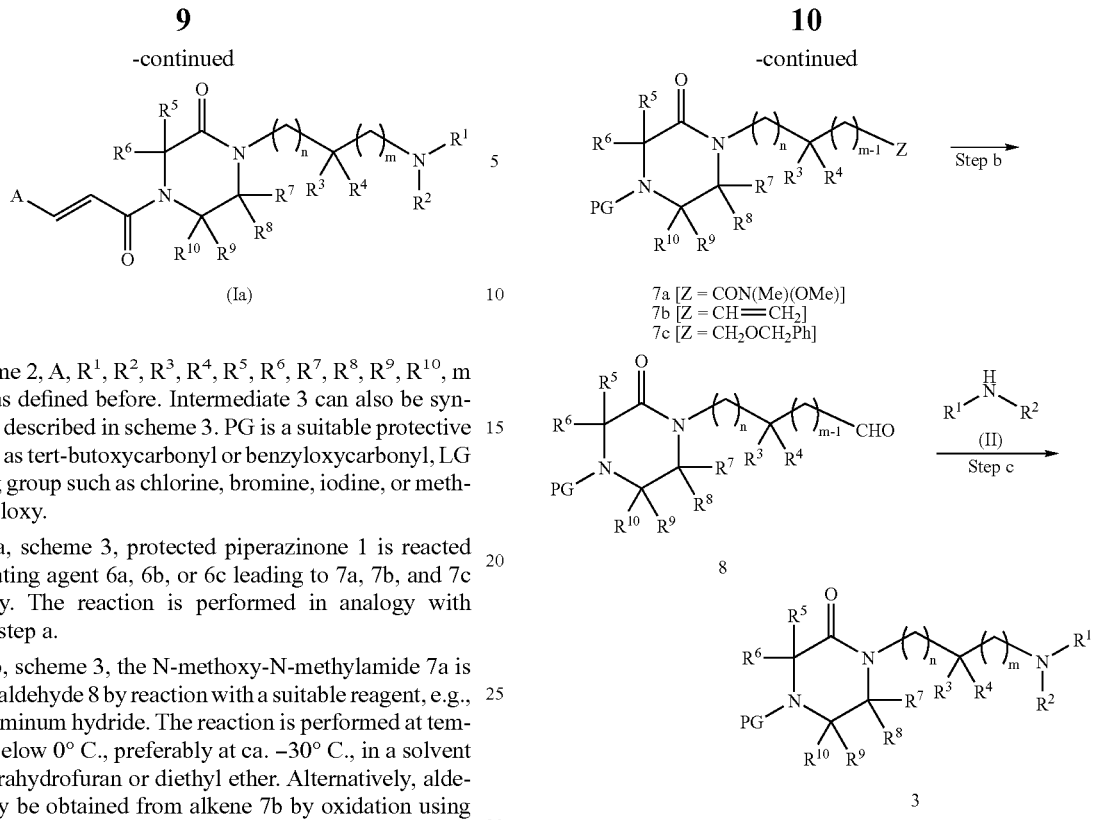

In Scheme 2, A, $R^1$, $R^2$, $R^3$, $R^4$, $R^5$, $R^6$, $R^7$, $R^8$, $R^9$, $R^{10}$, m and n are as defined before. Intermediate 3 can also be synthesized as described in scheme 3. PG is a suitable protective group such as tert-butoxycarbonyl or benzyloxycarbonyl, LG is a leaving group such as chlorine, bromine, iodine, or methanesulfonyloxy.

In step a, scheme 3, protected piperazinone 1 is reacted with alkylating agent 6a, 6b, or 6c leading to 7a, 7b, and 7c respectively. The reaction is performed in analogy with scheme 2, step a.

In step b, scheme 3, the N-methoxy-N-methylamide 7a is reduced to aldehyde 8 by reaction with a suitable reagent, e.g., lithium aluminum hydride. The reaction is performed at temperatures below 0° C., preferably at ca. −30° C., in a solvent such as tetrahydrofuran or diethyl ether. Alternatively, aldehyde 8 may be obtained from alkene 7b by oxidation using methods known in the art. Preferably, 7b is reacted with sodium periodate in the presence of catalytic amounts of osmium tetroxide, in solvents such as acetone, tert-butylalcohol, water, or mixtures thereof, at temperatures between 0° C. and 30° C. Alternatively, aldehyde 8 may be obtained from benzyl ether 7c, in analogy with scheme 11, steps a and c.

In step c, scheme 3, aldehyde 8 is transformed into 3 by reaction with amine (II), using methods well known in the art, e.g., reductive amination. The reaction is carried out using a suitable reducing agent, e.g., sodium borohydride, sodium triacetoxyborohydride, sodium cyanoborohydride, or borane pyridine complex, in solvents such as methanol, ethanol, acetic acid, dichloromethane, 1,2-dichloroethane, or mixtures thereof, at temperatures between 0° C. and 80° C.

Scheme 3

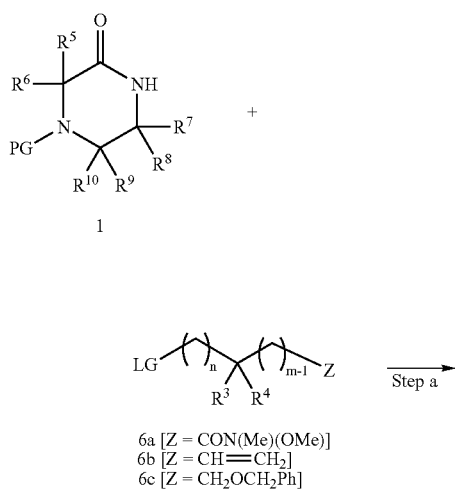

In Scheme 3, $R^1$, $R^2$, $R^3$, $R^4$, $R^5$, $R^6$, $R^7$, $R^8$, $R^9$, $R^{10}$, m and n are as defined before. Intermediate 3 can also be synthesized as described in scheme 4. PG is a suitable protective group such as tert-butoxycarbonyl or benzyloxycarbonyl, $LG^1$ and $LG^2$ are leaving groups such as chlorine, bromine, iodine, or methanesulfonyloxy.

In step a, scheme 4, protected piperazinone 1 is reacted with alkylating agent 9, leading to 10. The reaction is performed in analogy with scheme 2, step a.

In step b, scheme 4, intermediate 10 is reacted with amine (II), leading to 3. This reaction is carried out in a suitable solvent, e.g., N,N-dimethylformamide, N,N-dimethylacetamide, acetonitrile, tetrahydrofuran, in the presence of a base, e.g., potassium carbonate, cesium carbonate, triethylamine, at 0-100° C. Optionally, prior to step b, in the case where $LG^2$ is chlorine, intermediate 10 may be interconverted to the corresponding iodide (general structure 10 with $LG^2$=iodine) by reaction with sodium iodide in acetone or 2-butanone, preferably at the boiling point of the solvent.

Scheme 4

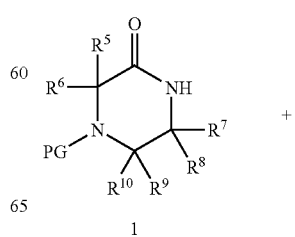

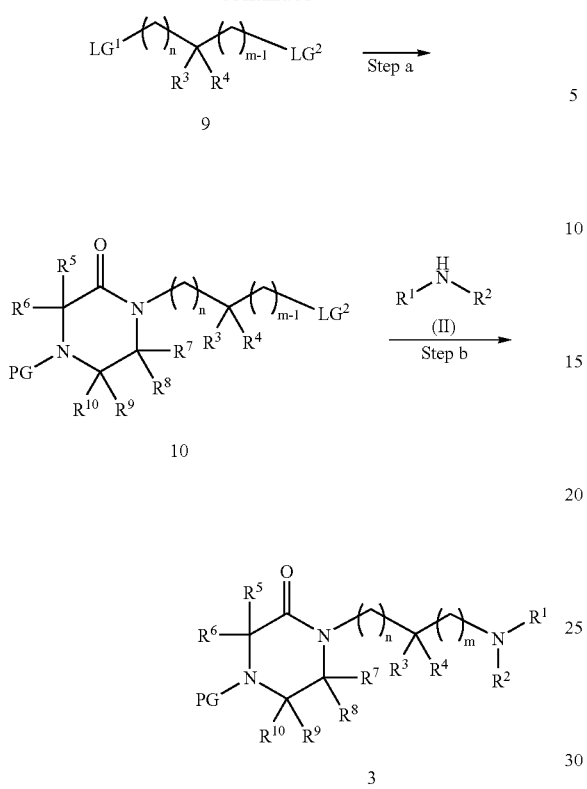

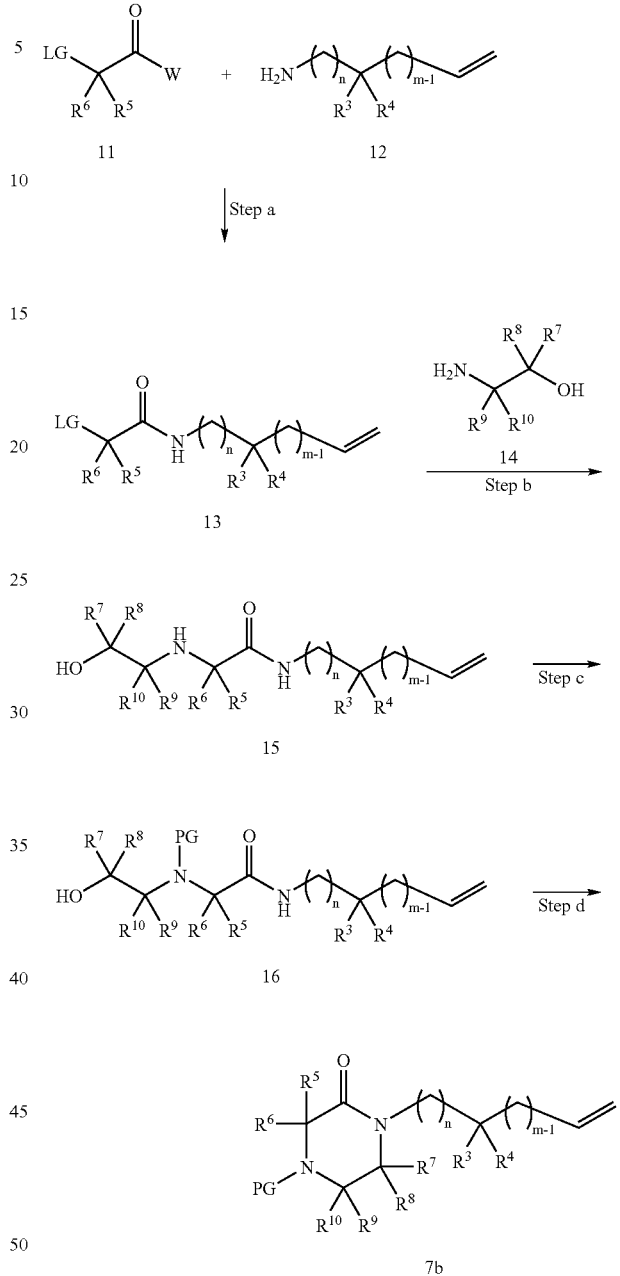

In Scheme 4, $R^1$, $R^2$, $R^3$, $R^4$, $R^5$, $R^6$, $R^7$, $R^8$, $R^9$, $R^{10}$, m and n are as defined before. Intermediate 7b can also be synthesized as described in scheme 5. PG is a suitable protective group such as tert-butoxycarbonyl or benzyloxycarbonyl, LG is a leaving group, preferably chlorine or bromine, W is either OH or a halogen, preferably chlorine or bromine. In step a, scheme 5, amine 12 is reacted with 11 as follows: In the case where 11 is an acyl chloride (W=chlorine or bromine), the reaction is performed in the presence of a base, e.g., triethylamine, in a solvent such as dichloromethane or tetrahydrofuran, at temperatures between −78° C. and 25° C. In the case where 11 is a carboxylic acid (W=OH), the reaction is carried out in analogy with scheme 2, step c.

In step b, scheme 5, haloacetamide 13 undergoes nucleophilic substitution with aminoalcohol 14, leading to 15. This reaction is carried out in a solvent such as acetone, acetonitrile, or N,N-dimethylformamide, in the presence of a base, e.g., sodium hydrogencarbonate, potassium hydrogencarbonate or triethylamine.

In step c, scheme 5, secondary amine 15 is protected with a suitable protective group using methods known in the art. Preferably, PG is tert-butoxycarbonyl, and the transformation of 15 to 16 is carried out with di-tert-butyl-dicarbonate, in a solvent such as dichloromethane, optionally in the presence of a base, e.g., triethylamine, at 0-40° C.

In step d, scheme 5, δ-hydroxyamide 16 is cyclized to piperazinone 7b using methods well known in the art, e.g., Mitsunobu reaction. This reaction requires a phosphine, preferably triphenylphosphine, and a dialkyl-azodicarboxylate, e.g., diethyl azodicarboxylate or diisopropyl azodicarboxylate and is performed in an inert solvent, e.g., tetrahydrofuran or toluene, at temperatures between 0° C. and 100° C.

In Scheme 5, $R^3$, $R^4$, $R^5$, $R^6$, $R^7$, $R^8$, $R^9$, $R^{10}$, m and n are as defined before. Intermediate 7b can also be synthesized as described in scheme 6. PG is a suitable protective group such as tert-butoxycarbonyl or benzyloxycarbonyl, LG is a leaving group, preferably trifluoromethanesulfonyloxy or bromine.

In step a, scheme 6, amine 12 is reacted with carboxylic acid 17 in analogy with scheme 2, step c, leading to 18.

In step b, scheme 6, amide 18 is cyclized with ethane derivative 19, leading to 7b. This reaction is performed in an inert solvent such as tetrahydrofuran or N,N-dimethylformamide, at temperatures between −20° C. and room temperature, in the presence of a base, e.g., sodium hydride or potassium tert-butylate.

Scheme 6

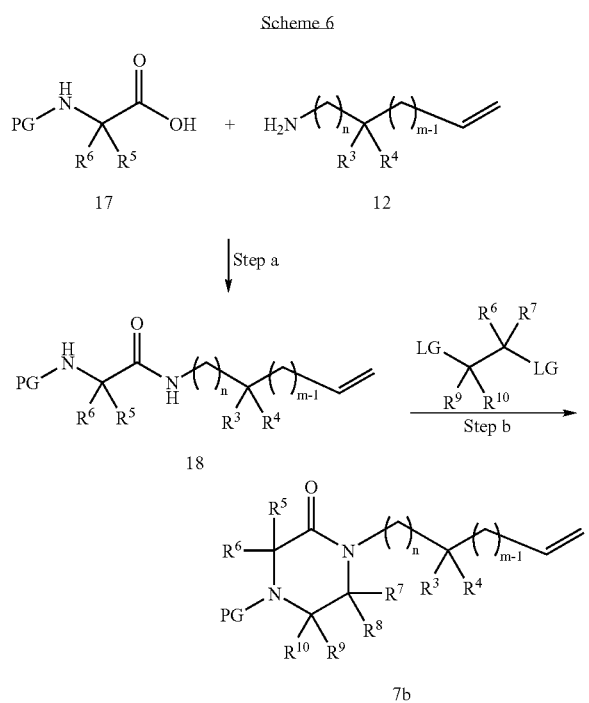

Scheme 7

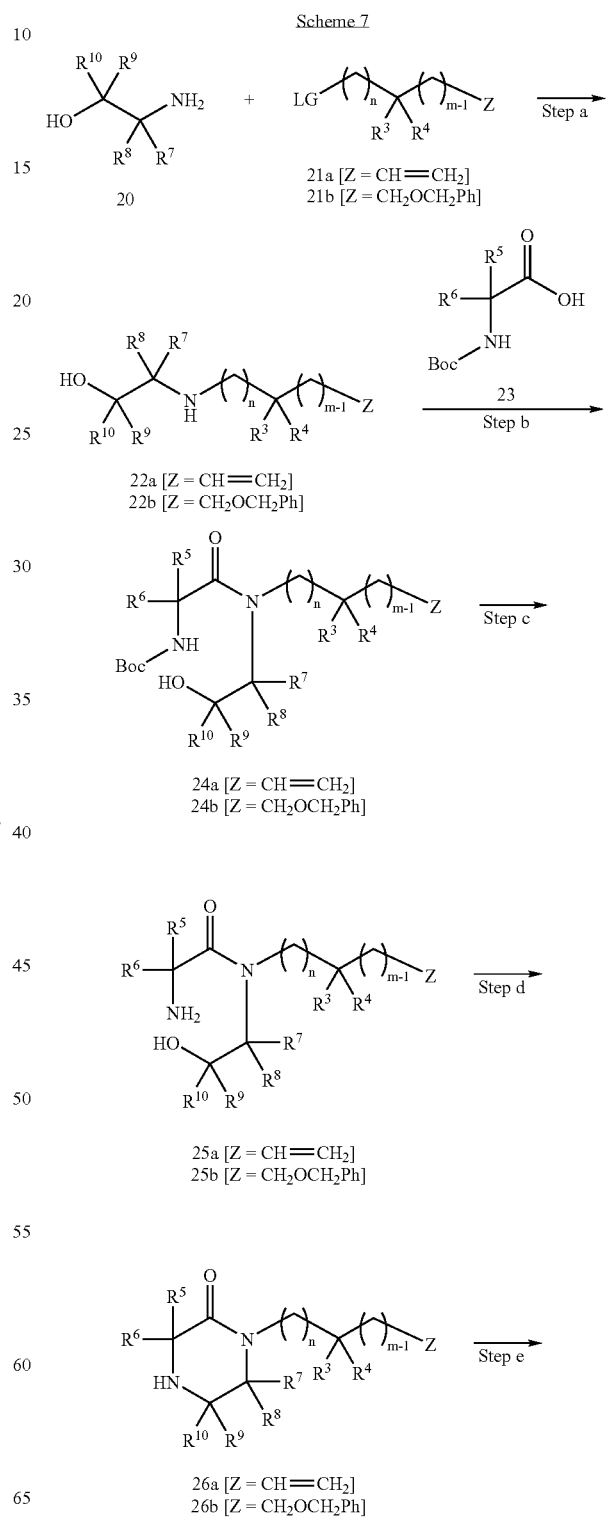

In Scheme 6, $R^3$, $R^4$, $R^5$, $R^6$, $R^7$, $R^8$, $R^9$, $R^{10}$, m and n are as defined before. Intermediates 7b and 7c can also be synthesized as described in scheme 7. PC is a suitable protective group, e.g., tert-butoxycarbonyl or benzyloxycarbonyl, LG is a leaving group, preferably chlorine or bromine.

In step a, scheme 7, aminoalcohol 20 is reacted with halide 21a or 21b by nucleophilic substitution, leading to secondary amine 22a and 22b, respectively, using methods known in the art. For instance, the reaction is carried out in a solvent such as methanol, ethanol, or acetonitrile, at temperatures between 20° C. and the boiling point of the solvent, in the presence of a base, e.g., potassium hydrogencarbonate, potassium carbonate, optionally in the presence of sodium iodide.

In step b, scheme 7, secondary amine 22a or 22b is coupled with tert-butoxycarbonyl-(Boc-) protected amino acid 23 to produce amide 24a and 24b, respectively, in analogy with scheme 2, step c.

In step c, scheme 7, the tert-butyl carbamate protecting group of amino acid amide 24a or 24b is removed, leading to 25a and 25b, respectively. Suitable deprotection reagents and conditions are strong acids such as hydrogen chloride or trifluoroacetic acid in a solvent such as 1,4-dioxane or dichloromethane, at or below room temperature.

In step d, scheme 7, the N-(hydroxyethyl)-aminoacetamide 25a or 25b is cyclized to piperazinone 26a and 26b, respectively, in analogy to scheme 5, step d.

Alternatively, in the case where $R^{10} \neq H$, piperazinones 26a and 26b, respectively may also be obtained from 25a or 25b by (i) oxidation of the alcohol group in analogy with scheme 11, step c, and (ii) subsequent reduction and concomitant removal of the tert-butyl carbamate group of the aldehyde or hemiaminal intermediate with triethylsilane in trifluoroacetic acid, in a solvent such as dichloromethane, at about 0° C.

In step e, scheme 7, piperazinone 26a or 26b is converted into the N-protected derivative 7b and 7c, respectively, using methods and reagents known in the art. In the case where PG is tert-butoxycarbonyl, the reaction is performed using di-tert-butyl-dicarbonate in a solvent such as dichloromethane, optionally in the presence of a base, e.g., triethylamine, at room temperature. In the case where PG is benzyloxycarbonyl, the reaction is performed using benzyl chloroformate and a base, e.g., sodium hydrogencarbonate or triethylamine, in solvents such as acetone, water, tetrahydrofuran, methanol, or mixtures thereof, at 0-30° C.

15

-continued

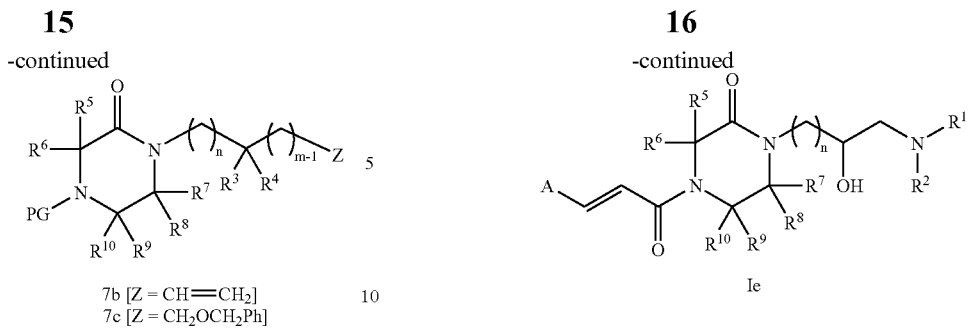

7b [Z = CH=CH₂]
7c [Z = CH₂OCH₂Ph]

In Scheme 7, $R^3$, $R^4$, $R^5$, $R^6$, $R^7$, $R^8$, $R^9$, $R^{10}$, m and n are as defined before.

Compound of general formula (Ia), wherein $R^3$ is OH, $R^4$ is H, aid m is 1, are represented by formula (Ie). Compounds (Ie) can be synthesized as described in scheme 8. PG is a suitable protective group such as tert-butoxycarbonyl or benzyloxycarbonyl, LG is a leaving group, preferably chlorine or bromine.

In step a, scheme 8, piperazinone 1 is alkylated with haloalkyl-oxirane 27, leading to 28. The reaction is performed in analogy with scheme 2, step a.

In step b, scheme 8, epoxide 28 is reacted with amine (II) to produce aminoalcohol 29. The reaction is performed in a solvent such as tetrahydrofuran, N,N-dimethylformamide, or N,N-dimethylacetamide, in the presence of a base, e.g., potassium carbonate or cesium carbonate, at 0-50° C.

The preparation of amides of general formula Ie from compounds of formula 29 follows the same synthetic route as that described in the preparation of Ia from the intermediate 4 (Scheme 2, step b and c)

16

-continued

Ie

In Scheme 8, $R^1$, $R^2$, $R^5$, $R^6$, $R^7$, $R^8$, $R^9$, $R^{10}$ and n are as defined before.

Protected piperazinones of formula I are either commercially available or can be produced according to methods known in the art (see e.g., *Org. Prep. Proced. Int.* 2002, 34, 367), e.g., as shown in scheme 9. PG is a suitable protective group, e.g., tert-butoxycarbonyl or benzyloxycarbonyl, LG is a leaving group, preferably chlorine or bromine, $R^a$ is lower alkyl, preferably methyl or ethyl.

In step a, scheme 9, haloacetate 30 is reacted with 1,2-diaminoethane derivative 31, leading to piperazinone 32. This reaction is performed in a solvent such as methanol or ethanol, in the presence of a base, such as sodium methylate, potassium carbonate, or potassium tert-butoxide, at 0-100° C.

In step b, scheme 9, piperazinone 32 is converted into the protected derivative 1, in analogy with scheme 7, step e.

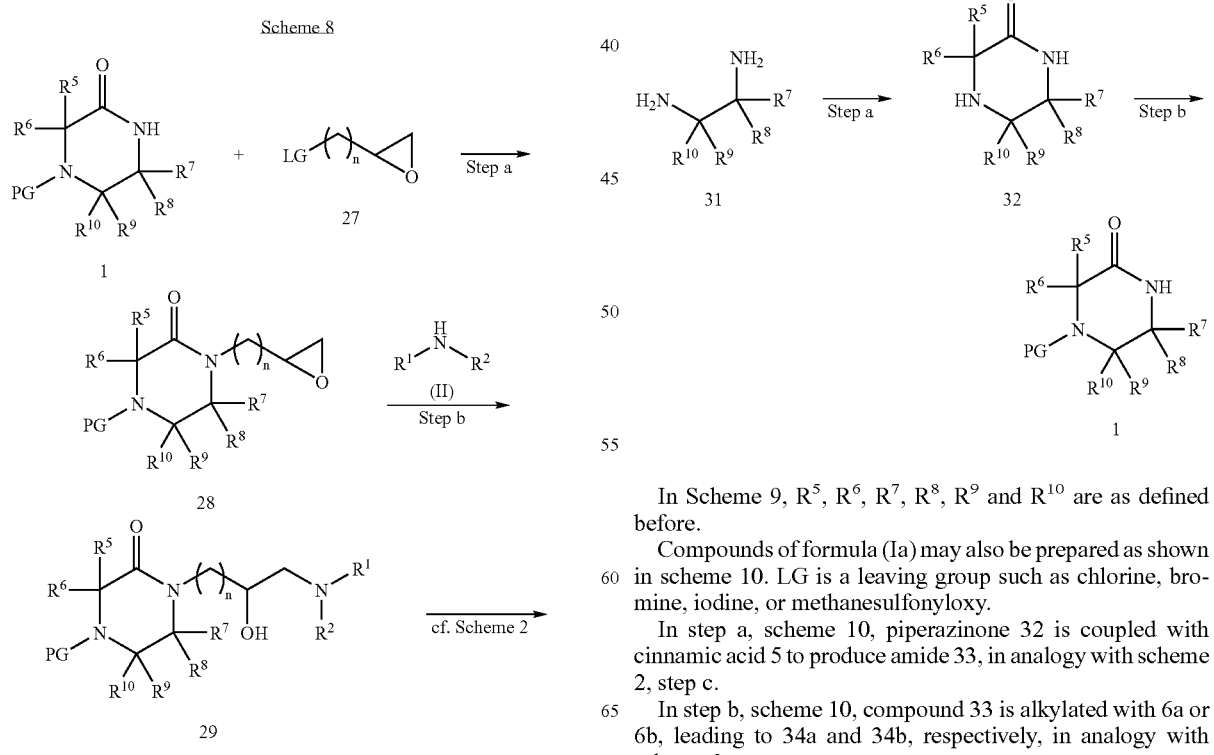

In Scheme 9, $R^5$, $R^6$, $R^7$, $R^8$, $R^9$ and $R^{10}$ are as defined before.

Compounds of formula (Ia) may also be prepared as shown in scheme 10. LG is a leaving group such as chlorine, bromine, iodine, or methanesulfonyloxy.

In step a, scheme 10, piperazinone 32 is coupled with cinnamic acid 5 to produce amide 33, in analogy with scheme 2, step c.

In step b, scheme 10, compound 33 is alkylated with 6a or 6b, leading to 34a and 34b, respectively, in analogy with scheme 3, step a.

In step c, scheme 10, compound 34a or 34b is transformed into aldehyde 35, as described in scheme 3, step b.

In step d, scheme 10, aldehyde 35 is reacted with amine (II), in analogy to scheme 3, step c, leading to compound (Ia).

Alternatively, amide intermediate 33 may be converted directly to (Ia) by reaction with alkylating agent 2, in analogy with scheme 2, step a.

In Scheme 10, A, $R^1$, $R^2$, $R^3$, $R^4$, $R^5$, $R^6$, $R^7$, $R^8$, $R^9$, $R^{10}$, m and n are as defined before.

Intermediate 35 can also be synthesized as outlined in scheme 11.

In step a, scheme 11, the benzyl ether group of 26b is cleaved, leading to alcohol 36, using methods known in the art, e.g., catalytic hydrogenation. For instance, the reaction is carried out in a suitable solvent, e.g., methanol or ethanol, at temperatures between 0° C. and 150° C., under a hydrogen atmosphere at pressures between 1 bar and 100 bar, in the presence of a suitable catalyst, e.g., palladium on activated charcoal.

In step b, scheme 11, amine 36 is reacted with cinnamic acid derivative 5, in analogy with scheme 2, step c, leading to amide 37.

In step c, scheme 11, alcohol 37 is oxidized to aldehyde 35, using reagents and method known in the art. For instance, the oxidation is carried out with sodium hypochlorite, in a two-phase mixture of water and dichloromethane, in the presence of sodium hydrogencarbonate and catalytic amounts of potassium bromide and 2,2,6,6-tetramethylpiperidin-1-oxyl radical, at temperatures between 0° C. and 25° C. Alternatively, the oxidation may be performed with catalytic amounts of tetrapropylammonium perruthenate in the presence of stoichiometric amounts of a co-oxidant such as 4-methylmorpholine-4-oxide and molecular sieves, at temperatures between 0° C. and 40° C., in solvents such as dichloromethane, acetonitrile or mixtures thereof. Alternatively, dimethyl sulfoxide-based reagents can be employed, such as dimethyl sulfoxide-oxalyl chloride, or dimethyl sulfoxide-trifluoroacetic anhydride, in a solvent such as dichloromethane, at temperatures below 0° C., typically between −78° C. and −60° C.

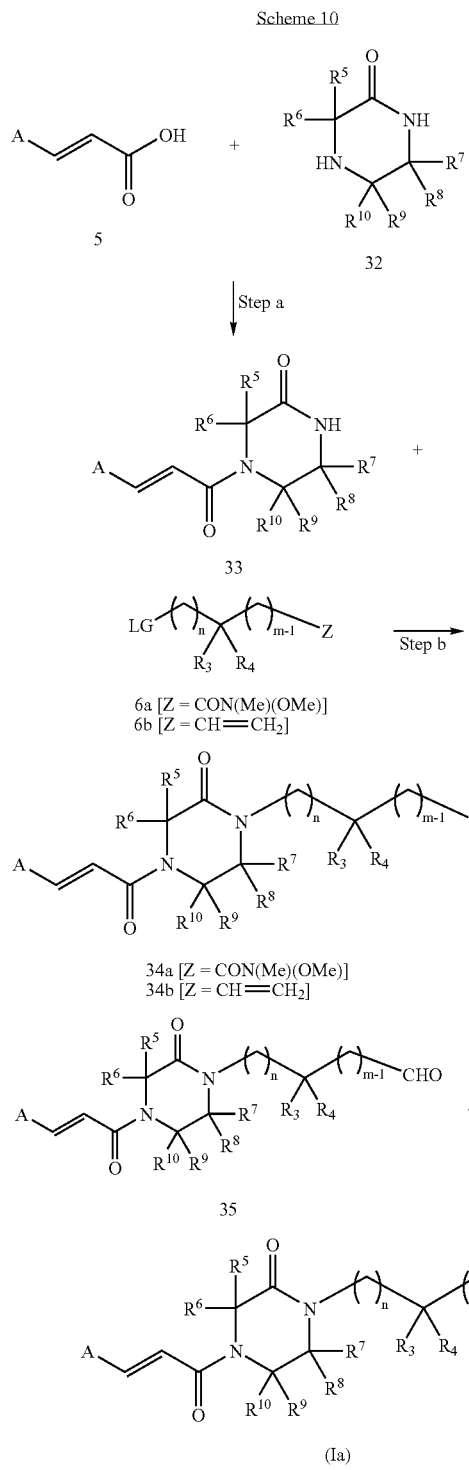

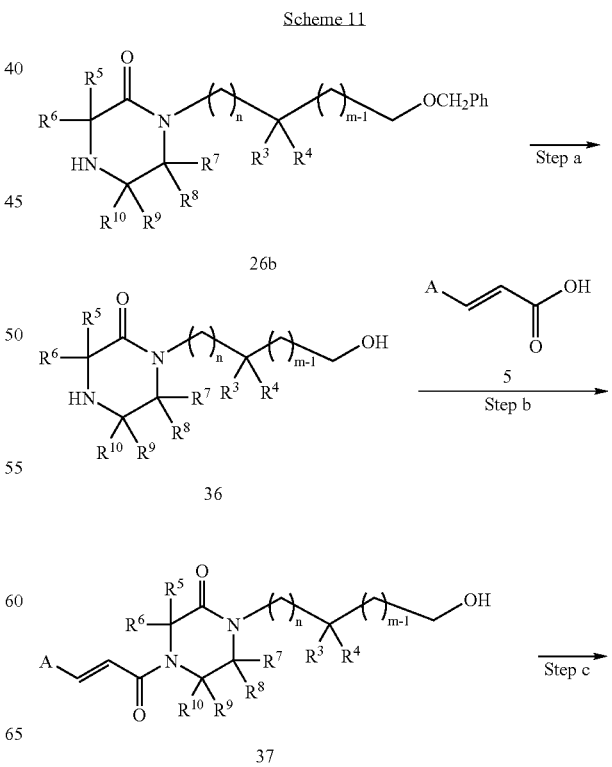

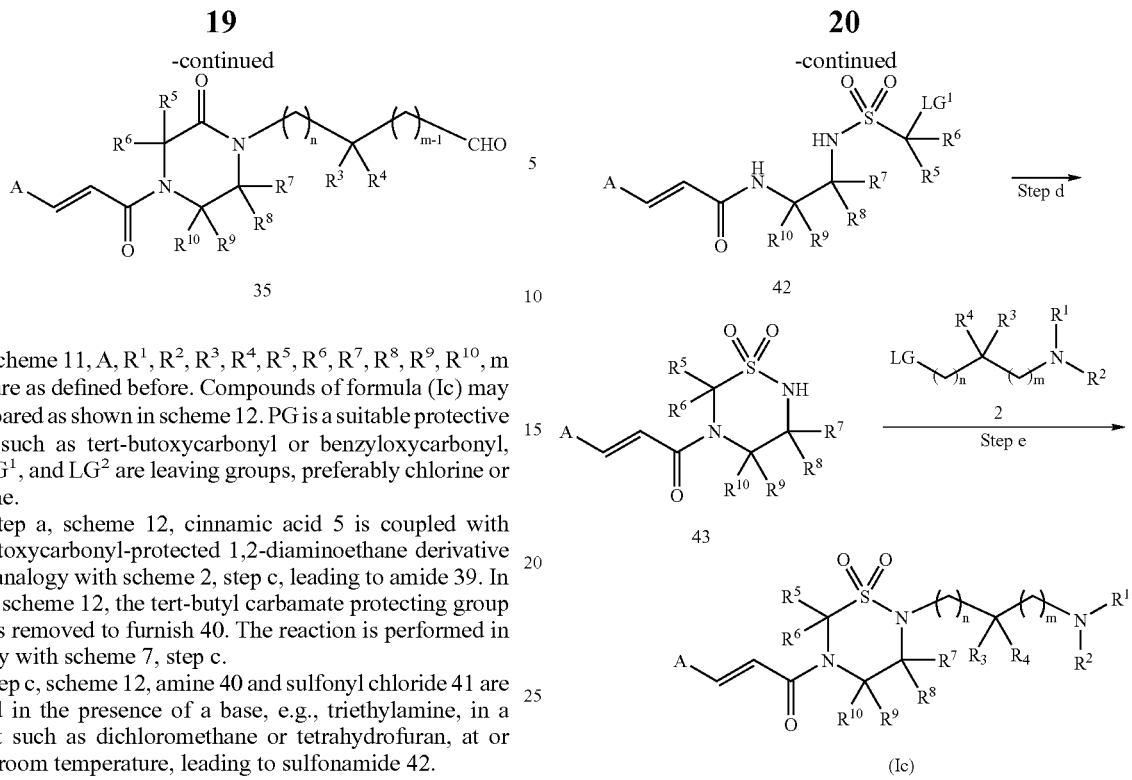

In Scheme 11, A, $R^1$, $R^2$, $R^3$, $R^4$, $R^5$, $R^6$, $R^7$, $R^8$, $R^9$, $R^{10}$, m and n are as defined before. Compounds of formula (Ic) may be prepared as shown in scheme 12. PG is a suitable protective group such as tert-butoxycarbonyl or benzyloxycarbonyl, LG, $LG^1$, and $LG^2$ are leaving groups, preferably chlorine or bromine.

In step a, scheme 12, cinnamic acid 5 is coupled with tert-butoxycarbonyl-protected 1,2-diaminoethane derivative 38, in analogy with scheme 2, step c, leading to amide 39. In step b, scheme 12, the tert-butyl carbamate protecting group of 39 is removed to furnish 40. The reaction is performed in analogy with scheme 7, step c.

In step c, scheme 12, amine 40 and sulfonyl chloride 41 are reacted in the presence of a base, e.g., triethylamine, in a solvent such as dichloromethane or tetrahydrofuran, at or below room temperature, leading to sulfonamide 42.

In step d, scheme 12, halomethyl-sulfonamide 42 is treated with a base, e.g., sodium hybride or potassium tert-butylate, in a solvent such as N,N-dimethylformamide or tetrahydrofuran, at 0-60° C. This reaction produces 1,1-dioxo-[1,2,5]-thiadiazinane derivative 43.

In step e, scheme 12, intermediate 43 is alkylated with building block 2, leading to (Ic). This reaction is performed in the presence of a base, e.g., sodium hydride, potassium tert-butylate, potassium carbonate, or cesium carbonate, in a solvent such as N,N-dimethylformamide, acetonitrile, or tetrahydrofuran, at 20-100° C.

Scheme 12

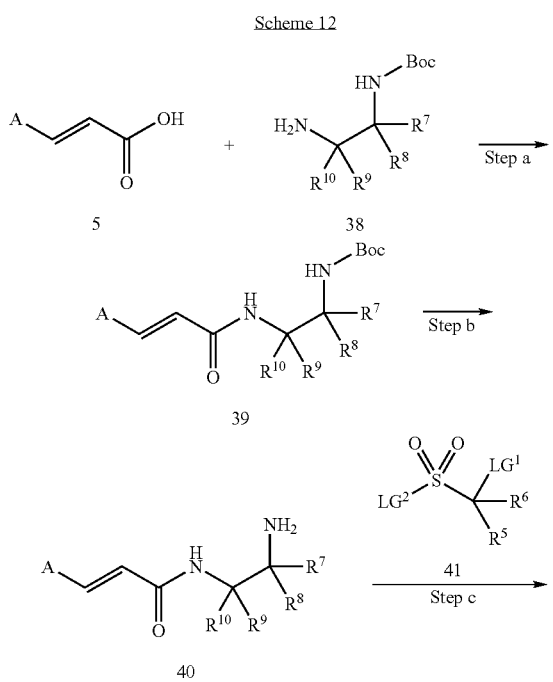

In Scheme 12, A, $R^1$, $R^2$, $R^3$, $R^4$, $R^5$, $R^6$, $R^7$, $R^8$, $R^9$, $R^{10}$, m and n are as defined before.

Amines of formula (II) are either commercially available or can be synthesized as described in the experimental section.

More specifically, (S)-6-aza-spiro[2.5]octan-4-ol (44) can be prepared as outlined in scheme 13. $R^a$ is benzyl, allyl, or lower alkyl, e.g., methyl, ethyl or tert-butyl, preferably tert-butyl. The synthesis of allylic alcohol 45 with $R^a$=tert-butyl is described in the literature.

In step a, scheme 13, cyclopropanation of allylic alcohol 45 leads to 4-hydroxy-6-aza-spiro[2.5]octane-1-carboxylic acid ester 46. This conversion is accomplished, e.g., using a carbenoid resulting from treatment of diiodomethane or chloroiodo methane with diethylzinc, in an inert solvent such as toluene, dichloromethane, dichloroethane, or diethylether, at temperatures between 0° C. and the boiling point of the solvent. Preferred conditions involved the use of diiodomethane in an inert solvent such as toluene or dichloromethane, preferably toluene. The reaction is preferably conducted between 10° C. and 50° C., more preferably between 20° C. and 30° C., even more preferably between 20° C. and 25° C. Several orders of addition are possible, for example adding diethylzinc to a mixture of the allylic alcohol and diiodomethane or adding the alcohol to the preformed zinc carbenoid (obtained from reaction of diethyl zinc and for example diiodomethane). The latter is not favored due to the know thermal instability of these reagent and the risk of runaway behavior of such mixtures. The preferred mode of addition consists in the addition of diiodomethane to a preformed mixture of diethylzinc and the allylic alcohol. The addition is usually performed over 2-3 h allowing a good control of the evolving reaction heat. The reaction can also be transposed into continuous mode after appropriate adaptation of the reaction conditions. Not being strictly restricted to these values, the preferred stoichiometry is 2 equivalents of diethylzinc and 3 equivalents of diiodomethane per equivalent of allylic alcohol. After completion of the cyclopropanation, the reaction mixture may be quenched with a carboxylic acid, preferably 2-ethylhexanoic acid and then worked up or can be directly introduced in an aqueous work-up.

In step b, scheme 13, alcohol 46 is oxidized to ketone 47, using methods and reagents known in the art. For instance, the oxidation is carried out with sodium hypochlorite, in a two-phase mixture of water and dichloromethane, in the presence of sodium hydrogencarbonate and catalytic amounts of sodium bromide or potassium bromide and 2,2,6,6-tetramethylpiperidin-1-oxyl radical, at temperatures between 0° C. and 25° C. Alternatively, the oxidation may be performed with catalytic amounts of tetrapropylammonium perruthenate in the presence of stoichiometric amounts of a co-oxidant such as 4-methylmorpholine-4-oxide and molecular sieves, at temperatures between 0° C. and 40° C., in solvents such as dichloromethane, acetonitrile or mixtures thereof. Alternatively, dimethyl sulfoxide-based reagents can be employed, such as e.g. dimethyl sulfoxide-oxalyl chloride, or dimethyl sulfoxide-trifluoroacetic anhydride, in the presence of an organic base such as triethylamine in a solvent such as dichloromethane, at temperatures below 0° C., typically between −78° C. and −60° C. Alternatively, pyridine-sulphur trioxide can be employed in dimethyl sulfoxide or dimethylsulfoxide-dichloromethane solvent mixture in the presence of an organic base such as triethylamine, at temperatures between 0° C. and 25° C.

In step c, scheme 13, ketone 47 is transformed to optically enriched (S)-4-hydroxy-6-aza-spiro[2.5]octane-1-carboxylic acid ester 48 by enantioselective enzymatic reduction. A screening for the asymmetric reduction of ketone 47 to (S)-alcohol 48 revealed ketoreductases KRED-NADP-104, KRED-NAD-123, KRED-NAD-111 and KRED-NAD-117 (all from BioCatalytics, now Codexis) to be highly selective and tolerant to higher substrate concentrations. The regeneration of the respective cofactors (NAD or NADP) might be effected by regeneration systems known in the art, e.g. based on the use of glucose/GDH or formic acid/FDH or based on applying an excess of isopropanol. Preferentially KRED-NAD-117 is used, an optimized reaction system of which is described (see experimental section). Optionally, the enzyme might be used in immobilized form, as whole cell catalyst or in genetically modified form.

Alternatively, optically enriched (S)-alcohol 48 can be obtained from racemate 46 by high pressure liquid chromatography separation using a chiral stationary phase. Suitable conditions are a Chiralpak® AD column as stationary phase and heptane/2-propanol 19:1 as the eluent.

Alternatively, optically enriched (S)-alcohol 48 can be obtained from racemate 46 by enantioselective enzymatic transesterification of the undesired (R)-enantiomer using an enol ester as an acyl donor in nearly anhydrous organic solvents. Suitable enzymes turned out to be lipases from *Candida antarctica* form B (one commercial form of which is Chirazyme L-2, Roche), *Alcaligenes* sp. (commercial forms of which is Lipase PL or QLM, Meito Sangyo) or *Pseudomonas stutzeri* (one commercial form of which is Lipase TL, Meito Sangyo), respectively, the latter of which is preferred. Elevated reaction temperatures as high as the boiling point of the organic solvent might be employed (see experimental section). Preferred acyl donors are vinyl acetate to caproate whereby the longer-chain acylates might facilitate workup. The mixture of (S)-alcohol 48 and e.g. the O-butyryl derivative of the (R)-enantiomer of 46 might be separated by chromatography or crystallization or counter-current extraction.

In step d, scheme 13, the carbamate protective group of 48 is removed, using methods and reagents known in the art.

Preferably, in the case where $R^a$ is tert-butyl, the reaction is carried out with hydrogen chloride in solvents such as 1,4-dioxane, ethyl acetate, methanol, ethanol, 2-propanol, water, or mixtures thereof, at temperatures between 0° C. and 50° C., leading to 44 as its hydrochloride salt, which is used as such as described in schemes 3, 4, 8, and 10.

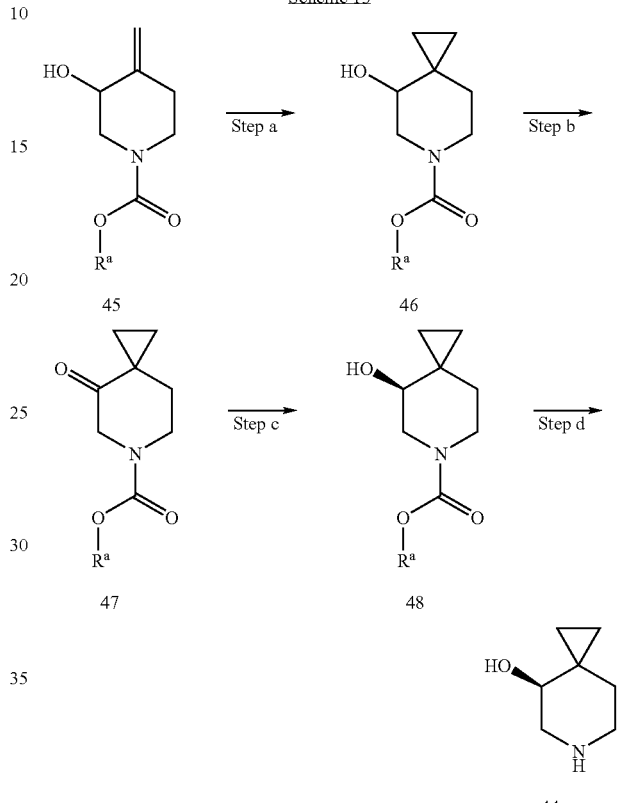

Scheme 13

Alternatively, optically enriched (S)-alcohol 48 may also be prepared as illustrated in scheme 14.

$R^a$ is benzyl, allyl, or lower alkyl, e.g., methyl, ethyl, or tert-butyl, preferably tert-butyl.

In step a, scheme 14, optically enriched (S)-allylic alcohol 49 is obtained from racemate 45 by enantioselective enzymatic transesterification of the undesired (R)-enantiomer using again an enol ester as acyl donor as described above. Suitable enzymes turned out to be lipases from *Candida antarctica* form B, *Achromobacter* sp. (a commercial form of which is Lipase AL, Meito Sangyo) or *Thermomyces lanuginosus* (one commercial form of which is Lipozyme TL IM, Novozymes), respectively, the latter of which is preferred. Again, vinyl acylates as donors in nearly anhydrous organic solvents at elevated reaction temperature can be used (see experimental section), and the separation of the mixture of (S)-alcohol 49 and the acylated derivative of the (R)-enantiomer of 45 by means of chromatography or counter-current extraction might be enhanced by longer acyl chains.

Alternatively, optically enriched (S)-alcohol 49 can be obtained from racemate 45 by high pressure liquid chromatography separation using a chiral stationary phase.

In step b, scheme 14, allylic alcohol 49 is cyclopropanated to 48, in analogy to scheme 13, step a.

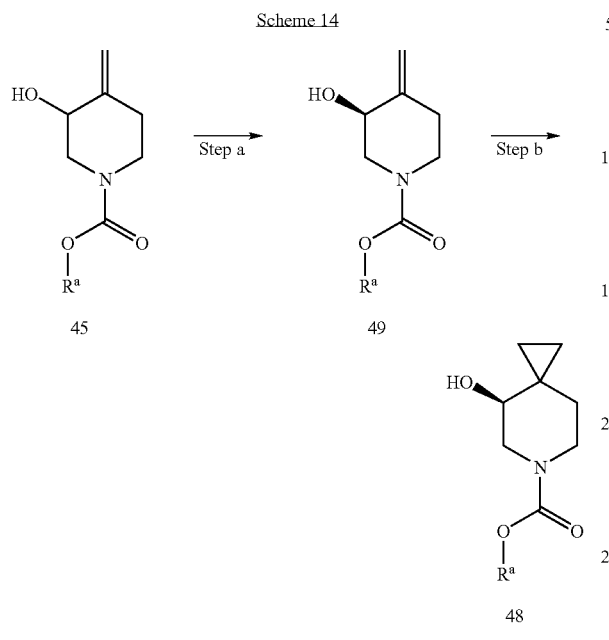

Alternatively, (S)-6-aza-spiro[2.5]octan-4-ol (44) can be prepared as outlined in scheme 15. The synthesis of the starting materials, 1-(2-oxoethyl)-cylopropanecarboxylic acid tert-butyl ester (50) and N-benzylglycine tert-butyl ester (51) is described in the literature (see experimental part for details).

In step a, scheme 15, aldehyde 50 and amine 51 are converted to compound 52 in a reductive amination reaction, using reagents and conditions well known in the art. The reaction is carried out in the presence of a suitable reducing agent, e.g., sodium borohydride, sodium triacetoxyborohydride, sodium cyanoborohydride, or borane pyridine complex, in solvents such as methanol, ethanol, acetic acid, dichloromethane, 1,2-dichloroethane, or mixtures thereof, at temperatures between 0° C. and 80° C. Preferred conditions involve the use of sodium triacetoxyborohydride.

In step b, scheme 15, diester 52 undergoes a Dieckmann condensation, leading to β-enol ester 53 (as keto-enol tautomers). This reaction is performed in the presence of a strong base, e.g., lithium hexamethyldisilazanide or potassium tert-butylate, in a solvent such as tetrahydrofuran, at temperatures between 0° C. and 50° C. Preferred conditions involve the use of lithium hexamethyldisilazanide in tetrahydrofuran at a temperature between 0° C. and 50° C., preferably between 20° C. and 30° C.

In step c, scheme 15, tert-butyl ester 53 is subjected to acidic conditions, whereupon it undergoes hydrolysis and decarboxylation, leading to 6-benzyl-6-aza-spiro[2.5]octan-4-one (54). Suitable acids are e.g., sulfuric acid, hydrochloric acid, phosphoric acid, formic acid, preferably in water, at temperatures between 0° C. and 100° C. Preferred conditions involve the use of aqueous sulfuric acid at 40° C. The amine 54 can be isolated as a salt, for example its hydrochloride (54 HCl), which can be used as such in the next step.

In step d, scheme 15, ketone 54 is transformed to optically enriched alcohol 55 by enantioselective enzymatic reduction. A screening for the asymmetric reduction of ketone 54 to (S)-alcohol 55 revealed ketoreductases KRED-NAD-101, KRED-NAD-102, KRED-NAD-117, KRED-NAD-123, and KRED-NADP-104 (all from BioCatalytics, now Codexis) to be highly selective and tolerant to higher substrate concentrations. The regeneration of the respective cofactors (NAD or NADP) might be effected by regeneration systems known in the art, e.g. based on the use of glucose/GDH or formic acid/FDH or based on applying an excess of isopropanol. Preferentially KRED-NAD-117 is used, an optimized reaction system of which is described (see experimental section). Optionally, the enzyme might be used in immobilized form, as whole cell catalyst or in genetically modified form.

In step e, scheme 15, the benzyl protective group of amine 55 is removed, e.g., by catalytic hydrogenation, thereby furnishing (S)-6-aza-spiro[2.5]octan-4-ol (44). This reaction is performed under a hydrogen atmosphere at pressures between 1 bar and 100 bar, in the presence of a suitable catalyst, e.g., palladium on activated charcoal or palladium on barium sulfate, in a solvent such as methanol, ethanol, acetic acid, ethyl acetate, water or mixtures thereof, at temperatures between 20° C. and 80° C.

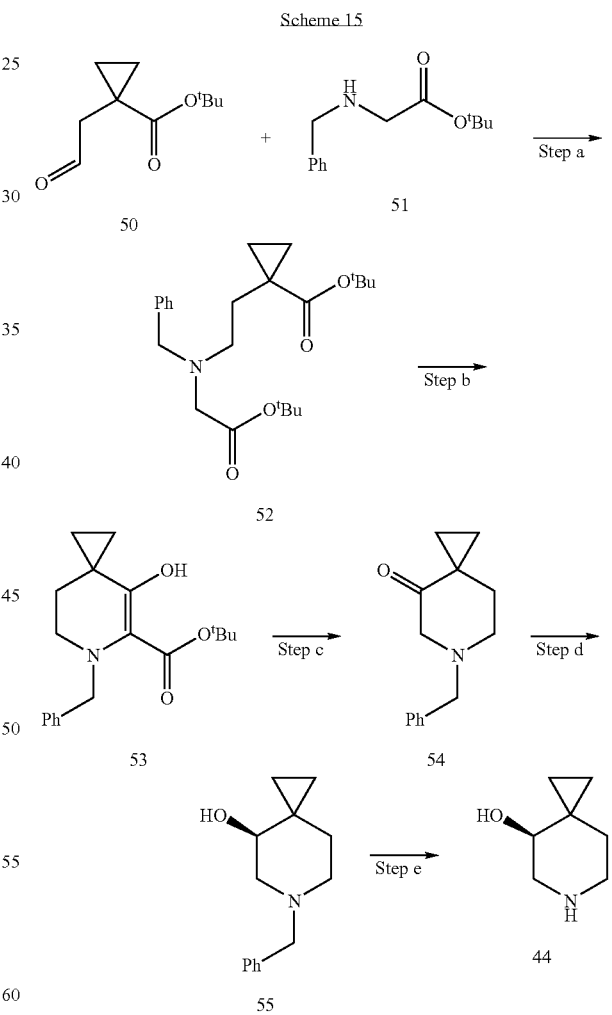

Compounds of formula I can have one or more asymmetric carbon atoms and can exist in the form of optically pure enantiomers, mixtures of enantiomers such as, for example, racemates, optically pure diastereoisomers, mixtures of diastereoisomers, diastereoisomeric racemates or mixtures of diastereoisomeric racemates. The optically active forms can be obtained for example by resolution of the racemates, by asymmetric synthesis or asymmetric chromatography (chromatography with a chiral adsorbent or eluent). The invention embraces all of these forms.

As described above, the compounds of formula (I) are CCR2 receptor antagonists, with some antagonist activity also at CCR3 and CCR5. These compounds consequently prevent migration of various leukocyte populations through the blockade of CCR2 stimulation. They therefore can be used for the treatment and/or prevention of inflammatory and/or allergic diseases, such as peripheral arterial occlusive disease, critical limb ischemia (CLI), vulnerable atherosclerotic plaque patients, unstable angina, congestive heart failure, left ventricular hypertrophy, ischemia reperfusion injury, stroke, cardiomyopathy, restenosis, rheumatoid arthritis, diabetic nephropathy, irritable bowel syndrome, Crohn's disease, multiple sclerosis, neuropathic pain, atherothrombosis and/or burns/ulcers in diabetes/CLI, and asthma.

Prevention and/or treatment of inflammatory diseases, particularly peripheral arterial occlusive diseases or atherothrombosis is the preferred indication.

The invention therefore also relates to pharmaceutical compositions comprising a compound as defined above and a pharmaceutically acceptable excipient.

The invention likewise embraces compounds as described above for use as therapeutically active substances, especially as therapeutically active substances for the treatment and/or prophylaxis of inflammatory and/or allergic diseases, particularly as therapeutically active substances for the treatment and/or prophylaxis of peripheral arterial occlusive disease, critical limb ischemia, vulnerable atherosclerotic plaque patients, unstable angina, congestive heart failure, left ventricular hypertrophy, ischemia reperfusion injury, stroke, cardiomyopathy, restenosis, rheumatoid arthritis, diabetic nephropathy, irritable bowel syndrome, Crohn's disease, multiple sclerosis, neuropathic pain, atherothrombosis, burns/ulcers in diabetes/CLI, and allergy, asthma. The invention also relates to the use of compounds as described above for the preparation of medicaments for the therapeutic and/or prophylactic treatment of inflammatory and/or allergic diseases, particularly for the therapeutic and/or prophylactic treatment of peripheral arterial occlusive disease, critical limb ischemia, vulnerable atherosclerotic plaque patients, unstable angina, congestive heart failure, left ventricular hypertrophy, ischemia reperfusion injury, stroke, cardiomyopathy, restenosis, rheumatoid arthritis, diabetic nephropathy, irritable bowel syndrome, Crohn's disease, multiple sclerosis, neuropathic pain, atherothrombosis, burns/ulcers in diabetes/CLI, and asthma. Such medicaments comprise a compound as described above.

The invention also relates to the process and the intermediates for manufacturing the compounds of formula (I) as well as the process for manufacturing the intermediates.

CCR2 receptor antagonistic activity by the compounds of the present invention can be demonstrated by the following assays.

Receptor Binding Assays

Binding assays were done with membranes from CHOK1-CCR2B-A5 cells (Euroscreen) stably overexpressing the human CCR2B.

Membranes were prepared by homogenizing the cells in 10 mM Tris pH 7.4, 1 mM EDTA, 0.05 mM benzamidine, leupeptin 6 mg/L and separating the debris at 1000 g. The membranes were then isolated at 100000 g in 50 mM Tris pH 7.4, $MgCl_2$ 10 mM, EGTA 1 mM, glycerol 10%, benzamidine 0.05 mM, leupeptin 6 mg/l.

For binding, CCR2 antagonist compounds were added in various concentrations in 50 mM HEPES pH 7.2, 1 mM $CaCl_2$, 5 mM $MgCl_2$, 0.5% BSA, 0.01% $NaN_3$, together with 100 pM $^{125}$I-MCP-1 (PerkinElmer, 2200 Ci/mmol) to about 5 fMol CCR2 membranes and incubated for 1 hour at room temperature. For unspecific control 57.7 nM MCP-1 (R&D Systems or prepared at Roche) was added. Membranes were harvested through GF/B (glass fiber filter; PerkinElmer) plates, equilibrated with 0.3% polyethylenimine, 0.2% BSA, air dried and binding was determined by counting in a topcounter (NXT Packard). Specific binding was defined as total binding minus nonspecific binding and typically represents about 90-95% of the total binding. Antagonist activity is indicated as inhibitor concentration required for 50% inhibition ($IC_{50}$) of specific binding.

Calcium Mobilization Assay

CHOK1-CCR2B-A5 cells (from Euroscreen) stably overexpressing the human chemokine receptor 2 isoform B were cultured in Nutrient Hams F12 medium supplemented with 5% FBS, 100 U/ml penicillin, 100 µg/ml streptomycin, 400 µg/ml G418 and 5 µg/ml puromycin. For the assay cells were grown overnight in 384-well black clear flat bottom polystyrene plates (Costar) at 37° C. at 5% $CO_2$. After washing with DMEM, 20 mM Hepes, 2.5 mM probenecid, 0.1% BSA (DMEM assay buffer) cells were loaded with 4 µM Fluo-4 in the same DMEM assay buffer for 2 hours at 30° C. Excess dye was removed and cells were washed with DMEM assay buffer. 384-well compound plates were prepared with DMEM assay buffer/0.5% DMSO with or without various concentrations of test compounds. Usually compounds were tested for agonist and antagonist activity.

Test compounds were added to the assay plate and agonist activity was monitored as fluorescence for 80 seconds with a FLIPR (488 nm excitation; 510-570 nm emission; Molecular Devices). After 20-30 min. of incubation at 30° C., 20 nM MCP-1 (R&D; Roche) was added and fluorescence was monitored again for 80 seconds. Increases in intracellular calcium are reported as maximum fluorescence after agonist exposure minus basal fluorescence before exposure. Antagonist activity is indicated as inhibitor concentration required for 50% inhibition of specific calcium increases.

The compounds I of the present invention exhibit $IC_{50}$ values in the Ca mobilisation assay of 1 nM to 10 µM, preferably 1 nM to 1.5 µM for CCR2. The following table shows measured values for some selected compounds of the present invention.

| Example | IC50 (µM) |
| --- | --- |
| Example 11 | 0.2837 |
| Example 14 | 0.3071 |
| Example 15 | 0.0765 |
| Example 34 | 0.202 |
| Example 39 | 0.0137 |

The compounds of formula (I) and/or their pharmaceutically acceptable salts can be used as medicaments, e.g. in the form of pharmaceutical preparations for enteral, parenteral or topical administration. They can be administered, for example, perorally, e.g. in the form of tablets, coated tablets, dragées, hard and soft gelatine capsules, solutions, emulsions or suspensions, rectally, e.g. in the form of suppositories, parenterally, e.g. in the form of injection solutions or suspensions or infusion solutions, or topically, e.g. in the form of ointments, creams or oils. Oral administration is preferred.

The production of the pharmaceutical preparations can be effected in a manner which will be familiar to any person skilled in the art by bringing the described compounds of formula I and/or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatine capsules. Suitable carrier materials for soft gelatine capsules are, for example, vegetable oils, waxes, fats and semi-solid and liquid polyols (depending on the nature of the active ingredient no carriers might, however, be required in the case of soft gelatine capsules). Suitable carrier materials for the production of solutions and syrups are, for example, water, polyols, sucrose, invert sugar. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavour-improving agents, salts for varying the osmotic pressure, buffer substances, solubilizers, colorants and masking agents and antioxidants come into consideration as pharmaceutical adjuvants.

The dosage of the compounds of formula (I) can vary within wide limits depending on the disease to be controlled, the age and the individual condition of the patient and the mode of administration, and will, of course, be fitted to the individual requirements in each particular case. For adult patients a daily dosage of about 1 to 1000 mg, especially about 1 to 300 mg, comes into consideration. Depending on severity of the disease and the precise pharmacokinetic profile the compound could be administered with one or several daily dosage units, e.g. in 1 to 3 dosage units.

The pharmaceutical preparations conveniently contain about 1-500 mg, preferably 1-100 mg, of a compound of formula (I).

EXAMPLES

The following Examples serve to illustrate the present invention in more detail. They are, however, not intended to limit its scope in any manner.
Abbreviations:
aq.=aqueous, FDH=Formate dehydrogenase, FTIR=Fourier transform infrared spectroscopy, GC=gas chromatography, GDH=Glucose dehydrogenase, HPLC=high pressure liquid chromatography, IPC=in-process control, NAD=Nicotinamide adenine dinucleotide, NADP=Nicotinamide adenine dinucleotide phosphate, sat.=saturated, TLC=thin layer chromatography Intermediate 1

4-[(E)-3-(3,4-Dichloro-phenyl)-acryloyl]-3-methyl-piperazin-2-one

A solution of 3,4-dichlorocinnamic acid (190 mg, 0.88 mmol), 3-methylpiperazin-2-one (100 mg, 0.88 mmol), 4-methylmorpholine (443 mg, 4.38 mmol), and O-(7-azabenzotriazol-1-yl)-N,N,N',N'-tetramethyluronium hexafluorophosphate (500 mg, 1.31 mmol) in N,N-dimethylformamide (1 ml) was stirred at room temperature for 3 h, then the reaction mixture was partitioned between water and ethyl acetate. The organic layer was washed with brine, dried ($MgSO_4$), and evaporated. Chromatography ($SiO_2$; $CH_2Cl_2$/MeOH 95:5) produced the title compound (192 mg, 70%). White solid, MS (ISP)=313.1 $(M+H)^+$.

Intermediate 2

4-[(E)-3-(3,4-Dichloro-phenyl)-acryloyl]-piperazin-2-one

The title compound, was produced as described in intermediate 1 from 3,4-dichlorocinnamic acid and piperazin-2-one. White solid, MS (ISP)=299.2 $(M+H)^+$.

Intermediate 3

4-[(E)-3-(3-Chloro-phenyl)-acryloyl]-piperazin-2-one

A solution of oxalyl chloride (4.19 g, 33.0 mmol) in dichloromethane (12.5 ml) was added dropwise at room temperature to a solution of 3-chlorocinnamic acid (5.48 g, 30.0 mmol) and N,N-dimethylformamide (2 drops) in dichloromethane (240 ml). After 2 h the solution was evaporated and the residue redissolved in dichloromethane (160 ml), then a solution of piperazin-2-one (2.70 g, 27 mmol) and triethylamine (6.07 g, 60.0 mmol) in dichloromethane (80 ml) was added dropwise at 0° C. The reaction mixture was allowed to reach room temperature over 16 h, then poured onto 10% aq. potassium hydrogensulfate solution. The organic layer was washed with sat. aq. sodium hydrogencarbonate solution and 10% aq. sodium chloride solution, dried, and evaporated to produce the title compound (5.12 g, 72%). Yellow solid, MS (EI)=264.1 $(M)^+$.

Intermediate 4

4-[(E)-3-(3,4-Dichloro-phenyl)-acryloyl]-3,3-dimethyl-piperazin-2-one

The title compound was produced as described in intermediate 1 from 3,4-dichlorocinnamic acid and 3,3-dimethyl-piperazin-2-one. White solid, MS (ISP)=327.1 $(M+H)^+$.

Intermediate 5

4-{4-[(E)-3-(3,4-Dichloro-phenyl)-acryloyl]-2-oxo-piperazin-1-yl}-N-methoxy-N-methyl-butyramide A solution of 4-[(E)-3-(3,4-dichloro-phenyl)-acryloyl]-piperazin-2-one (intermediate 2; 1.00 g, 3.34 mmol) and 4-bromo-N-methoxy-N-methyl-butyramide (*Org. Lett.* 2002, 4, 3047; 726 mg, 3.68 mmol) was cooled to 0° C. and treated with sodium hydride (55% dispersion in oil, 151 mg, 3.68 mmol). The reaction mixture was kept at 0° C. for 2 h, then heated at 50° C. for 16 h. After cooling, volatile material was removed by rotary evaporation, then the residue was taken up in toluene/methanol and concentrated again. Chromatography ($CH_2Cl_2$/MeOH/$NH_4OH$ 95:5:0.25) afforded the title compound (63 mg, 4%). Yellow oil, MS (ISP)=428.1 $(M+H)^+$.

Intermediate 6

3-Oxo-4-(2-pyrrolidin-1-yl-ethyl)-piperazine-1-carboxylic acid tert-butyl ester Sodium hydride (55% dispersion in mineral oil, 1.96 g, 45 mmol) was added portionwise at room temperature to a solution of 3-oxo-piperazine-1-carboxylic acid tert-butyl ester (6.01 g, 30.0 mmol) in N,N-dimethylacetamide (150 ml), then a solution of 1-(2-chloroethyl)-pyrrolidine in toluene [prepared from commercially available 1-(2-chloroethyl)-pyrrolidine hydrochloride (16.1 g, 94.5 mmol) by partitioning between toluene (70 ml) and 1 M aq. sodium hydroxide solution (70 ml) and drying of the organic layer with $Na_2SO_4$] was added dropwise. The reaction mixture was stirred at room temperature for 16 h, then heated at 75° C. for 80 min. After cooling, the reaction mixture was partitioned between diethyl ether amid sat. aq. sodium hydrogencarbonate solution. The organic layer was dried ($Na_2SO_4$) and evaporated. Crystallization of the residue from diethyl ether afforded the title compound (3.74 g, 42%). White solid, MS (ISP)=298.2 $(M+H)^+$.

Intermediate 7

4-[3-((R)-2-Hydroxymethyl-pyrrolidin-1-yl)-propyl]-3-oxo-piperazine-1-carboxylic acid tert-butyl ester a) 4-But-3-enyl-3-oxo-piperazine-1-carboxylic acid tert-butyl ester Sodium hydride (60% dispersion in mineral oil, 42 mg, 1.05 mmol) was added at room temperature to a solution of 3-oxo-piperazine-1-carboxylic acid tert-butyl ester (200 mg, 1.00 mmol) in N,N-dimethylformamide (4 ml), then after 10 min a solution of 4-bromo-1-butene (148 mg, 1.10 mmol) in tetrahydrofuran (1 ml) was added dropwise. The reaction mixture was stirred for 3 h at room temperature, then another portion of 4-bromo-1-butene (40 mg, 0.30 mmol) was added dropwise, and the reaction mixture was heated at 50° C. for 18 h. After cooling, the reaction mixture was partitioned between water and heptane/ethyl acetate 1:1. The organic layer was washed with brine, dried ($MgSO_4$), and evaporated. Chromatography ($SiO_2$; heptane/ethyl acetate 1:1) afforded the title compound (217 mg, 81%). Colorless oil, MS (ISP)=255.2 $(M+H)^+$.

b) 4-[3-((R)-2-Hydroxymethyl-pyrrolidin-1-yl)-propyl]-3-oxo-piperazine-1-carboxylic acid tert-butyl ester Sodium metaperiodate (505 mg, 2.36 mmol) and osmium (VIII) oxide (2.5% solution in tert-butylalcohol, 80 µl, 7.9 µmol) were added at 0° C. to a solution of 4-but-3-enyl-3-oxo-piperazine-1-carboxylic acid tert-butyl ester (200 mg, 0.79 mmol) in acetone/water 1:1 (10 ml). After 30 min, the reaction mixture was allowed to reach room temperature over 45 min, then partitioned between ethyl acetate and water. The organic layer was washed with brine, dried ($MgSO_4$), and evaporated. The crude aldehyde intermediate (3-oxo-4-(3-oxo-propyl)-piperazine-1-carboxylic acid tert-butyl ester) and D-prolinol (95 mg, 0.94 mmol) were dissolved in 1,2-dichloroethane (2 ml), then a freshly prepared solution of pyridine borane complex (8 M in pyridine, 0.24 ml, 1.9 mmol) and acetic acid (170 mg, 2.83 mmol) in ethanol (2 ml) was added dropwise at room temperature. The reaction mixture was stirred overnight, then 25%. aq. ammonium hydroxide solution (0.39 ml) was added, and volatile material was removed by rotary evaporation. The residue was purified by chromatography ($SiO_2$; $CH_2Cl_2$/MeOH/$NH_4OH$ 80:20:0.25) to afford the title compound (160 mg, 60%). Light brown oil, MS (ISP) –342.1 $(M+H)^+$.

Intermediate 8

4-[3-(3-Hydroxy-piperidin-1-yl)-propyl]-3-oxo-piperazine-1-carboxylic acid tert-butyl ester The title compound was produced as described in intermediate 7b from 4-but-3-enyl-3-oxo-piperazine-1-carboxylic acid tert-butyl ester (intermediate 7a) and piperidin-3-ol. Light yellow oil, MS (ISP)=342.3 $(M+H)^+$.

Intermediate 9

4-[3-((S)-2-Hydroxymethyl-pyrrolidin-1-yl)-propyl]-3-oxo-piperazine-1-carboxylic acid tert-butyl ester The title compound was produced as described in intermediate 7b from 4-but-3-enyl-3-oxo-piperazine-1-carboxylic acid tert-butyl ester (intermediate 7a) and L-prolinol. Colorless oil, MS (ISP)=342.3 $(M+H)^+$.

Intermediate 10

4-[3-(4-Hydroxy-piperidin-1-yl)-propyl]-3-oxo-piperazine-1-carboxylic acid tert-butyl ester The title compound was produced as described in intermediate 7b from 4-but-3-enyl-3-oxo-piperazine-1-carboxylic acid tert-butyl ester (intermediate 7a) and piperidin-4-ol. Colorless oil, MS (ISP)=342.3 $(M+H)^+$.

Intermediate 11

3-Oxo-4-(3-pyrrolidin-1-yl-propyl)-piperazine-1-carboxylic acid tert-butyl ester The title compound was produced as described in intermediate 7b from 4-but-3-enyl-3-oxo-piperazine-1-carboxylic acid tert-butyl ester (intermediate 7a) and pyrrolidine. Light brown oil, MS (ISP)=312.3 $(M+H)^+$.

Intermediate 12

4-[3-(3-Hydroxy-pyrrolidin-1-yl)-propyl]-3-oxo-piperazine-1-carboxylic acid tert-butyl ester The title compound was produced as described in intermediate 7b from 4-but-3-enyl-3-oxo-piperazine-1-carboxylic acid tert-butyl ester (intermediate 7a) and pyrrolidin-3-ol. Light brown oil, MS (ISP)=328.3 $(M+H)^+$.

Intermediate 13

4-[3-(3-Hydroxymethyl-pyrrolidin-1-yl)-propyl]-3-oxo-piperazine-1-carboxylic acid tert-butyl ester The title compound was produced as described in intermediate 7b from 4-but-3-enyl-3-oxo-piperazine-1-carboxylic acid tert-butyl ester (intermediate 7a) and pyrrolidin-3-ylmethanol. Light brown oil, MS (ISP)=328.3 $(M+H)^+$.

Intermediate 14

2-Methyl-3-oxo-4-(3-pyrrolidin-1-yl-propyl)-piperazine-1-carboxylic acid tert-butyl ester a) 2-Methyl-3-oxo-piperazine-1-carboxylic acid tert-butyl ester

Di-tert-butyl dicarbonate (1.99 g, 9.12 mmol) was added at room temperature to a solution of 3-methyl-2-oxopiperazine (1.04 g, 9.12 mmol) in dichloromethane (10 ml). After 16 h the reaction mixture was poured onto water. The organic layer was washed with brine, dried (MgSO$_4$), and concentrated to produce the title compound (2.12 g, 100%). White solid, MS (ISP) 215.3 (M+H)$^+$.

b) 4-But-3-enyl-2-methyl-3-oxo-piperazine-1-carboxylic acid tert-butyl ester The title compound was produced as described in intermediate 7a from 2-methyl-3-oxo-piperazine-1-carboxylic acid tert-butyl ester and 4-bromo-t-butene. Colorless oil, MS (ISP) 269.3 (M+H)$^+$.

c) 2-Methyl-3-oxo-4-(3-pyrrolidin-1-yl-propyl)-piperazine-1-carboxylic acid tert-butyl ester The title compound was produced from 4-but-3-enyl-2-methyl-3-oxo-piperazine-1-carboxylic acid tert-butyl ester by oxidation to 2-methyl-3-oxo-4-(3-oxo-propyl)-piperazine-1-carboxylic acid tert-butyl ester, followed by reductive amination with pyrrolidin-3-yl-methanol, as described in intermediate 7b. Light brown oil, MS (ISP)=328.3 (M+H)$^+$.

Intermediate 15

4-[3-((S)-2-Hydroxymethyl-pyrrolidin-1-yl)-propyl]-2-methyl-3-oxo-piperazine-1-carboxylic acid tert-butyl ester The title compound was produced as described in intermediate 7b from 4-but-3-enyl-2-methyl-3-oxo-piperazine-1-carboxylic acid tert-butyl ester (intermediate 14b) and L-prolinol. Light brown oil, MS (ISP)=356.3 (M+H)$^+$.

Intermediate 16

4-[3-(4-Hydroxy-piperidin-1-yl)-propyl]-2-methyl-3-oxo-piperazine-1-carboxylic acid tert-butyl ester The title compound was produced as described in intermediate 7b from 4-but-3-enyl-2-methyl-3-oxo-piperazine-1-carboxylic acid tert-butyl ester (intermediate 14b) and piperidin-4-ol. Light brown oil, MS (ISP)=356.2 (M+H)$^+$.

Intermediate 17

2-Ethyl-3-oxo-4-(3-piperidin-1-yl-propyl)-piperazine-1-carboxylic acid tert-butyl ester a) 2-Ethyl-3-oxo-piperazine-1-carboxylic acid tert-butyl ester

The title compound was produced as described in intermediate 14a from 3-ethylpiperazin-2-one. Off-white solid, MS (ISP)=229.3 (M+H)$^+$.

b) 2-Ethyl-3-oxo-4-(3-piperidin-1-propyl)-piperazine-1-carboxylic acid tert-butyl ester Sodium hydride (55% dispersion in mineral oil, 46 mg, 1.05 mmol) was added at room temperature to a solution of 2-ethyl-3-oxo-piperazine-1-carboxylic acid tert-butyl ester (200 mg, 0.88 mmol) in N,N-dimethylacetamide (2 ml), then after 10 min a solution of 1-(3-chloropropyl)-piperidine [prepared from the commercially available hydrochloride salt (260 mg, 1.58 mmol) by basic extraction as described in intermediate 6] in toluene (2 ml) was added. The reaction mixture was stirred for 72 h at 40° C. then partitioned between water and ethyl acetate. The organic layer was washed with brine, dried (MgSO$_4$), and evaporated. Chromatography (SiO$_2$; CH$_2$Cl$_2$/MeOH/NH$_4$OH 95:5:0.25) afforded the title compound (148 mg, 48%). Colorless oil, MS (ISP)-354.3 (M+H)$^+$.

Intermediate 18

(R)-2-Methyl-5-oxo-4-(3-piperidin-1-yl-propyl)-piperazine-1-carboxylic acid tert-butyl ester a) 2-Bromo-N-but-3-enyl-acetamide

A solution of bromoacetyl bromide (5.21 g, 25.8 mmol) in dichloromethane (5 ml) was added dropwise at −78° C. to a solution of 3-butene-1-amine (2.00 g, 25.8 mmol) and triethylamine (2.56 g, 25.8 mmol) in dichloromethane (20 ml). After 10 min at −78° C., the reaction mixture was allowed to reach room temperature over 2 h, then washed with water. The organic layer was washed with brine, dried (MgSO$_4$), and evaporated to produce the title compound (4.59 g, 94%). Yellow liquid, $^1$H-NMR (300 MHz, CDCl$_3$): 6.53 (br. s, 1H), 5.85-5.7 (m, 1H), 5.2-5.1 (m, 2H), 3.89 (s, 2H), 3.38 (q, J=6.3, 2H), 2.31 (q, J=6.3, 2H).

b) But-3-enylcarbamoylmethyl-((R)-2-hydroxy-1-methyl-ethyl)-carbamic acid tert-butyl ester Potassium hydrogencarbonate (3.40 g, 34.0 mmol) was added to a solution of 2-bromo-N-but-3-enyl-acetamide (4.35 g, 22.7 mmol) and D-alaninol (1.74 g, 34.0 mmol) in acetonitrile (140 ml). The reaction mixture was stirred at room temperature for 72 h, then insoluble material was removed by filtration. The filtrate was evaporated and redissolved in dichloromethane (50 ml), then di-tert-butyl dicarbonate (4.95 g, 22.7 mmol) and triethylamine (2.29 g, 22.7 mmol) were added, and the solution was stirred at 50° C. for 20 h. After evaporation, the residue was purified by chromatography (SiO$_2$; heptane-ethyl acetate gradient) to afford the title compound (5.48 g, 80%). Colorless oil, MS (ISP)=287.3 (M+H)$^+$.

c) (R)-4-But-3-enyl-2-methyl-5-oxo-piperazine-1-carboxylic acid tert-butyl ester A solution of but-3-enylcarbamoylmethyl-((R)-2-hydroxy-1-methyl ethyl)-carbamic acid tert-butyl ester (4.26 g, 14.9 mmol) in tetrahydrofuran (200 ml) was added dropwise at <10° C. to a mixture of triphenylphosphine (5.07 g, 19.3 mmol) and diisopropyl azodicarboxylate (3.91 g, 19.3 mmol), then the reaction mixture was heated at 60° C. for 2 h. After cooling and evaporation of volatile material, the residue was chromatographed (SiO$_2$; heptane-ethyl acetate gradient) to afford the title compound (2.51 g, 63%). Yellow oil, MS (ISP)=269.3 (M+H)$^+$.

d) (R)-2-Methyl-5-oxo-4-(3-piperidin-1-yl-propyl)-piperazine-1-carboxylic acid tert-butyl ester The title compound was produced as described in intermediate 7b from (R)-4-but-3-enyl-2-methyl-5-oxo-piperazine-1-carboxylic acid tert-butyl ester and piperidine. Light brown oil, MS (ISP)=340.2 (M+H)$^+$.

Intermediate 19

(S)-2-Methyl-5-oxo-4-(3-piperidin-1-yl-propyl)-piperazine-1-carboxylic acid tert-butyl ester a) But-3-enylcarbamoylmethyl-((S)-2-hydroxy-1-methyl-ethyl)-carbamic acid tert-butyl ester The title compound was produced as described in intermediate 18b from 2-bromo-N-but-3-enyl-acetamide (intermediate 18a) and L-alaninol. Colorless oil, MS (ISP)=287.1 (M+H)$^+$.

b) (S)-4-But-3-enyl-2-methyl-5-oxo-piperazine-1-carboxylic acid tert-butyl ester The title compound was produced as described in intermediate 18c from but-3-enylcarbamoylmethyl-((S)-2-hydroxy-1-methyl-ethyl)-carbamic acid tert-butyl ester. Colorless oil, MS (ISP)=269.3 (M+H)$^+$.

c) (S)-2-Methyl-5-oxo-4-(3-piperidin-1-yl-propyl)-piperazine-1-carboxylic acid tert-butyl ester The title compound was produced as described in intermediate 7b from (S)-4-but-3-enyl-2-methyl-5-oxo-piperazine-1-carboxylic acid tert-butyl ester and piperidine. Light brown oil, MS (ISP)=340.2 (M+H)$^+$.

Intermediate 20

4-[(E)-3-(3,4-Dichloro-phenyl)-acryloyl]-3-methyl-1-pent-4-enyl-piperazin-2-one a) 2-Methyl-3-oxo-4-pent-4-enyl-piperazine-1-carboxylic acid tert-butyl ester The title compound was produced as described in intermediate 7a from 2-methyl-3-oxo-piperazine-1-carboxylic acid tert-butyl ester (intermediate 14a) and 5-bromo-1-pentene. Colorless oil, MS (ISP)=283.2 (M+H)$^+$.

b) 4-[(E)-3-(3,4-Dichloro-phenyl)-acryloyl]-3-methyl-1-pent-4-enyl-piperazin-2-one Hydrogen chloride solution (4 M in 1,4-dioxane, 8 ml) was added to a solution of 2-methyl-3-oxo-4-pent-4-enyl-piperazine-1-carboxylic acid tert-butyl ester (200 mg, 0.71 mmol). The reaction mixture was stirred at room temperature for 3.5 h, then volatile material was removed by rotary evaporation. The residue was taken up in dichlormethane (10 ml), treated with 4-methylmorpholine (358 mg, 3.54 mmol), and the mixture obtained concentrated in vacuo. The residue was taken up in N,N-dimethylformamide (8 ml), then 4-methylmorpholine (358 mg, 3.54 mmol), 3,4-dichlorocinnamic acid (161 mg, 0.71 mmol), and O-(7-azabenzotriazol-1-yl)-N,N,N',N'-tetramethyluronium hexafluoro-phosphate (404 mg, 1.06 mmol) were added. The solution was stirred at room temperature for 48 h, then the mixture was partitioned between water and ethyl acetate. The organic layer was washed with brine, dried (MgSO$_4$), and evaporated. Chromatography (SiO$_2$; heptane-ethyl acetate gradient) produced the title compound (233 mg, 86%). Light yellow oil, MS (ISP)=381.2 (M+H)$^+$.

Intermediate 21

3-Methyl-5-oxo-4-(3-piperidin-1-yl-propyl)-piperazine-1-carboxylic acid tert-butyl ester A solution of 1,2-diaminopropane (12.1 g, 163 mmol) in ethanol (20 ml) was added at room temperature over 90 min to a solution of ethyl chloroacetate (2.00 g, 16.3 mmol) in ethanol (70 ml), then after 2 h potassium carbonate (2.26 g, 16.3 mmol) was added. After another 2 h, insoluble material was removed by filtration, and the filtrate was evaporated. The residue was suspended in dichloromethane (50 ml) and treated with di-tert-butyl dicarbonate (24.9 g, 114 mmol), and the reaction mixture was stirred at room temperature for 16 h, then evaporated. The residue was chromatographed (SiO$_2$; heptane-ethyl acetate gradient) to afford 984 mg of a 3:2 mixture of the desired 3-methyl-5-oxo-piperazine-1-carboxylic acid tert-butyl ester and the regioisomer 3-methyl-5-oxo-piperazine-1-carboxylic acid tert-butyl ester. 200 mg of this regioisomeric mixture was alkylated with t-(3-chloropropyl)piperidine as described in intermediate 17b to produce the title compound (120 mg) containing 2-methyl-5-oxo-4-(3-piperidin-1-yl-propyl)-piperazine-1-carboxylic acid tert-butyl ester (ca. 20%) as a regioisomeric impurity. Light yellow oil, MS (ISP)=340.3 (M+H)$^+$.

Intermediate 22

2-Ethoxycarbonylmethyl-3-oxo-4-(3-piperidin-1-yl-propyl)-piperazine-1-carboxylic acid tert-butyl ester a) 2-Ethoxycarbonylmethyl-3-oxo-piperazine-1-carboxylic acid tert-butyl ester The title compound was produced as described in intermediate 14a from ethyl 2-(3-oxo-2-piperazinyl)acetate. Colorless oil, MS (ISP)=287.3 (M+H)$^+$.

b) 2-Ethoxycarbonylmethyl-3-oxo-4-(3-piperidin-1-yl-propyl)-piperazine-1-carboxylic acid tert-butyl ester The title compound was produced as described in intermediate t 7b from 2-ethoxycarbonylmethyl-3-oxo-piperazine-1-carboxylic acid tert-butyl ester and 1-(3-chloropropyl)-piperidine. Light yellow oil, MS (ISP)=412.4 (M+H)$^+$.

Intermediate 23

{2-[(E)-3-(3,4-Dichloro-phenyl)-acryloylamino]-ethyl}-carbamic acid tert-butyl ester The title compound was produced as described in intermediate 1 from 3,4-dichlorocinnamic acid and (2-amino-ethyl)-carbamic acid tert-butyl ester. White solid, MS (ISP)=359.1 (M+H)$^+$.

Intermediate 24

4-(2-Hydroxy-3-piperidin-1-yl-propyl)-3-oxo-piperazine-1-carboxylic acid tert-butyl ester Sodium hydride (55% dispersion in mineral oil; 92 mg, 2.1 mmol) was added at 0° C. to a solution of 3-oxo-piperazine- 1-carboxylic acid tert-butyl ester (300 mg, 1.50 mmol) in N,N-dimethylformamide (6 ml), then after 10 min a solution of epibromohydrin (254 mg, 1.80 mmol) in N,N-dimethylformamide (3 ml) was added. The reaction mixture was stirred for 3 h at 0° C., then poured onto ice and partitioned between ethyl acetate and sat. aq. sodium hydrogencarbonate solution. The organic layer was dried ($MgSO_4$) and evaporated. The residue was taken up in N,N-dimethylformamide (1 ml), then piperidine (191 mg, 2.25 mmol) and cesium carbonate (488 mg, 1.50 mmol) were added. The reaction mixture was stirred at room temperature for 16 h, then partitioned between water and ethyl acetate. The organic layer was dried ($MgSO_4$) and evaporated. Chromatography ($SiO_2$; $CH_2Cl_2$/MeOH/$NH_4OH$ 95:5:0.25) afforded the title compound (257 mg, 50%). Colorless oil, MS (ISP)=342.3 $(M+H)^+$.

Intermediate 25

(S)-6-Aza-spiro[2.5]octan-4-ol hydrochloride a) 4-Hydroxy-6-aza-spiro[2.5]octane-6-carboxylic acid tert-butyl ester Method A To a solution of diethylzinc (1.1 M solution in toluene, 37.5 ml, 0.04 mmol) in 1,2-dichloroethane (80 ml) at 0° C. was added chloroiodomethane (5.99 ml, 0.08 mmol) under Ar. This mixture was stirred for 15 minutes before a solution of 3-hydroxy-4-methylene-piperidine-1-carboxylic acid tert-butyl ester (*J. Org. Chem.* 2001, 66, 2487) (4.19 g, 19.6 mmol) in 1,2-dichloroethane (10 ml) was added, after which time the reaction was stirred for 0.5 h at 0° C. and then allowed to reach room temperature, stirring for a further 1 h. The reaction was then quenched by addition of saturated aq. ammonium chloride solution, separated, and the organic dried ($Na_2SO_4$) and concentrated. Purification by flash column chromatography (ethyl acetate/heptane 2:8-1:1) afforded the title product (2.4 g, 54%) as a crystalline solid MS: 228.2 ($MH^+$).

Method B g (9.4 mmol, 1 equiv.) 3-hydroxy-4-methylene-piperidine-1-carboxylic acid tert-butyl ester were dissolved in toluene at 25° C. 17.05 ml (2 equiv.) 1.1 M diethyl zinc solution in toluene were added at such a rate as to maintain the reaction temperature below 30° C. After 15-30 min at 25° C., 2.29 ml (3 equiv.) diiodomethane were added over 2-3 h maintaining the reaction temperature at 25° C. (the reaction is best followed by Tr-Tj measurements and/or in-line FTIR reaction monitoring). After 30-60 min after the end of addition, 4.57 ml 2-ethyl-hexanoic acid were added to the resulting white suspension at such a rate as to maintain the reaction temperature between 25-30° C. The heavy white suspension was stirred for 30 min. 10 ml heptane were added followed by a mixture consisting of 20 ml 25% aqueous ammonia solution and 30 ml water. The organic phase was separated and washed with a mixture consisting of 10 ml 25% aqueous ammonia solution and 30 ml water. The organic phases were washed with 20 ml half saturated aq. sodium chloride solution, combined, dried over sodium sulfate, filtered and concentrated under reduced pressure to an oil (may crystallize upon standing). The crude spiro-piperidinol was purified by crystallization in heptane or alternatively in tert-butyl methyl ether/heptane providing the title product in ca 80% yield as a white powder.

b) (S)-4-Hydroxy-6-aza-spiro[2.5]octane-6-carboxylic acid tert-butyl ester

Method A

The title compound was prepared by chiral separation of (rac)-4-hydroxy-6-aza-spiro[2.5]octane-6-carboxylic acid tert-butyl ester on a Chiralpak® AD column (heptane/2-propanol 95:5).

Method B

—Hydroxy-6-aza-spiro[2.5]octane-6-carboxylic acid tert-butyl ester (3.00 g; 13.07 mmol) was dissolved in tert-butyl methyl ether (20.5 ml) and vinyl butyrate (6.5 ml). The solution was heated to 50° C. and the reaction started by the addition of Lipase TL (3.0 g; Meito Sangyo, Tokyo). The solution was stirred at 50° C. for 46 h until the enantiomeric excess of the retained alcohol was >99%. The enzyme was filtered off, the filter cake washed with tert-butyl methyl ether and the filtrate concentrated in vacuo. The residual oil was chromatographed on silica gel (80 g; 0.040-0.063 mm; dichloromethane→dichloromethane/acetone 9:1) to separate the formed optically enriched (R)-butyrate from the retained (S)-alcohol (1.18 g white crystals; 40%). Analytics: >99 GC; >99% ee (GC on BGB-176; 30 m×0.25 mm; $H_2$; 1.2 bar; 80° C. to 210° C. with 3° C./min; inj. 200° C.; Det. 215° C.; Retention times: (R)-alcohol 28.58 min, (S)-alcohol 29.00 min). $[\alpha]_D$=−43.35° (c=1.00, $CHCl_3$).

Method C

Step 1: 4-Oxo-6-aza-spiro[2,5]octane-6-carboxylic acid tert-butyl ester

The title compound was produced from 4-hydroxy-6-aza-spiro[2.5]octane-6-carboxylic acid tert-butyl ester, either by TEMPO/bleach oxidation or by Swern oxidation:

a) TEMPO/Bleach Oxidation

To a solution of 4-hydroxy-6-aza-spiro[2.5]octane-6-carboxylic acid tert-butyl ester (20.0 g, 88.0 mmol) in dichloromethane (170 ml) was added sodium bromide (1.092 g, 10.6 mmol), sodium bicarbonate (2.439 g, 29.0 mmol) and 2,2,6,6-tetramethylpiperidine 1-oxyl (237.1 mg, 1.49 mmol). The mixture was cooled to −5° C. and sodium hypochlorite solution (9.5% in water, 55.16 ml) was added within 10 min resulting in a red coloration and a temperature rise to 9° C. The mixture was stirred for 35 min at 0-5° C. and, as conversion was incomplete (2.5% starting material remaining), additional sodium hypochlorite solution (9.5% in water, 7.0 ml) was added within 30 min and the mixture stirred for another 30 min at 0° C. GC analysis indicated complete conversion (<0.1% starting material remaining). Sodium thiosulfate solution (10% in water, 100 ml) was added within 10 min resulting in decoloration. The organic phase was separated, washed with water (100 ml), dried over sodium sulfate (50 g), filtered and evaporated (15 mbar, 40° C.) to afford 4-oxo-6-aza-spiro[2.5]octane-6-carboxylic acid tert-butyl ester as yellowish powder (19.84 g), GC purity 99a %. The powder was dissolved in warm tert-butyl methyl ether (20 ml), heptane (60 ml) was added to induce crystallization and the white suspension stirred at 0-5° C. for 1.5 h. Filtration, washing with heptane (20 ml) and drying (10 mbar, 45° C.) afforded 4-oxo-6-aza-spiro[2.5]octane-6-carboxylic acid tert-butyl ester (17.25 g, 87%) as white crystalline material, GC purity 100a %. $^1$H-NMR ($CDCl_3$, 300 MHz): 4.08 (s, $CH_2(5)$), 3.66 (m, $CH_2(7)$), 1.88 (m, $CH_2(8)$), 1.48 (s, tert-Bu), 1.40 (m, 2H), 0.81 (m, 2H).

b) Swern Oxidation

To a solution of oxalyl chloride (42.35 ml, 0.480 mol) in dichloromethane (910 ml) was added a solution of dimethyl-sulfoxide (68.24 ml, 0.961 mol) in dichloromethane (910 ml) at −70° C. within 45 min. The solution was stirred for 15 min and a solution of 4-hydroxy-6-aza-spiro[2,5]octane-6-carboxylic acid tert-butyl ester (91.00 g, 0.400 mol) in dichloromethane (910 ml) was added within 40 min keeping the internal temperature at below −60°. The mixture was stirred for 35 min and triethylamine (280.4 ml, 2.00 mol) was added at below −60° C. within 10 min. The cooling bath was removed and the yellow suspension was stirred for 1 h then quenched with water (1.4 l). The organic phase was separated, washed with water (3×1 l) and sat. aq. sodium chloride solution (3 l) and evaporated. The residual orange powder was dissolved in tert-butyl methyl ether (1.40 l), the turbid solution filtered (Hyflo Speedex) to remove some insoluble material and the clear filtrate evaporated to provide crude 4-oxo-6-aza-spiro[2.5]octane-6-carboxylic acid tert-butyl ester as yellow powder (91.9 g). The material was re-dissolved in tert-butyl methyl ether (300 ml) and purified by filtration over silica gel (700 g) using a 3:1 heptane/tert-butyl methyl ether mixture (6.5 l). Evaporation and drying (10 mbar, 40° C.) afforded 4-oxo-6-aza-spiro[2.5]octane-6-carboxylic acid tert-butyl ester as whitish powder (80.58 g, 89%), CC purity 100a %.

Step 2:
(S)-4-Hydroxy-6-aza-spiro[2.5]octane-6-carboxylic acid tert-butyl ester

D(+)-glucose monoydrate (300 g) and magnesium chloride hexahydrate (1.0 g) were dissolved in 10 mM MES buffer pH 6.5 (2.4 L; Sigma M3671). After addition of 4-oxo-6-aza-spiro[2.5]octane-6-carboxylic acid tert-butyl ester (300 g; 1.33 mmol) and β-NAD (3.0 g; free acid; Roche Diagnostics Cat. No. 10 004 626) the pH was re-adjusted and the suspension heated to 35° C. The reaction was started by adding ketoreductase KRED-NADH-117 (3.0 g; former Biocatalytics, now Codexis) and glucose dehydrogenase GDH-102 (300 mg; Biocatalytics). The suspension was vigorously stirred at 35° C. keeping the pH constant at 6.5 by the controlled addition (pH-stat) of 1.0 M aq. sodium hydroxide solution. After a consumption of 1.307 L (corresponding to 98% conversion; after 17 h) the reaction mixture was extracted with ethyl acetate (10 L). The organic phase was dried over sodium sulfate and concentrated in vacuo (200 mbar/45° C.) until evaporation fell off. Upon cooling the oily residue (411 g) started to crystallize and was stirred with heptane (1 L) for 2 h. The crystals were filtered off and the filtrate evaporated to dryness, redissolved in ethyl acetate (150 ml) and concentrated in vacuo as described above. The crystal suspension formed again upon cooling was stirred with heptane (200 ml; 2 h) and the crystals filtered off. Both crops of crystals were washed with heptane and dried under high vacuum to yield the title compound in 93% yield (250.77 g and 34.60 g white crystals), each having a purity of >98.5% GC and 99.8% ee. $[\alpha]_D = -44.97°$ (C=1.00, CHCl$_3$).
Method D Step 1:
(S)-3-hydroxy-4-methylene-piperidine-1-carboxylic acid tert-butyl ester 3-Hydroxy-4-methylene-piperidine-1-carboxylic acid tert-butyl ester (4.50 g, 21.10 mmol) was dissolved in tert-butyl methyl ether (63 ml) and vinyl butyrate (22.5 ml). The solution was heated to 50° C. and the reaction started by the addition of Lipase TL IM (1.08 g (carrier-fixed); Novozymes, Denmark). The solution was stirred at 50° C. for 20 h until the enantiomeric excess of the retained alcohol was >99%. The enzyme was filtered off, the filter cake washed with tert-butyl methyl ether and the filtrate concentrated in vacuo. The residual oil was chromatographed on silica gel (100 g; 0.040-0.063 mm; dichloromethane→dichloromethane/acetone 9:1) to separate the formed optically enriched (R)-butyrate from the retained (S)-alcohol (1.83 g white crystals; 41%). Analytics: >99 GC; >99% ee (GC on BGB-176; 30 m×0.25 mm; H$_2$; 1.2 bar; 80° C. to 210° C. with 3° C./min; inj. 200° C.; Det. 210° C.; retention times: (R)-alcohol 29.60 min, (S)-alcohol 29.81 min). $[\alpha]_D = -17.70°$ (c=1.00, CHCl$_3$).

Step 2:
(S)-4-Hydroxy-6-aza-spiro[2.5]octane-6-carboxylic acid tert-butyl ester

The title compound is produced analogously to intermediate 25a, Method B from (S)-3-hydroxy-4-methylene-piperidine-1-carboxylic acid tert-butyl ester.

c) (S)-6-Aza-spiro[2.5]octan-4-ol hydrochloride

A solution of (S)-4-hydroxy-6-aza-spiro[2.5]octane-6-carboxylic acid tert-butyl ester (3.26 g, 14.3 mmol) in ethanol (10 ml) was treated at room temperature with hydrogen chloride solution (4 M in 1,4-dioxane, 30 ml), then after 1 h tert-butyl methyl ether (40 ml) was added. The suspension was stirred for 1 h, then the precipitate was collected by filtration to afford the title compound (2.11 g, 90%). White solid, MS: 128.1 (M+H)$^+$.

Alternative preparation of
(S)-6-Aza-spiro[2.5]octan-4-ol hydrochloride i) Cyclopropanecarboxylic acid tert-butyl ester 219.1 g (1913 mmol, 1 equiv.) potassium tert-butylate were suspended in 2.5 L tert-butyl methyl ether and cooled to 0-5° C. 200 g (1 equiv.) cyclopropanecarbonyl chloride were added over 60 min, maintaining the temperature between 0-5° C. (ice-ethanol bath cooling). In-line FTIR reaction monitoring indicates a feed controlled reaction. The reaction mixture was stirred 30 min at 0-5° C. and 1 L of 5% aqueous sodium hydrogencarbonate solution was added. The aqueous phase was separated and extracted with 500 ml tert-butyl methyl ether. The organic phases were washed with 500 ml half saturated aq. sodium chloride solution, combined and concentrated under reduced pressure (30° C./150 mbar) to provide 271 g of the title compound (91% yield corrected for 8% residual tert-butyl methyl ether).

ii) 1-Allyl-cyclopropanecarboxylic acid tert-butyl ester 15.9 ml (1.15 equiv.) diisopropylamine were dissolved in 65 ml tetrahydrofuran and cooled to ca −10° C. 65 ml (1.08 equiv.) 1.6 M butyllithium solution in hexane were added over 25 min, maintaining the temperature between −10° C. and 0° C. After 50 nm in at ca. −5° C., the reaction mixture was cooled to −75° C. A solution of 15 g (96.7 mmol, 1 equiv., 92% w/w purity) cyclopropanecarboxylic acid tert-butyl ester in 20 ml tetrahydrofuran was added over 15 min keeping the temperature between −75° C. and −70° C. The reaction mixture was stirred 5 h at −75° C. (milky reaction mixture obtained after 2.5 h). A solution of 12.87 g (1.10 equiv.) allyl bromide was added over 20 min keeping the temperature between −75° C. and −60° C. The reaction mixture was stirred at −78° C. for 1 h, warmed to room temperature and stirred overnight. The reaction mixture was cooled to 0° C. 100 ml sat. aq. ammonium chloride solution were added followed by 30 ml water providing a clear biphasic mixture. The mixture was extracted 3 times with 50 ml tert-butyl methyl ether. The organic phases were combined, dried over sodium sulfate, filtered and concentrated under reduced pressure (40° C./20 mbar) to afford 16.44 g of crude product. The crude product was distilled (2 mbar; ca 40° C. distillation head temperature) to provide the title compound in ca 65% yield.

iii) 1-(2-Oxo-ethyl)-cyclopropanecarboxylic acid tert-butyl ester 6.9 g (36.34 mmol, 1 equiv., 96% a % by GC) 1-allyl-cyclopropanecarboxylic acid tert-butyl ester were dissolved in 40 ml dichloromethane and 40 ml methanol. The solution was cooled to −72° C. and the ozone was bubbled through the reaction mixture until a blue color was obtained. Then nitrogen was bubbled to remove excess ozone until a colorless solution was obtained. 10 ml (3.68 equiv.) dimethyl sulfide and 14 ml (2.76 equiv.) triethylamine were added. The reaction mixture was warmed to room temperature and stirred overnight at that temperature (peroxide test negative, pH 7-8). The yellowish reaction mixture was added to 100 ml sat aq. ammonium chloride solution (exothermic) and extracted 3 times with 70 ml dichloromethane. The organic phases were combined, dried over sodium sulfate, filtered and concentrated under reduced pressure to provide the crude aldehyde, which was purified by filtration over $SiO_2$ (dichloromethane; TLC: ethyl acetate/heptane 1:2) to provide 3.90 g (96% GC, 56% yield) of the title compound as an oil.

iv) 1-[2-(Benzyl-tert-butoxycarbonylmethyl-amino)-ethyl]-cyclopropanecarboxylic acid tert-butyl ester 10.5 g (54.7 mmol, 1 equiv.) 1-(2-oxo-ethyl)-cyclopropanecarboxylic acid tert-butyl ester and 13.21 g (1.08 equiv.) N-benzylglycine tert-butyl ester were dissolved in 140 ml toluene. 21 g (1.63 equiv.) sodium triacetoxyborohydride were added (exotherm from 25° C. to 28° C.) and the reaction mixture was stirred 5 h at room temperature (IPC by GC). A solution of 2 ml (0.64 equiv.) acetic acid in 15 ml toluene was added. After 30 min at room temperature, the reaction mixture was cooled to 0° C. and 100 ml sat. aq. sodium hydrogencarbonate solution was added over 40 min (foaming). 50 ml ethyl acetate were added. The mixture was stirred for 30 min at room temperature. The mixture was extracted with 200 ml and a second time with 50 ml ethyl acetate. The organic phases were washed with 50 ml sat. aq. sodium hydrogencarbonate solution followed by 50 ml sat. aq. sodium chloride solution. The organic phases were combined, dried over sodium sulfate, filtered and concentrated under reduced pressure to give 21.5 g of the title compound as an oil (ca. 95% yield, corrected for ca 3% residual toluene and 3% amine starting material).

v) 6-Benzyl-6-aza-spiro[2.5]octan-4-one hydrochloride 10.8 g (24.4 mmol, 1 equiv.) 1-[2-(benzyl-tert-butoxycarbonylmethyl-amino)-ethyl]-cyclopropanecarboxylic acid tert-butyl ester were dissolved in 35 ml tetrahydrofuran. 50 ml (2.05 equiv.) 1 M lithium hexamethyldisilazanide solution in tetrahydrofuran were added dropwise over 2.5 h maintaining the temperature between 20° C. and 25° C. After 2 h at room temperature (IPC by HPLC), the reaction mixture (containing the lithium salt of 6-benzyl-4-hydroxy-6-aza-spiro[2.5]oct-4-ene-5-carboxylic acid tert-butyl ester) was cooled to −10° C. (ice ethanol cooling bath) and 75 ml 1 M aq. sulfuric acid solution were added (temperature increased to 2° C.). The reaction mixture was warmed to room temperature and the tetrahydrofuran removed under reduced pressure at 40° C. The resulting reaction mixture was heated to 40° C. for 1 h, was stirred 15 h at room temperature and an additional 3 h at 40° C. to complete the reaction (IPC by GC; intermediate 6-benzyl-4-hydroxy-6-aza-spiro[2.5]oct-4-ene-5-carboxylic acid tert-butyl ester is hydrolyzed and decarboxylation follows). The reaction mixture was cooled to 0° C. and was neutralized to pH 7.4 by addition of 10 ml 2 M aq. sodium hydroxide solution and 50 ml 1M aq. sodium hydrogencarbonate solution were added, setting the pH to 9.4. The crude solution was extracted with tert-butyl methyl ether and ethyl acetate. The organic phases were combined, dried over sodium sulfate and filtered over a plug of $SiO_2$. The solution was concentrated under reduced pressure (45° C./20 mbar) to give 4.56 g of the crude product as free base. The crude oil was dissolved in 8 ml ethyl acetate, cooled to 0° C. and 5.1 ml hydrogen chloride solution (4.3 M in ethyl acetate) were added dropwise (exotherm 2° C. to 18° C.). The reaction mixture was stirred overnight at room temperature (gummy crystals) and filtered. The filter cake was washed with 10 ml ethyl acetate and dried under reduced pressure until constant weight to give 4.54 g of the title compound as off-white crystals (74% yield).

vi) (S)-6-Benzyl-6-aza-spiro[2.5]octan-4-ol

A mixture of 300 mg of 6-benzyl-6-aza-spiro[2.5]octan-4-one hydrochloride (1.19 mmol, 1 equiv.), 1.5 ml of 2-propanol and 28 ml of 30 mM aq. TRIS-HCl buffer (pH 8.1) was heated to 35° C. The pH was re-adjusted to 8.0. The reaction was started by adding β-NAD (1 mg; free acid; Roche Diagnostics Cat. No. 10 004 626) and ketoreductase KRED-NADH-117 (29.3 mg; Codexis [ex. Biocatalytics]). The suspension was stirred at 35° C. keeping the pH constant at 8.0 by the controlled addition (pH-stat) of 1.0 M aq. sodium hydroxide solution. After roughly 80 area % conversion and 1 d, further 2-propanol (0.3 ml), β-NAD (3 mg; free acid; Roche Diagnostics Cat. No. 10 004 626), ketoreductase K RED-NADH-117 (30 mg; Codexis [ex. Biocatalytics]) and magnesium chloride (12.7 mg) were added. After 4 d, 98.5 area % conversion and 5.9 ml consumption of 1.0 M aq. sodium hydroxide solution the reaction mixture was stopped by the addition of sodium chloride (9 g), ethyl acetate (30 ml) and filter aid (1 g Dicalite Speedex). The mixture was stirred 30 min. and filtered. The filtrate was extracted 3 times with 30 ml ethyl acetate. The combined organic phases were dried over sodium sulfate, filtered and concentrated under reduced pressure to provide the crude product in over 99.9% e.e. Purification by flash chromatography provided the title compound as a colorless oil.

vii) (S)-6-Aza-spiro[2.5]octan-4-ol 100 mg (S)-6-benzyl-6-aza-spiro[2.5]octan-4-ol were dissolved in 1 ml methanol and hydrogenated over palladium on barium sulfate. After de-benzylation (IPC by GC), the catalyst was filtered and the filtrate was concentrated under reduced pressure to provide the title compound. The hydrochloride salt of the title compound can be obtained by treating the aminoalcohol with HCl in ethyl acetate.

The title compound was treated with di-tert-butyl-dicarbonate in methanol in the presence of triethylamine. The crude tert-butoxycarbonyl-protected amine product was analyzed by chiral GC (BGB-176; 30 m×0.25 mm; 80° C. to 210° C. in 43 min) and proved to be identical with intermediate 25b.

Preparation of N-benzylglycine tert-butyl ester 40 g (205 mmol, 1 equiv.) tert-butyl bromoacetate were dissolved in 200 ml acetonitrile. The solution was cooled to 0-5° C. and 47 g benzylamine (2.14 equiv.) in solution in 90 ml acetonitrile were added over 15 min. After 5 min, the reaction mixture was warmed to room temperature and stirred for 3 h (IPC by GC). The resulting suspension was filtered and evaporated to constant weight to give 49 g of a yellow oil. The oil was dissolved in 200 ml heptane and washed 3 times with 50 ml aq. sodium hydrogencarbonate solution. The organic phase was dried over sodium sulfate, filtered and evaporated to give 35.8 g of the crude product. Distillation under high vacuum afforded 27.2 g of the title product (95% pure by GC).

Intermediate 26

(3S,4S)-4-Methyl-piperidin-3-ol hydrochloride a) (rac,trans)-3-Hydroxy-4-methyl-piperidine-1-carboxylic acid tert-butyl ester (rac,trans)-1-Benzyl-4-methyl-piperidin-3-ol (*Tetrahedron. Lett.* 2000, 41, 5817) (13.0 g, 63 mmol) was dissolved in methanol with palladium hydroxide (20% on activated charcoal, 4 g) and stirred under a hydrogen atmosphere (balloon) for 16 h after which time di-tert-butyl dicarbonate (13.8 g, 63 mmol) was added, the reaction stirred for 1 h, filtered through Hyflo and concentrated to afford the title product (13.3 g, 98%) as a crystalline solid. MS: 216.2 (MH$^+$).

b) (rac,trans)-4-Methyl-3-(4-nitro-benzoyloxy)-piperidine-1-carboxylic acid tert-butyl ester (rac,trans)-3-Hydroxy-4-methyl-piperidine-1-carboxylic acid tert-butyl ester (6.0 g, 28 mmol) was dissolved in tetrahydrofuran (40 ml) with triphenylphosphine (8.9 g, 34 mmol), 4-nitrobenzoic acid (5.7 g, 34 mmol) and cooled to 0° C. before dropwise addition of diisopropyl azodicarboxylate (6.9 g, 34 mmol). The ice bath was removed and the reaction allowed to come to room temperature, stirring for 16 h. The reaction was then directly absorbed onto silica gel and purified by flash column chromatography (ethyl acetate/heptane 2:8) to afford the title product (4.0 g, 40%) as a white solid. MS: 365.2 (MH$^+$).

c) (rac,cis)-3-Hydroxy-4-methyl-piperidine-1-carboxylic acid tert-butyl ester (rac,trans)-4-Methyl-3-(4-nitro benzoyloxy)-piperidine-1-carboxylic acid tert-butyl ester (5.0 g, 14 mmol) was dissolved in methanol (70 ml) and 6 M. aq. sodium hydroxide solution (4.5 ml, 27 mmol) was added. The reaction was stirred for 1 h after which time the solvent removed under vacuum, the residue portioned between water and dichloromethane and the organic collected, dried (Na$_2$SO$_4$) and concentrated to afford the title product (2.6 g, 87%) as a crystalline solid. MS: 216.1 (MH$^+$).

d) (3S,4S)-4-Methyl-piperidin-3-ol hydrochloride (rac,cis)-3-Hydroxy-4-methyl-piperidine-1-carboxylic acid tert-butyl ester was separated on a Chiralpak AD column (Isopropanol/Heptane 5:95) and subsequently, the (−)-enantiomer was deprotected with HCl in dioxane to afford the title compound as a white powder. MS: 116.2 (MH$^+$).

Intermediate 27

(3S,5S)-5-Methyl-piperidin-3-ol hydrochloride a) (S)-3-(Benzyl-ethoxycarbonylmethyl-amino)-butyric acid ethyl ester To ethanol (55 ml) cooled to 0° C. was added acetyl bromide (41 ml, 0.6 mol) dropwise, followed by a solution of (S)-4-methyl-dihydro-furan-2-one (*Tetrahedron* 1983, 39, 3107; 18.6 g, 0.2 mol) in ethanol (20 ml). The ice bath was removed and the reaction allowed to reach room temperature. After 2 h of stirring the reaction was concentrated, the residue redissolved in dichloromethane, washed with saturated aq. sodium hydrogencarbonate solution, dried (Na$_2$SO$_4$) and concentrated affording (S)-4-bromo-3-methyl-butyric acid ethyl ester (33.6 g, quant). This was redissolved in ethanol (100 ml), cooled to 0° C. and N-benzylglycine ethyl ester (28.2 g, 0.14 mol) and triethylamine (22.4 ml, 0.16 mmol) were added. The reaction was then warmed to 75° C. for 4 d after which time the reaction was concentrated, the residue redissolved in dichloromethane, washed with saturated aq. sodium hydrogencarbonate solution, dried (Na$_2$SO$_4$) and concentrated. Purification by flash column chromatography (ethyl acetate/heptane 5:95) afforded the titled product as a light gold oil (20.3 g, 43%). MS (ISP)=322.2 (M+H)$^+$.

b) (S)-1-Benzyl-5-methyl-piperidin-3-one

To a suspension of sodium hydride (55% dispersion in mineral oil, 6.4 g, 14 mmol) in toluene (90 ml) was added (S)-3-(benzyl-ethoxycarbonylmethyl-amino)-butic acid ethyl ester (20.3 g, 0.06 mol) in toluene (10 ml), followed by ethanol (1 ml). A vigorous reaction ensued, after 15 minutes the reaction was diluted with ethyl acetate, washed with 10% aq. citric acid solution, dried (Na$_2$SO$_4$) and concentrated. The residue was purified by flash column chromatography (ethyl acetate/heptane 1:9) affording a complex mixture of diastereomers (7.2 g, 42%). A portion of this material (3.5 g, 13 mmol) was dissolved in 25% aq. hydrochloric acid solution (20 ml) and heated in a loosely closed tube at 120° C. for 36 h. The solvent Divas evaporated, the residue redissolved in dichloromethane, washed with saturated aq. sodium hydrogencarbonate solution, dried (Na$_2$SO$_4$) and concentrated. Purification by flash column chromatography (ethyl acetate/heptane 1:4) afforded the titled product as a crystalline solid (1.1 g, 43%). MS (ISP)=204.3 (M+H)$^+$.

c) (3S,5S)-1-Benzyl-5-methyl-piperidin-3-ol

To a solution of (S)-benzyl-5-methyl-piperidin-3-one (1.1 g, 5 mmol) in dry tetrahydrofuran (15 ml) at −78° C. was added K-selectride (10.8 ml, 11 mmol, 1 M solution in tetrahydrofuran). After 2 h at −78° C. a few drops of water were cautiously added, the reaction allowed to reach room temperature, the tetrahydrofuran removed by evaporation and the residue the residue redissolved in dichloromethane, washed with saturated aq. sodium hydrogencarbonate solution, dried (Na$_2$SO$_4$) and concentrated. Purification by flash column chromatography (ethyl acetate/heptane 1:4) afforded the titled product as a crystalline solid (0.9 g, 43%). MS (ISP)-204.3 (M+H)$^+$.

d) (3S,5S)-5-Methyl-piperidin-3-ol hydrochloride

To a solution of (S)-1-benzyl-5-methyl-piperidin-3-one (0.9 g, 4 mmol) was dissolved in methanol, 25% aq, hydrochloric acid solution added until the pH was acidic, followed by palladium (10% on activated charcoal, 0.2 g). The mixture was stirred under 1 atmosphere of hydrogen (balloon) for 6 h. The reaction was then filtered through Hyflo and concentrated to afford the title product as a white powder (0.66 g, quant). MS (ISP)=116.1 (M+H)$^+$.

Intermediate 28

(S)-4-[(B)-3-(3-Chloro-4-fluoro-phenyl)-acryloyl]-1-(3-hydroxy-propyl)-3-methyl-piperazin-2-one a) 2-(3-Benzyloxy-propylamino)-ethanol Sodium iodide (1.67 g, 11.1 mmol) was added to a solution of benzyl 3-bromopropyl ether (26.0 g, 111 mmol) and ethanolamine (35.0 g, 556 mmol) in ethanol (250 ml). The reaction mixture was heated at reflux for 1 h, then cooled to room temperature and evaporated under vacuum. The residue was partitioned between sat. aq. ammonium chloride solution and ethyl acetate. The aqueous layer was basified with 40% aq. sodium hydroxide solution and extracted three times with ethyl acetate. The organic phases were pooled, dried (MgSO$_4$), filtered, and evaporated to afford the title compound (20.9 g, 90%). Light yellow liquid, MS (ISP)=210.2 (M+H)$^+$.

b) {(S)-1-[(3-Benzyloxy-propyl)(2-hydroxy-ethyl)-carbamoyl]-ethyl}-carbamic acid tert-butyl ester A solution of N-(tert-butoxycarbonyl)-L-alanine (90 mg, 0.48 mmol), 2-(3-benzyloxy-propylamino)-ethanol (100 mg, 0.48 mg), N,N-diisopropylethylamine (185 mg, 1.43 mmol), 1-hydroxybenzotriazole (71 mg, 0.52 mmol), and N-ethyl-N'-(3-dimethylaminopropyl)carbodiimide hydrochloride (101 mg, 0.52 mmol) in N,N-dimethylformamide (2 ml) was stirred at room temperature for 18 h, then partitioned between 1 M aq. hydrochloric acid solution and ethyl acetate. The organic layer was dried (MgSO$_4$), filtered, and evaporated. Chromatography (SiO$_2$; heptane-ethyl acetate gradient) produced the title compound (121 mg, 67%). Colorless oil, MS (ISP)=381.4 (M+H)$^+$.

c) (S)-1-(3-Benzyloxy-propyl)-3-methyl-piperazin-2-one

Dimethyl sulfoxide (7.60 g, 97.2 mmol) was added dropwise at −78° C. to a solution of oxalyl chloride (6.17 g, 48.6 mmol) in dichloromethane (300 ml) then after 10 min a solution of {(S)-1-[(3-benzyloxy-propyl)-(2-hydroxy-ethyl)-carbamoyl]-ethyl}-carbamic acid tert-butyl ester (16.8 g, 44.2 mmol) in dichloromethane (300 ml) was added at a temperature below −70° C. After 1 h, triethylamine (16.1 g, 159 mmol) was added, then after 15 min the ice bath was removed. The reaction mixture was allowed to reach room temperature, then washed with sat. aq. sodium hydrogencarbonate solution and brine, dried (MgSO$_4$), filtered, and evaporated. The residue was taken up in dichloromethane (300 ml), then triethylsilane (10.3 g, 88.4 mmol) and trifluoroacetic acid (75.6 g, 663 mmol) were added at room temperature. The reaction mixture was stirred at room temperature for 16 h, then evaporated. The residue wads dissolved in dichloromethane (100 ml), then triethylamine (60 ml) was added at 0° C. over 30 min, then after 45 min the reaction mixture was concentrated. The residue was dissolved in ethyl acetate and water, then 2 M aq. sodium carbonate solution was added under ice cooling. The organic layer was separated, washed with brine, dried (MgSO$_4$), filtered, and evaporated. Chromatography (SiO$_2$; CH$_2$Cl$_2$/MeOH/NH$_4$OH 90:10:0.25) produced the title compound (9.07 g, 78%). Colorless oil, MS (ISP)=263.4 (M+H)$^+$.

d) (S)-1-(3-Hydroxy-propyl)-3-methyl-piperazin-2-one

A solution of (S)-1-(3-benzyloxy-propyl)-3-methyl-piperazin-2-one (9.07 g, 34.6 mmol) in methanol only heated for 14 h at 70° C. under a hydrogen atmosphere (7 bar) in the presence of palladium (10% on activated charcoal, 7.36 g). After cooling, insoluble material was removed by filtration and the filtrate evaporated to produce the title compound (5.90 g, 99%). Colorless oil, MS (ISP)=173.1 (M+H)$^+$.

e) (S)-4-[(E)-3-(3-Chloro-4-fluoro-phenyl)-acryloyl]-1-(3-hydroxy-propyl)-3-methyl-piperazin-2-one A solution of 3-chloro-4-fluorocinnamic acid (4.52 g, 21.9 mmol), (S)-1-(3-hydroxy-propyl)-3-methyl-piperazin-2-one (3.76 g, 21.9 mmol), N,N-diisopropylethylamine (8.46 g, 65.5 mmol), 1-hydroxybenzotriazole (3.25 g, 24.0 mmol), and N-ethyl-N'-(3-dimethylaminopropyl)carbodiimide hydrochloride (4.60 g, 24.0 mmol) in N,N-dimethylformamide (80 ml) was stirred at room temperature for 18 h, then partitioned between 1 M aq. hydrochloric acid solution and ethyl acetate. The organic layer was washed with 1 M aq. hydrochloric acid solution, sat. aq. sodium hydrogencarbonate solution, and brine, dried (MgSO$_4$), filtered, and evaporated. Chromatography (SiO$_2$; CH$_2$Cl$_2$/MeOH/NH$_4$OH 90:10:0.25) produced the title compound (6.54 g, 84%). Colorless gum, MS (ISP)=355.2 (M+H)$^+$.

Intermediate 29

(S)-4-[(E)-3-(3-Chloro-phenyl)-acryloyl]-1-(3-hydroxy-propyl)-3-methyl-piperazin-2-one The title compound was produced analogously to intermediate 28e from 3-chlorocinnamic acid and (S)-1-(3-hydroxy-propyl)-3-methyl-piperazin-2-one (intermediate 28d). Colorless gum, MS (ISP)=337.3 (M+H)$^+$.

Intermediate 30

(R)-4-[(E)-3-(3-Chloro-4-fluoro-phenyl)-acryloyl]-1-(3-hydroxy-propyl)-3-methyl-piperazin-2-one a) {(R)-1-[(3-Benzyloxy-propyl)-(2-hydroxy-ethyl)-carbamoyl]-ethyl}-carbamic acid tert-butyl ester The title compound was produced analogously to intermediate 28b from N-(tert-butoxycarbonyl)-D-alanine and 2-(3-benzyloxy-propylamino)-ethanol (intermediate 28, step a). Colorless oil, MS (ISP)=381.4 (M+H)$^+$.

b) (R)-1-(3-Benzyloxy-propyl)-3-methyl-piperazin-2-one

The title compound was produced analogously to intermediate 28c from {(R)-1-[(3-benzyloxy-propyl)-(2-hydroxyethyl)-carbamoyl]-ethyl}-carbamic acid tert-butyl ester. Colorless oil, MS (ISP)=263.1 (M+H)⁺.

c) (R)-1-(3-Hydroxy-propyl)-3-methyl-piperazin-2-one

The title compound was produced analogously to intermediate 28d from (R)-1-(3-benzyloxy-propyl)-3-methyl-piperazin-2-one. Colorless oil, MS (ISP)=173.1 (M+H)⁺.

d) (R)-4-[(E)-3-(3-Chloro-4-fluoro-phenyl)-acryloyl]-1-(3-hydroxy-propyl)-3-methyl-piperazin-2-one The title compound was produced analogously to intermediate 28, step e from 3-chloro-4-fluorocinnamic acid and (R)-1-(3-hydroxy-propyl)-3-methyl-piperazin-2-one. Colorless gum, MS (ISP)=355.2 (M+H)⁺.

Intermediate 31

(R)-2-Methyl-3-oxo-4-(3-piperidin-1-yl-propyl)-piperazine-1-carboxylic acid tert-butyl ester a) 2-But-3-enylamino-ethanol

The title compound was produced analogously to intermediate 28a from ethanolamine and 4-bromo-but-1-ene. Colorless liquid, ¹H-NMR (300 MHz, CDCl₃): 5.85-5.7 (m, 1H), 5.15-5.0 (m, 2H), 3.65-3.6 (m, 2H), 2.8-2.75 (m, 2H), 2.71 (t, J=6.6, 2H), 2.3-2.2 (m, 2H), 1.92 (br. s, 2H).

b) {(R)-1-[But-3-enyl-(2-hydroxy-ethyl)-carbamoyl]-ethyl}-carbamic acid tert-butyl ester The title compound was produced analogously to intermediate 28b from N-(tert-butoxycarbonyl)-D-alanine and 2-but-3-enylamino-ethanol. Colorless oil, MS (ISP)=287.3 (M+H)⁺.

c) (R)-1-But-3-enyl-3-methyl-piperazin-2-one

A solution of {(R)-1-[but-3-enyl-(2-hydroxy-ethyl)-carbamoyl]-ethyl}-carbamic acid tert-butyl ester (750 mg, 2.62 mmol) in 1,4-dioxane (8 ml) was treated with hydrogen chloride solution (4 M in 1,4-dioxane, 13 ml). The reaction mixture was stirred for 90 min at room temperature, then concentrated in vacuo. The residue was taken up in tetrahydrofuran (15 ml, then triethylamine (1.33 g, 13.1 mmol) was added, and the reaction mixture was concentrated. The residue was suspended in tetrahydrofuran and treated with triphenylphosphine (824 mg, 3.14 mmol) and diisopropylazodicarboxylate (635 mg, 3.14 mmol), then after 18 h the reaction mixture was concentrated in vacuo. Chromatography (SiO₂; CH₂Cl₂/MeOH/NH₄OH 95:5:0.25) produced the title compound (180 mg, 41%). Colorless oil, MS (ISP)=169.2 (M+H)⁺.

d) (R)-4-But-3-enyl-2-methyl-3-oxo-piperazine-1-carboxylic acid tert-butyl ester The title compound was produced as described in intermediate 14b from (R)-1-but-3-enyl-3-methyl-piperazin-2-one. Colorless oil, MS (ISP)=269.5 (M+H)⁺.

e) (R)-2-Methyl-3-oxo-4-(3-piperidin-1-yl-propyl)-piperazine-1-carboxylic acid tert-butyl ester The title compound was produced from (R)-4-but-3-enyl-2-methyl-3-oxo-piperazine-1-carboxylic acid tert-butyl ester by oxidation to (R)-2-methyl-3-oxo-4-(3-oxo-propyl)-piperazine-1-carboxylic acid tert-butyl ester, followed by reductive amination with piperidine, as described in intermediate 7b. Light brown oil, MS (ISP)=340.3 (M+H)⁺.

Intermediate 32

(S)-2-Methyl-3-oxo-4-(3-piperidin-1-yl-propyl)-piperazine-1-carboxylic acid tert-butyl ester a) {(S)-1-[But-3-enyl-(2-hydroxy-ethyl)-carbamoyl]-ethyl}-carbamic acid tert-butyl ester The title compound was produced analogously to intermediate 28b from N-(tert-butoxycarbonyl)-L-alanine and 2-but-3-enylamino-ethanol (intermediate 31a). Colorless oil, MS (ISP)=287.3 (M+H)⁺.

b) (S)-1-But-3-enyl-3-methyl-piperazin-2-one

The title compound was produced analogously to intermediate 31 c from {(S)-1-[but-3-enyl-(2-hydroxy-ethyl)-carbamoyl]-ethyl}-carbamic acid tert-butyl ester. Colorless oil, MS (ISP)=169.2 (M+H)⁺.

c) (S)-4-But-3-enyl-2-methyl-3-oxo-piperazine-1-carboxylic acid tert-butyl ester The title compound was produced as described in intermediate 14b from (S)-1-but-3-enyl-3-methyl-piperazin-2-one. Colorless oil, MS (ISP)=269.5 (M+H)⁺.

d) (S)-2-Methyl-3-oxo)-4-(3-piperidin-1-yl-propyl)-piperazine-1-carboxylic acid tert-butyl ester The title compound was produced from (S)-4-but-3-enyl-2-methyl-3-oxo-piperazine-1-carboxylic acid tert-butyl ester by oxidation to (S)-2-methyl-3-oxo-4-(3-oxo-propyl)-piperazine-1-carboxylic acid tert-butyl ester, followed by reductive amination with piperidine, as described in intermediate 7b. Light brown oil, MS (ISP)=340.3 (M+H)⁺.

Intermediate 33

(R)-2-Hydroxymethyl-3-oxo-4-(3-piperidin-1-yl-propyl)-piperazine-1-carboxylic acid tert-butyl ester a) {(R)-2-Benzyloxy-1-[but-3-enyl-(2-hydroxy-ethyl)-carbamoyl]-ethyl}-carbamic acid tert-butyl ester The title compound was produced analogously to intermediate 28b from N-(tert-butoxycarbonyl)-O-benzyl-D-serine and 2-but-3-enylamino-ethanol (intermediate 31a). Colorless oil, MS (ISP)=415.3 (M+Na)⁺.

b) (R)-2-Benzyloxymethyl-4-but-3-enyl-3-oxo-piperazine-1-carboxylic acid tert-butyl ester The title compound was produced by transformation of {(R)-2-benzyloxy-1-[but-3-enyl-(2-hydroxy-ethyl)-carbamoyl]-ethyl}-carbamic acid tert-butyl ester to (R)-3-benzyloxymethyl-1-but-3-enyl-piperazin-2-one analogously to intermediate 31c, followed by Boc-protection as described in intermediate 14b. Light yellow oil, MS (ISP)=375.4 (M+H)⁺.

c) (R)-2-Benzyloxymethyl-3-oxo-4-(3-piperidin-1-yl-prolyl)-piperazine-1-carboxylic acid tert-butyl ester The title compound was produced from (R)-2-benzyloxymethyl-4-but-3-enyl-3-oxo-piperazine-1-carboxylic acid tert-butyl ester by oxidation to (R)-2-benzyloxymethyl-3-oxo-4-(3-oxo-propyl)-piperazine-1-carboxylic acid tert-butyl ester, followed by reductive amination with piperidine, as described in intermediate 7 b. Light yellow oil, MS (ISP)=446.3 (M+H)+.

d) (R)-2-Hydroxymethyl-3-oxo-4-(3-piperidin-1-yl-propyl)-piperazine-1-carboxylic acid tert-butyl ester A solution of (R)-2-benzyloxymethyl-3-oxo-4-(3-piperidin-1-yl-propyl)-piperazine-1-carboxylic acid tert-butyl ester (321 mg, 0.72 mmol) in acetic acid (9 ml) was stirred for 18 h at room temperature under a hydrogen atmosphere (3 bar) in the presence of palladium (10% on activated charcoal, 161 mg), then insoluble material was removed by filtration and the filtrate evaporated. The residue was partitioned between ethyl acetate and 2 M aq. sodium carbonate solution. The organic layer was dried (MgSO4), filtered, and evaporated to afford the title compound (200 mg, 78%). Light brown oil, MS (ISP)=356.4 (M+H)+.

Intermediate 34

(S)-2-Hydroxymethyl-3-oxo-4-(3-piperidin-1-yl-propyl)-piperazine-1-carboxylic acid tert-butyl ester a) {(S)-2-Benzyloxy-1-[but-3-enyl-(2-hydroxy-ethyl)-carbamoyl]-ethyl}-carbamic acid tert-butyl ester The title compound was produced analogously to intermediate 28b from N-(tert-butoxycarbonyl)-O-benzyl-L-serine and 2-but-3-enylamino-ethanol (intermediate 31a). Colorless oil, MS (ISP)=415.3 (M+Na)+.

b) (S)-2-Benzyloxymethyl-4-but-3-enyl-3-oxo-piperazine-1-carboxylic acid tert-butyl ester The title compound was produced by transformation of {(S)-2-benzyloxy-1-[but-3-enyl-(2-hydroxy-ethyl)-carbamoyl]-ethyl}-carbamic acid tert-butyl ester to (S)-3-benzyloxymethyl-1-but-3-enyl-piperazin-2-one analogously to intermediate 31c, followed by Boc-protection as described in intermediate 14b. Light yellow oil, MS (ISP)=375.4 (M+H)+.

c) (S)-2-Benzyloxymethyl-3-oxo-4-(3-piperidin-1-yl-propyl)-piperazine-1-carboxylic acid tert-butyl ester The title compound was produced from (S)-2-benzyloxymethyl-4-but-3-enyl-3-oxo-piperazine-1-carboxylic acid tert-butyl ester by oxidation to (S)-2-benzyloxymethyl-3-oxo-4-(3-oxo-propyl)-piperazine-1-carboxylic acid tert-butyl ester, followed by reductive amination with piperidine, as described in intermediate 7b. Light yellow oil, MS (ISP)=446.3 (M+H)+.

d) (S)-2-Hydroxymethyl-3-oxo-4-(3-piperidin-1-yl-propyl)-piperazine-1-carboxylic acid tert-butyl ester The title compound was produced analogously to intermediate 33d from (S)-2-benzyloxymethyl-3-oxo-4-(3-piperidin-1-yl-propyl)-piperazine-1-carboxylic acid tert-butyl ester. Light brown oil, MS (ISP)=356.4 (M+H)+.

Intermediate 35

8-Oxo-7-(3-piperidin-1-yl-propyl)-4,7-diaza-spiro[2.5]octane-4-carboxylic acid tert-butyl ester a) (1-But-3-enylcarbamoyl-cyclopropyl)-carbamic acid tert-butyl ester

The title compound was produced analogously to intermediate 1 from 1-[(tert-butoxycarbonyl)amino]cyclopropanecarboxylic acid and 3-buten-1-amine. White solid, MS (ISP)=277.3 (M+Na)+.

b) 7-But-3-enyl-8-oxo-4,7-diaza-spiro[2.5]octane-4-carboxylic acid tert-butyl ester Sodium hydride (60% dispersion in mineral oil, 206 mg, 5.15 mmol) was added at 0° C. to a solution of (1-but-3-enylcarbamoyl-cyclopropyl)-carbamic acid tert-butyl ester (400 mg, 1.57 mmol) in tetrahydrofuran (8 ml), then after 15 min a solution of 1,2-bis(((trifluoromethyl)sulfonyl)oxy)ethane (Chem. Ber. 1981, 114, 810; 616 mg, 1.89 mmol) in tetrahydrofuran (1 ml) was added dropwise. After 1 h, another portion of sodium hydride (60% dispersion in mineral oil, 103 mg, 2.58 mmol) and after 15 min, 1,2-bis(((trifluoromethyl)sulfonyl)oxy)ethane (616 mg, 1.78 mmol) was added, and the reaction mixture was allowed to reach room temperature over 1 h, then partitioned between ethyl acetate and water. The organic layer was washed with brine, dried (MgSO4), and evaporated. Chromatography (SiO2; heptane-ethyl acetate gradient) produced the title compound (208 mg, 47%). Yellow oil, MS (ISP)=281.2 (M+H)+.

c) 8-Oxo-7-(3-piperidin-yl-propyl)-4,7-diaza-spiro[2.5]octane-4-carboxylic acid tert-butyl ester The title compound was produced from 7-but-3-enyl-8-oxo-4,7-diaza-spiro[2.5]octane-4-carboxylic acid tert-butyl ester by oxidation to 8-oxo-7-(3-oxo-propyl)-4,7-diaza-spiro[2.5]octane-4-carboxylic acid tert-butyl ester, followed by reductive amination with piperidine, as described in intermediate 7b. Light brown oil, MS (ISP)=356.4 (M+H)+.

Example 1

4-[(E)-3-(3,4-Dichloro-phenyl)-acryloyl]-3-methyl-1-(3-piperidin-1-yl-propyl)-piperazin-2-one

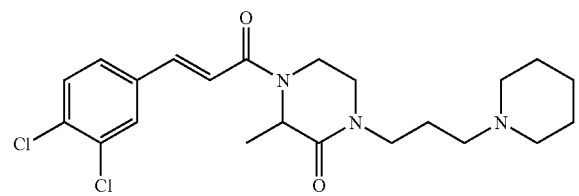

Sodium hydride (55% dispersion in mineral oil, 21 mg, 0.48 mmol) was added at room temperature to a solution of 4-[(E)-3-(3,4-dichloro-phenyl)-acryloyl]-3-methyl-piperazin-2-one (intermediate 1; 100 mg, 0.32 mmol) in N,N-dimethylacetamide (2 ml), then after 20 min a solution of 1-(3-chloropropyl)-piperidine (prepared from the commercially available hydrochloride salt (127 mg, 0.64 mmol) by basic extraction as described in intermediate 6) in toluene (1 ml) was added. The reaction mixture was stirred for 16 h at 50° C., then partitioned between water and ethyl acetate. The organic layer was washed with brine, dried (MgSO$_4$), and evaporated. Chromatography (SiO$_2$; CH$_2$Cl$_2$/MeOH/NH$_4$OH 95:5:0.25) afforded the title compound (66 mg, 47%). Colorless gum, MS (ISP)=438.4 (M+H)$^+$.

Example 2

4-[(E)-3-(3,4-Dichloro-phenyl)-acryloyl]-1-(3-piperidin-1-yl-propyl)-piperazin-2-one

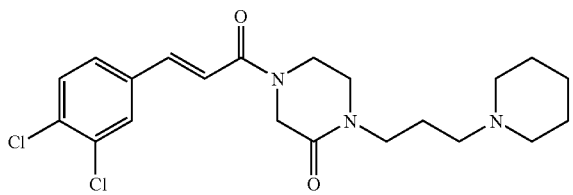

The title compound was produced in analogy to example 1 from 4-[(E)-3-(3,4-dichloro-phenyl)-acryloyl]-piperazin-2-one (intermediate 2) and 1-(3-chloropropyl)-piperidine. Colorless gum, MS (ISP)=424.2 (M+H)$^+$.

Example 3

4-[(E)-3-(3-Chloro-phenyl)-acryloyl]-1-(3-piperidin-1-yl-propyl)-piperazin-2-one

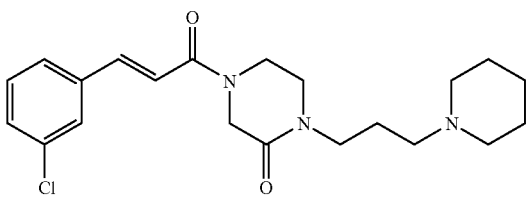

The title compound was produced in analogy to example 1 from 4-[(E)-3-(3-chlorophenyl)-acryloyl]-piperazin-2-one (intermediate 3) and 1-(3-chloropropyl)-piperidine. Off-white foam, MS (ISP)=390.1 (M+H)$^+$.

Example 4

4-[(E)-3-(3,4-Dichloro-phenyl)-acryloyl]-3,3-dimethyl-1-(3-piperidin-1-yl-propyl)-piperazin-2-one

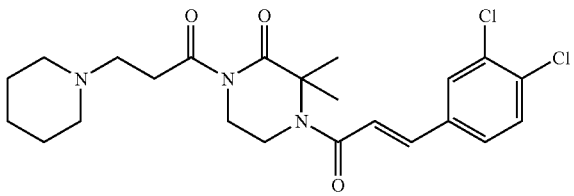

The title compound was produced in analogy to example 1 from 4-[(E)-3-(3,4-dichloro-phenyl)-acryloyl]-3,3-dimethyl-piperazin-2-one (intermediate 4) and 1-(3-chloropropyl)-piperidine. Light yellow oil, MS (ISP)=452.1 (M+H)$^+$.

Example 5

4-[(E)-3-(3,4-Dichloro-phenyl)-acryloyl]-1-(4-piperidin-1-yl-butyl)-piperazin-2-one

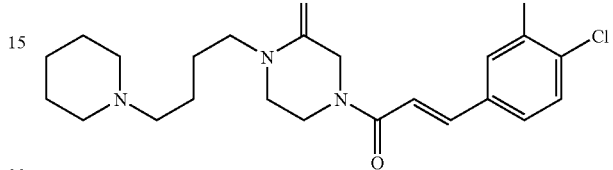

Lithium aluminum hydride solution (1 M in tetrahydrofuran, 0.13 ml, 0.13 mmol) was added dropwise at −30° C. to a solution of 4-{4-[(E)-3-(3,4-dichloro-phenyl)-acryloyl]-2-oxo-piperazin-1-yl}-N-methoxy-N-methyl-butyramide (intermediate 5; 54 mg, 0.13 mmol), then after 10 min the reaction mixture was, cooled to −75° C. and acetone (161 mg, 2.8 mmol) was added. The homogeneous solution was allowed to reach room temperature over 16 h, then partitioned between water and ethyl acetate. The organic layer was washed with brine, dried (MgSO$_4$), and evaporated. The crude aldehyde intermediate (4-{4-[(E)-3-(3,4-dichloro-phenyl)-acryloyl]-2-oxo-piperazin-1-yl}-butyraldehyde) and piperidine (10 mg, 0.12 mmol) were dissolved in 1,2-dichloroethane, then a freshly prepared solution of pyridine borane complex (8 M in pyridine, 30 µl, 0.33 mmol) and acetic acid (22 mg, 0.37 mmol) in ethanol (1 ml) was added dropwise at room temperature. The reaction mixture was stirred overnight, then volatile material was removed by rotary evaporation. The residue was purified by chromatography (SiO$_2$; CH$_2$Cl$_2$/MeOH/NH$_4$OH 90:10:0.25) to afford the title compound (28 mg, 51%). Light yellow gum, MS (ISP)=438.2 (M+H)$^+$.

Example 6

4-((E)-3-Naphthalen-2-yl-acryloyl)-1-(2-pyrrolidin-1-yl-ethyl)-piperazin-2-one

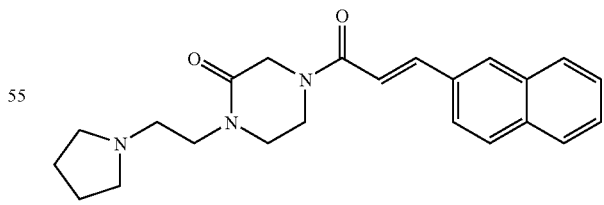

3-Oxo-4-(2-pyrrolidin-1-yl-ethyl)-piperazine-1-carboxylic acid tert-butyl ester (intermediate 6; 0.03 g, 0.1 mmol) was treated with a hydrogen chloride solution (4 M in 1,4-dioxane, 1 ml) for 15 minutes after which time the solvent was evaporated. The crude salt was dissolved in N,N-dimethylformamide (0.8 ml) with triethylamine (0.06 ml, 0.4 mmol) and (E)-3-naphthalen-2-yl-acrylic acid (0.02 g, 0.1 mmol)

and O-(7-azabenzotriazol-1-yl)-N,N,N',N'-tetramethyluronium hexafluoro-phosphate (0.04 g, 0.1 mmol) were added. The mixture was shaken for 1 h after which time it was directly purified by preparative HPLC. MS (ISP)=378.6 (M+H)⁺.

Example 7

4-[(E)-3-(3,4-Dichloro-phenyl)-acryloyl]-1-(2-pyrrolidin-1-yl-ethyl)-piperazin-2-one

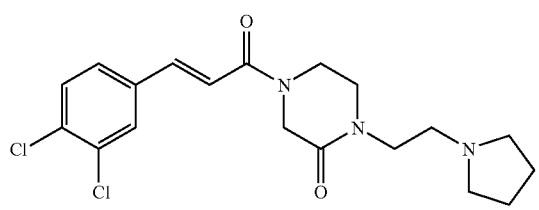

The title compound was prepared in analogy to example 6 starting from 3-oxo-4-(2-pyrrolidin-1-yl-ethyl)-piperazine-1-carboxylic acid tert-butyl ester (intermediate 6) and 3,4-dichlorocinnamic acid. MS (ISP)=396.4 (M+H)⁺.

Example 8

4-[(E)-3-(3,4-Dichloro-phenyl)-acryloyl]-1-[3-((R)-2-hydroxymethyl-pyrrolidin-1-yl)-propyl]-piperazin-2-one

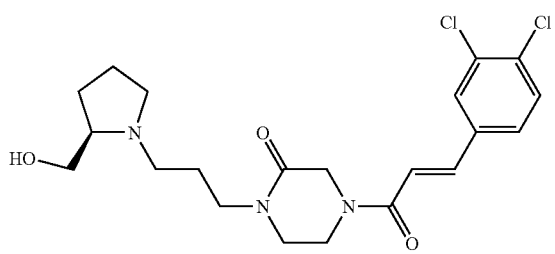

Hydrogen chloride solution (4 M in 1,4-dioxane, 2 ml) was added to a solution of 4-[3-((R)-2-hydroxymethyl-pyrrolidin-1-yl)-propyl]-3-oxo-piperazine-1-carboxylic acid tert-butyl ester (intermediate 7; 157 mg, 0.46 mmol) in 1,4-dioxane (2 ml), then after 90 min volatile material was removed by rotary evaporation. The residue was taken up in dichloromethane (10 ml), treated with 4-methylmorpholine (232 mg, 2.30 mmol), and the mixture obtained concentrated in vacuo. The residue was taken up in N,N-dimethylformamide (2 ml), then 4-methylmorpholine (232 mg, 2.30 mmol), 3,4-dichlorocinnamic acid (108 mg, 0.48 mmol), and O-(7-azabenzotriazol-1-yl)-N,N,N',N'-tetramethyluronium hexafluoro-phosphate (262 mg, 0.69 mmol) were added. The solution was stirred at room temperature for 3 h, then mixture was partitioned between water and ethyl acetate. The organic layer was washed with brine, dried (MgSO₄), and evaporated. Chromatography (SiO₂; CH₂Cl₂/MeOH/NH₄OH 80:20:0.25) produced the title compound (82 mg, 41%). Colorless gum, MS (ISP)=440.3 (M+H)⁺.

Example 9

4-[(E)-3-(3,4-Dichloro-phenyl)-acryloyl]-1-[3-(3-hydroxy-piperidin-1-yl)-propyl]-piperazin-2-one

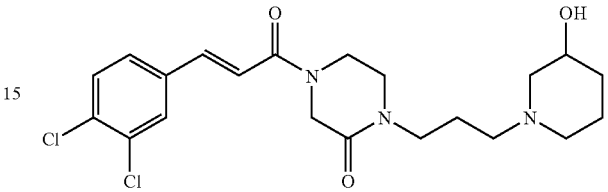

The title compound was produced in analogy to example 8 from 4-[3-(3-hydroxy-piperidin-1-yl)-propyl]-3-oxo-piperazine-1-carboxylic acid tert-butyl ester (intermediate 8) and 3,4-dichlorocinnamic acid White solid, MS (ISP)=440.3 (M+H)⁺.

Example 10

4-[(E)-3-(3,4-Dichloro-phenyl)-acryloyl]-1-[3-((S)-2-hydroxymethyl-pyrrolidin-1-yl)-propyl]-piperazin-2-one

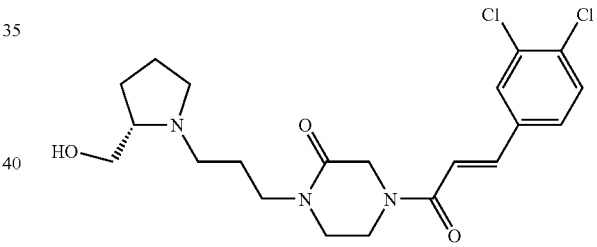

The title compound was produced in analogy to example 8 from 4-[3-((S)-2-hydroxymethyl-pyrrolidin-1-yl)-propyl]-3-oxo-piperazine-1-carboxylic acid tert-butyl ester (intermediate 9) and 3,4-dichlorocinnamic acid. White solid, MS (ISP)=440.3 (M+H)⁺.

Example 11

4-[(E)-3-(3,4-Dichloro-phenyl)-acryloyl]-1-[3-(4-hydroxy-piperidin-1-yl)-propyl]-piperazin-2-one

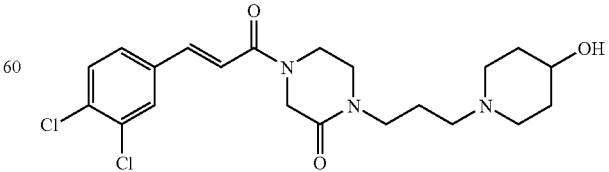

The title compound was produced in analogy to example 8 from 4-[3-(4-hydroxy-piperidin-1-yl)-propyl]-3-oxo-piperazine-1-carboxylic acid tert-butyl ester (intermediate 10) and 3,4-dichlorocinnamic acid. White solid, MS (ISP)=440.3 (M+H)⁺.

Example 12

4-[(E)-3-(3,4-Dichloro-phenyl)-acryloyl]-1-(3-pyrrolidin-1-yl-propyl)-piperazin-2-one

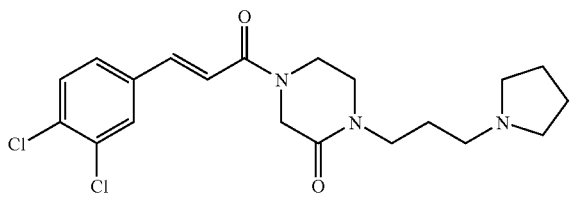

The title compound was produced in analogy to example 8 from 3-oxo-4-(3-pyrrolidin-1-yl-propyl)-piperazine-1-carboxylic acid tert-butyl ester (intermediate 11) and 3,4-dichlorocinnamic acid. Colorless gum, MS (ISP)=410.2 (M+H)⁺.

Example 13

4-[(E)-3-(3,4-Dichlorophenyl)-acryloyl]-1-[3-(3-hydroxy-pyrrolidin-1-yl)-propyl]-piperazin-2-one

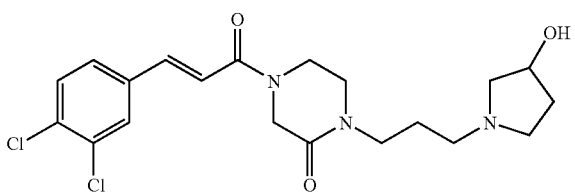

The title compound was produced in analogy to example 8 from 4-[3-(3-hydroxy-pyrrolidin-1-yl)-propyl]-3-oxo-piperazine-1-carboxylic acid tert-butyl ester (intermediate 12) and 3,4-dichlorocinnamic acid. White solid, MS (ISP)=426.0 (M+H)⁺.

Example 14

4-[(E)-3-(3,4-Dichloro-phenyl)-acryloyl]-1-[3-(3-hydroxymethyl-pyrrolidin-1-yl)-propyl]-piperazin-2-one

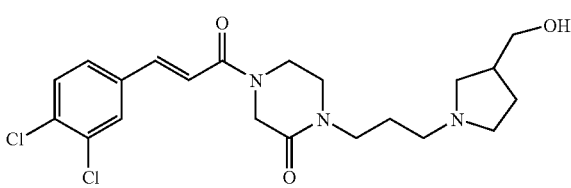

The title compound was produced in analogy to example 8 from 4-[3-(3-hydroxymethyl-pyrrolidin-1-yl)-propyl]-3- oxo-piperazine-1-carboxylic acid tert-butyl ester (intermediate 13) and 3,4-dichlorocinnamic acid. White solid, MS (ISP)=440.3 (M+H)⁺.

Example 15

4-[(E)-3-(3,4-Dichloro-phenyl)-acryloyl]-3-methyl-1-(3-pyrrolidin-1-yl-propyl)-piperazin-2-one

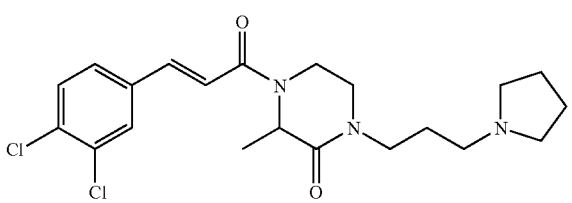

The title compound was produced in analogy to example 8 from 2-methyl-3-oxo-4-(3-pyrrolidin-1-yl-propyl)-piperazine-1-carboxylic acid tert-butyl ester (intermediate 14) and 3,4-dichlorocinnamic acid. Colorless gum, MS (ISP)=424.2 (M+H)⁺.

Example 16

4-[(E)-3-(3-Chlorophenyl)-acryloyl]-3-methyl-1-(3-pyrrolidin-1-yl-propyl)-piperazin-2-one

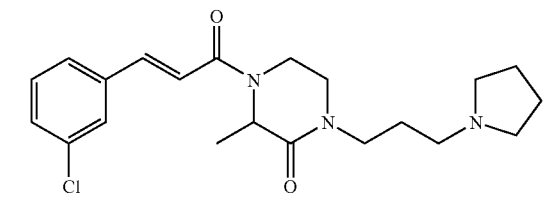

The title compound was produced in analogy to example 8 from 2-methyl-3-oxo-4-(3-pyrrolidin-1-yl-propyl)-piperazine-1-carboxylic acid tert-butyl ester (intermediate 14) and 3-dichlorocinnamic acid. Colorless gum, MS (ISP)–390.3 (M+H)⁺.

Example 17

4-[(E)-3-(3,4-Dichloro-phenyl)-acryloyl]-1-[3-((S)-2-hydroxymethyl-pyrrolidin-1-yl)-propyl]-3-methyl-piperazin-2-one

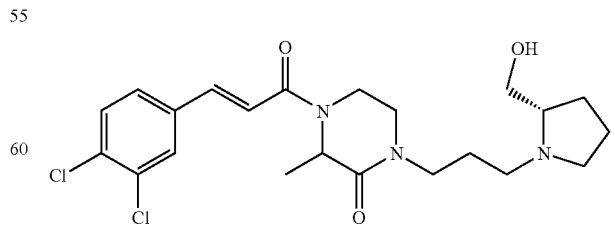

The title compound was produced in analogy to example 8 from 4-[3-((S)-2-hydroxymethyl-pyrrolidin-1-yl)-propyl]-2-methyl-3-oxo-piperazine-1-carboxylic acid tert-butyl ester (intermediate 15) and 3,4-dichlorocinnamic acid. Colorless gum, MS (ISP)=454.2 (M+H)⁺.

Example 18

4-[(E)-3-(3-Chloro-phenyl)-acryloyl]-1-[3-((S)-2-hydroxymethyl-pyrrolidin-1-yl)-propyl]-3-methyl-piperazin-2-one

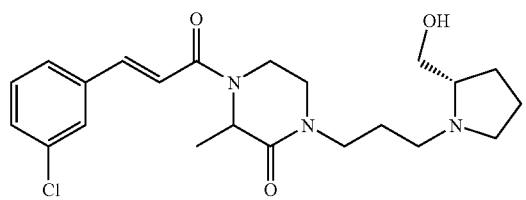

The title compound was produced in analogy to example 8 from 4-[3-((S)-2-hydroxymethyl-pyrrolidin-1-yl)-propyl]-2-methyl-3-oxo-piperazine-1-carboxylic acid tert-butyl ester (intermediate 15) and 3-chlorocinnamic acid. Colorless gum, MS (ISP)=420.2 (M+H)⁺.

Example 19

4-[(E)-3-(3,4-Dichloro-phenyl)-acryloyl]-1-[3-(4-hydroxy-piperidin-1-yl)-propyl]-3-methyl-piperazin-2-one

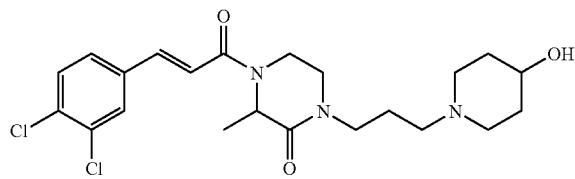

The title compound was produced was analogy to example 8 from 4-[3-(4-hydroxy-piperidin-1-yl)-propyl]-2-methyl-3-oxo-piperazine-1-carboxylic acid tert-butyl ester (intermediate 16) and 3,4-dichlorocinnamic acid. Colorless gum, MS (ISP)=454.2 (M+H)⁺.

Example 20

4-[(E)-3-(3-Chloro-phenyl)-acryloyl]-1-[3-(4-hydroxy-piperidin-1-yl)-propyl]-3-methyl-piperazin-2-one

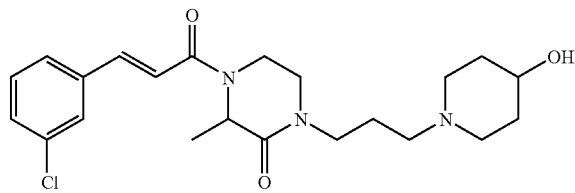

The title compound was produced in analogy to example 8 from 4-[3-(4-hydroxy-piperidin-1-yl)-propyl]-2-methyl-3-oxo-piperazine-1-carboxylic acid tert-butyl ester (intermediate 16) and 3-chlorocinnamic acid. Colorless gum, MS (ISP)=420.2 (M+H)⁺.

Example 21

4-[(E)-3-(3,4-Dichloro-phenyl)-acryloyl]-3-ethyl-1-(3-piperidin-1-yl-propyl)-piperazin-2-one

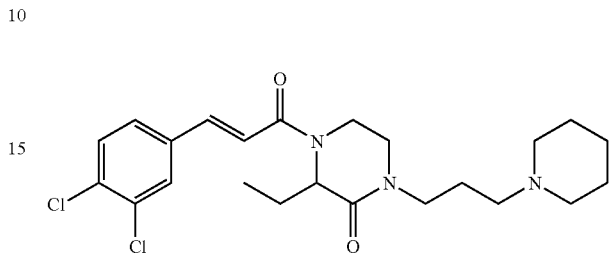

The title compound was produced in analogy to example 8 from 2-ethyl-3-oxo-4-(3-piperidin-1-yl-propyl)-piperazine-1-carboxylic acid tert-butyl ester (intermediate 17) and 3,4-dichlorocinnamic acid. Orange guns MS (ISP)=452.1 (M+H)⁺.

Example 22

4-[(E)-3-(3-Chloro-4-fluoro-phenyl)-acryloyl]-3-ethyl-1-(3-piperidin-1-yl-propyl)-piperazin-2-one

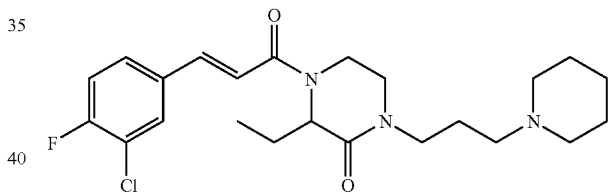

The title compound was produced in analogy to example 8 from 2-ethyl-3-oxo-4-(3-piperidin-1-yl-propyl)-piperazine-1-carboxylic acid tert-butyl ester (intermediate 17) and 3-chloro-4-fluorocinnamic acid. Orange gum, MS (ISP)=436.2 (M+H)⁺.

Example 23

(R)-4-[(E)-3-(3,4-Dichloro-phenyl)-acryloyl]-5-methyl-1-(3-piperidin-1-yl-propyl)-piperazin-2-one

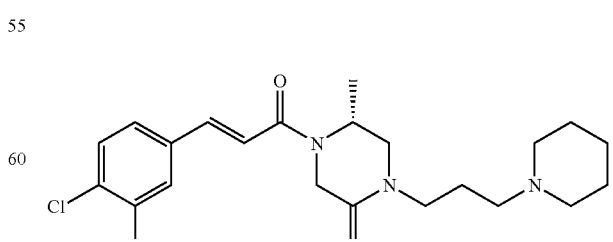

The title compound was produced in analogy to example 8 from (R)-2-methyl-5-oxo-4-(3-piperidin-1-yl-propyl)-piperazine-1-carboxylic acid tert-butyl ester (intermediate 18) and 3,4-dichlorocinnamic acid. Light yellow oil, MS (ISP)=438.2 (M+H)+.

Example 24

(S)-4-[(E)-3-(3,4-Dichloro-phenyl)-acryloyl]-5-methyl-1-(3-piperidin-1-yl-propyl)-piperazin-2-one

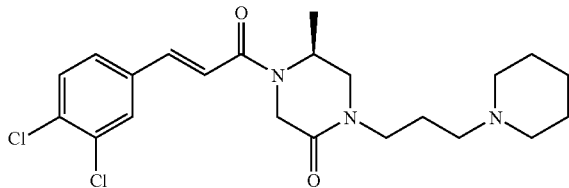

The title compound was produced in analogy to example 8 from (S)-2-methyl-5-oxo-4-(3-piperidin-1-yl-propyl)-piperazine-1-carboxylic acid tert-butyl ester (intermediate 19) and 3,4-dichlorocinnamic acid. Orange foam, MS (ISP)=438.2 (M+H)+.

Example 25

4-[(E)-3-(3,4-Dichloro-phenyl)-acryloyl]-3-methyl-1-(4-piperidin-1-yl-butyl)-piperazin-2-one

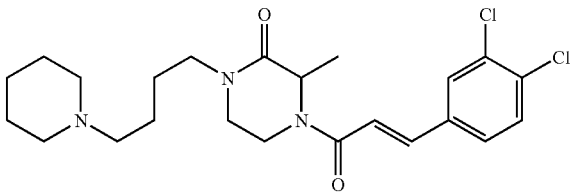

Sodium metaperiodate (310 mg, 1.45 mmol) and osmium (VIII) oxide (2.5% solution in tert-butylalcohol, 49 µl, 48 µmol) were added at 0° C. to a solution of 4-[(E)-3-(3,4-dichloro-phenyl)-acryloyl]-3-methyl-1-pent-4-enyl-piperazin-2-one (intermediate 20; 184 mg, 0.48 mmol) in acetone/water 1:1 (10 ml). The reaction mixture was stirred at 0° C. for 30 min, then allowed to reach room temperature over 45 min, then partitioned between ethyl acetate and water. The organic layer was washed with brine, dried (MgSO4), and evaporated. The crude aldehyde intermediate [4-{-4-[(E)-3-(3,4-dichloro-phenyl)-acryloyl]-3-methyl-2-oxo-piperazin-1-yl}-butyraldehyde] and piperidine (33 mg, 0.39 mmol) were dissolved in 1,2-dichloroethane (1.5 ml), then a freshly prepared solution of pyridine borane complex (8 M in pyridine, 71 µl, 0.78 mmol) and acetic acid (69 mg, 1.16 mmol) in ethanol (1.5 ml) was added dropwise at room temperature. The reaction mixture was stirred overnight, then 25%. aq. ammonium hydroxide solution (0.16 ml) was added, and volatile material was removed by rotary evaporation. The residue was purified by chromatography (SiO2; CH2Cl2/ MeOH/NH4OH 90:10:0.25) to afford the title compound (15 mg, 11%). Light yellow solid, MS (ISP)=452.1 (M+H)+.

Example 26

4-[(E)-3-(3,4-Dichloro-phenyl)-acryloyl]-1-[4-((S)-2-hydroxymethyl-pyrrolidin-1-yl)-butyl]-3-methyl-piperazin-2-one

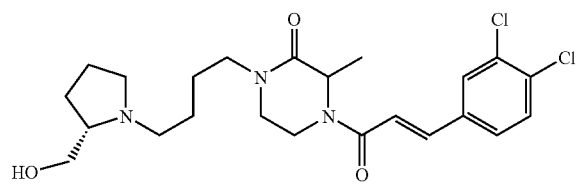

The title compound was produced in analogy to example 25 from 4-[(E)-3-(3,4-dichloro-phenyl)-acryloyl]-3-methyl-1-pent-4-enyl-piperazin-2-one (intermediate 20) and L-prolinol. Light yellow gum, MS (ISP)=468.1 (M+H)+.

Example 27

4-[(E)-3-(3,4-Dichloro-phenyl)-acryloyl]-1-[4-((R)-2-hydroxymethyl-pyrrolidin-1-yl)-butyl]-3-methyl-piperazin-2-one

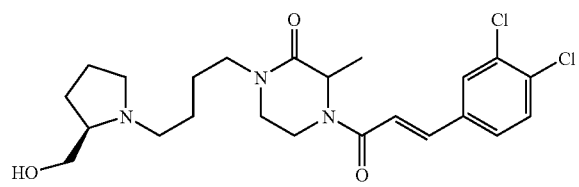

The title compound was produced in analogy to example 25 from 4-[(E)-3-(3,4-dichloro-phenyl)-acryloyl]-3-methyl-1-pent-4-enyl-piperazin-2-one (intermediate 20) and D-prolinol. Light yellow gum, MS (ISP)=468.2 (M+H)+.

Example 28

4-[(E)-3-(3,4-Dichloro-phenyl)-acryloyl]-1-[4-(3-hydroxy-piperidin-1-yl)-butyl]-3-methyl-piperazin-2-one

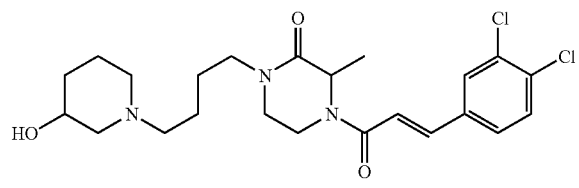

The title compound was produced in analogy to example 25 from 4-[(E)-3-(3,4-dichloro-phenyl)-acryloyl]-3-methyl-1-pent-4-enyl-piperazin-2-one (intermediate 20) and piperidin-3-ol. Light yellow gum, MS (ISP)=468.2 (M+H)+.

Example 29

4-[(E)-3-(3,4-Dichloro-phenyl)-acryloyl]-1-[4-(4-hydroxy-piperidin-1-yl)-butyl]-3-methyl-piperazin-2-one

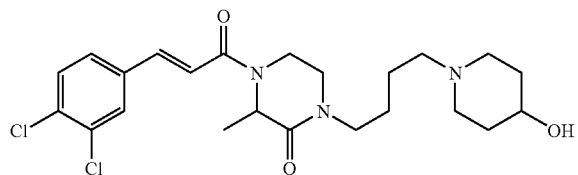

The title compound was produced in analogy to example 25 from 4-[(E)-3-(3,4-dichloro-phenyl)-acryloyl]-3-methyl-1-pent-4-enyl-piperazin-2-one (intermediate 20) and piperidin-4-ol. Light yellow gum, MS (ISP)=468.0 (M+H)$^+$.

Example 30

4-[(E)-3-(3,4-Dichloro-phenyl)-acryloyl]-6-methyl-1-(3-piperidin-1-yl-propyl)-piperazin-2-one

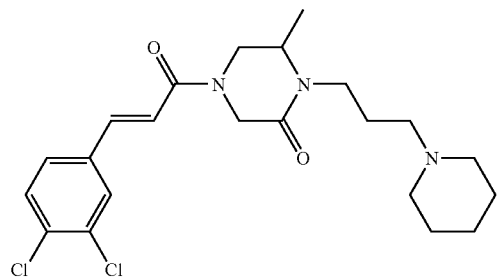

The title compound was produced in analogy to example 8 from 3-methyl-5-oxo-4-(3-piperidin-1-yl-propyl)-piperazine-1-carboxylic acid tert-butyl ester (intermediate 21) and 3,4-dichlorocinnamic acid. Orange foam, MS (ISP)=438.4 (M+H)$^+$.

Examples 31 and 32

(+)-4-[(E)-3-(3,4-Dichloro-phenyl)-acryloyl]-6-methyl-1-(3-piperidin-1-yl-propyl)-piperazin-2-one and (−)-4-[(E)-3-(3,4-Dichloro-phenyl)-acryloyl]-6-methyl-1-(3-piperidin-1-yl-propyl)-piperazin-2-one

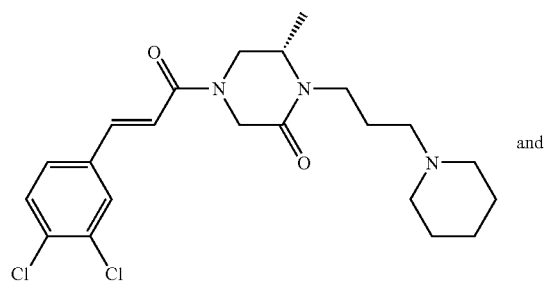

and

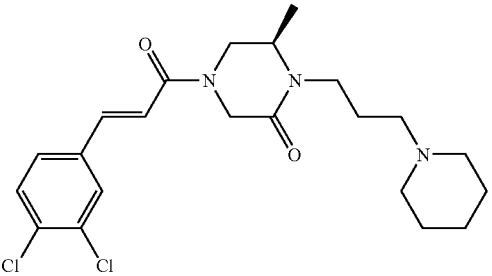

The racemate 4-[(E)-3-(3,4-dichloro)-phenyl)-acryloyl]-6-methyl-1-(3-piperidin-1-yl-propyl)-piperazin-2-one (example 30; 64 mg, 0.15 mmol) was separated on a Chiralpak AD HPLC column, using heptane/2-propanol 85:15 as the eluent. This afforded the (+)-enantiomer (8 mg, 13%; colorless gum, MS (ISP)=438.4 (M+H)$^+$) and the (−) enantiomer (14 mg, 22%; colorless Gum, MS (ISP)=438.4 (M+H)$^+$).

Example 33

[1-[(E)-3-(3,4-Dichloro-phenyl)-acryloyl]-3-oxo-4-(3-piperidin-1-yl-propyl)-piperazin-2-yl]-acetic acid ethyl ester

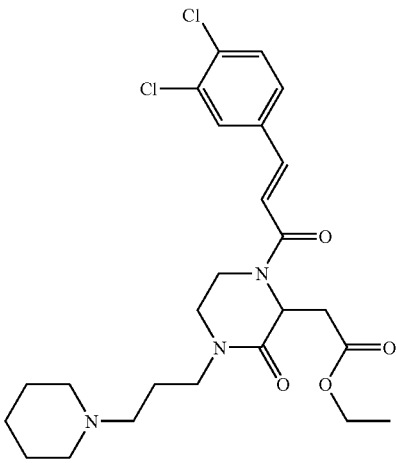

The title compound was produced in analogy to example 8 from 2-ethoxycarbonylmethyl-3-oxo-4-(3-piperidin-1-yl-propyl)-piperazine-1-carboxylic acid tert-butyl ester (intermediate 22) and 3,4-dichlorocinnamic acid. Off-white solid, MS (ISP)=510.1 (M+H)$^+$.

Example 34

(E)-3-(3,4-Dichloro-phenyl)-1-[1,1-dioxo-2-(3-piperidin-1-yl-propyl)-[1,2,5]thiadiazinan-5-yl]-propenone

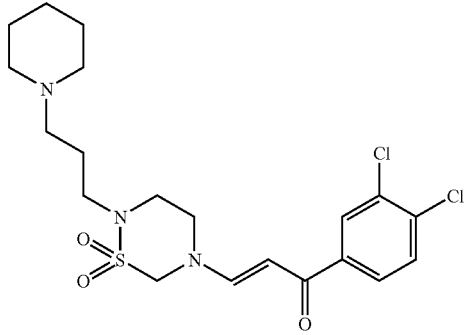

Trifluoroacetic acid (6.9 g, 60 mmol) was added at 0° C. to a solution of {2-[(E)-3-(3,4-dichloro-phenyl)-acryloylamino]ethyl}-carbamic acid tert-butyl either (intermediate 23; 2.16 g, 6.02 mmol) in dichloromethane (22 ml). The reaction mixture was allowed to reach room temperature over 90 min, then volatile material was removed by rotary evaporation. The residue was partitioned between ethyl acetate and 1 M aq. sodium hydroxide solution. The organic layer was washed with brine, dried (MgSO$_4$), and evaporated. The crude intermediate [(E)-N-(2-amino-ethyl)-3-(3,4-dichlorophenyl)-acrylamide] and triethylamine (608 mg, 6.02 mmol) were dissolved in tetrahydrofuran (22 ml), cooled to 0° C., then and a solution of chloro-methanesulfonyl chloride (914 mg, 6.02 mmol) in tetrahydrofuran (10 ml) was added dropwise at room temperature, then after 1 h the reaction mixture was partitioned between ethyl acetate and sat. aq. ammonium chloride solution. The organic layer was washed with brine, dried (MgSO$_4$), and evaporated to produce crude (E)-N-(2-chloromethanesulfonylamino-ethyl)-3-(3,4-dichloro-phenyl)-acrylamide (2.11 g). This intermediate was suspended in tetrahydrofuran (50 mmol), then potassium tert-butylate (1.51 g, 13.5 mmol) was added, and the orange solution was heated at 40° C. for 2 h, then partitioned between ethyl acetate and sat. aq. ammonium chloride solution. The organic layer was washed with brine, dried (MgSO$_4$), and evaporated. After chromatography (SiO$_2$; CH$_2$Cl$_2$/MeOH/NH$_4$OH 90:10:0.25), 410 mg of a mixture of (E)-3-(3,4-dichlorophenyl)-1-[1,1-dioxo-[1,2,5]thiadiazinan-5-yl]-propenone and unidentified impurities was obtained. This material was dissolved in N,N-dimethylacetamide (4 ml), treated at room temperature with sodium hydride (60% dispersion in mineral oil, 80 mg, 2.0 mmol), then after 20 min a solution of 1-(3-chloropropyl)-piperidine [prepared from the commercially available hydrochloride salt (485 mg, 2.45 mmol) by basic extraction as described in intermediate 6] in toluene (4 ml) was added. The reaction mixture was heated at 50° C. for 5 h, then partitioned between water and heptane/ethyl acetate 1:1. The organic layer was washed with brine, dried (MgSO$_4$), and evaporated. Chromatography (SiO$_2$; CH$_2$Cl$_2$/MeOH/NH$_4$OH 90:10:0.25) produced the title compound (45 mg, 2%). White solid, MS (ISP)=460.1 (M+H)$^+$.

Example 35

4-[(E)-3-(3,4-Dichloro-phenyl)-acryloyl]-1-(2-hydroxy-3-piperidin-1-yl-propyl)-piperazin-2-one

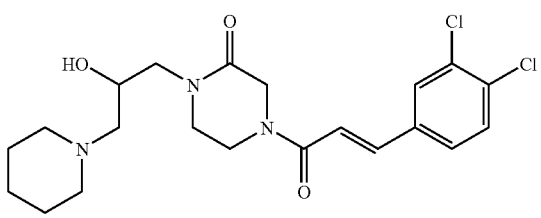

The title compound was produced in analogy to example 8 from 4-(2-hydroxy-3-piperidin-1-yl-propyl)-3-oxo-piperazine-1-carboxylic add tert-butyl ester (intermediate 24) and 3,4-dichlorocinnamic acid. Orange solid, MS (ISP)=440.2 (M+H)$^+$.

Example 36

4-[(E)-3-(3-Chloro-4-fluoro-phenyl)-acryloyl]-1-(2-hydroxy-3-piperidin-1-yl-propyl)-piperazin-2-one

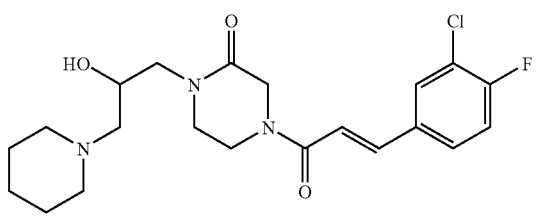

The title compound was produced in analogy to example 8 from 4-(2-hydroxy-3-piperidin-1-yl-propyl)-3-oxo-piperazine-1-carboxylic acid tert-butyl ester (intermediate 24) and 3-chloro-4-fluorocinnamic acid. Orange solid, MS (ISP)=424.2 (M+H)$^+$.

Example 37

4-[(E)-3-(3-Chloro-phenyl)-acryloyl]-1-(2-hydroxy-3-piperidin-1-yl-propyl)-piperazin-2-one

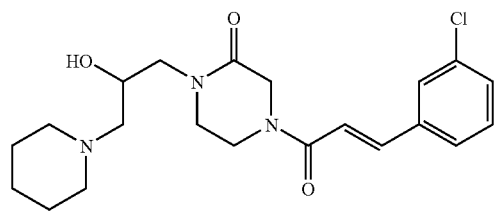

The title compound was produced in analogy to example 8 from 4-(2-hydroxy-3-piperidin-1-yl-propyl)-3-oxo-piperazine-1-carboxylic acid tert-butyl ester (intermediate 24) and 3-chlorocinnamic acid. Orange solid, MS (ISP)=406.3 (M+H)$^+$.

Example 38

4-[(E)-3-(3,4-Dichlorophenyl)-acryloyl]-1-[3-((S)-4-hydroxy-6-aza-spiro[2.5]oct-6-yl)-propyl]-3-methyl-piperazin-2-one

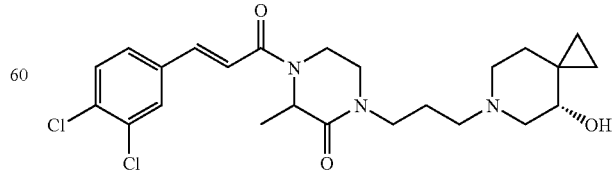

To a suspension of (S)-6-aza-spiro[2.5]octan-4-ol hydrochloride (intermediate 25; 0.03 g, 0.2 mmol) in dichloromethane (1 ml) was added triethylamine (0.03 ml, 0.2 mmol) and acetic acid (0.02 ml, 0.4 mmol) followed by a solution of crude 2-methyl-3-oxo-4-(3-oxo-propyl)-piperazine-1-carboxylic acid tert-butyl ester (intermediate 14c; 0.06 g, 0.24 mmol) in dichloromethane (1 ml). Sodium triacetoxyborohydride (0.06 g, 0.26 mmol) was then added and the mixture stirred for 2 h, after which time the mixture was washed with saturated aq. sodium hydrogencarbonate solution, dried (Na$_2$SO$_4$) and concentrated. The crude residue was then treated with HCl in dioxane (2 ml, 4 N) and stirred for 30 minutes after which time the reaction was concentrated to afford crude 1-[3-((S)-4-hydroxy-6-aza-spiro[2.5]oct-6-yl)-propyl]-3-methyl-piperazin-2-one dihydrochloride as a white powder (0.1 g). To a solution of crude 1-[3-((S)-4-hydroxy-6-aza-spiro[2.5]oct-6-yl)-propyl]-3-methyl-piperazin-2-one dihydrochloride (0.03 g, 0.1 mmol) in N,N-dimethylformamide (0.8 ml) was added 3,4-dichlorocinnamic acid (0.2 g, 0.1 mmol), triethylamine (0.05 ml, 0.4 mmol) and O-(7-azabenzotriazol-1-yl)-N,N,N',N'-tetramethyluronium hexafluoro-phosphate (4 g, 0.1 mmol) and the reaction shaken for 1 h, after which time the reaction mixture was directly purified by preparative HPLC. This afforded the titled product as a colorless gum. MS (ISP)=480.1 (M+H)$^+$.

Example 39

4-[(E)-3-(4-Chloro-3-fluoro-phenyl)-acryloyl]-1-[3-((S)-4-hydroxy-6-aza-spiro[2,5]oct-6-yl)-propyl]-3-methyl-piperazin-2-one

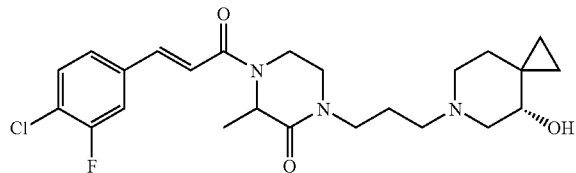

To a solution of crude 1-[3-((S)-4-hydroxy-6-aza-spiro[2,5]oct-6-yl)-propyl]-3-methyl-piperazin-2-one dihydrochloride (example 38; 0.03 g, 0.1 mmol) in N,N-dimethylformamide (0.8 ml) was added 4-chloro-3-fluorocinnamic acid (0.02 g, 0.1 mmol), triethylamine (0.05 ml, 0.4 mmol) and O-(7-azabenzotriazol-1-yl)-N,N,N',N'-tetramethyluronium hexafluoro-phosphate (0.04 g, 0.1 mmol) and the reaction shaken for 1 h, after which time the reaction mixture was directly purified by preparative HPLC. This afforded the titled product as a colorless gum. MS (ISP)=464.3 (M+H)$^+$.

Example 40

4-[(E)-3-(3-Chloro-4-fluoro-phenyl)-acryloyl]-1-[3-((S)-4-hydroxy-6-aza-spiro[2.5]oct-6-yl)-propyl]-3-methyl-piperazin-2-one

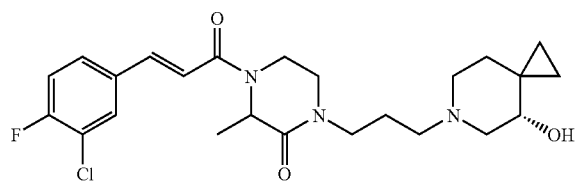

To a solution of crude 1-[3-((S)-4-hydroxy-6-aza-spiro[2.5]oct-6-yl)-propyl]-3-methyl-piperazin-2-one dihydrochloride (example 38; 0.03 g, 0.1 mmol) in N,N-dimethylformamide (0.8 ml) was added 3-chloro-4-fluorocinnamic acid (0.02 g, 0.1 mmol), triethylamine (0.05 ml, 0.4 mmol) and O-(7-azabenzotriazol-1-yl)-N,N,N',N'-tetramethyluronium hexafluoro-phosphate (0.04 g, 0.1 mmol) and the reaction shaken for 1 h, after which time the reaction mixture was directly purified by preparative HPLC. This afforded the titled product as a colorless gum MS (ISP)=464.3 (M+H)$^+$.

Example 41

4-[(E)-3-(3,4-Dichloro-phenyl)-acryloyl]-1-[3-((3S,4S)-3-hydroxy-4-methyl-piperidin-1-yl)-propyl]-3-methyl-piperazin-2-one

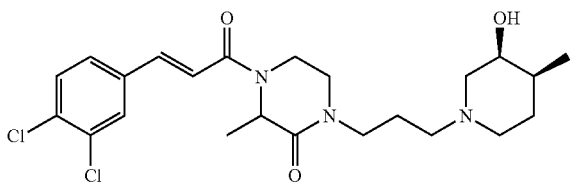

To a suspension of (3S,4S)-4-methyl-piperidin-3-ol hydrochloride (intermediate 26; 0.04 g, 0.3 mmol) in dichloromethane (1 ml) was added triethylamine (0.04 ml, 0.3 mmol) and acetic acid (0.03 ml, 0.5 mmol) followed by a solution of crude 2-methyl-3-oxo-4-(3-oxo-propyl)piperazine-1-carboxylic acid tert-butyl ester (intermediate 14c; 0.08 g, 0.3 mmol) in dichloromethane (1 ml). Sodium triacetoxyborohydride (0.07 g, 0.4 mmol) was then added and the mixture stirred for 2 h, after which time the mixture was washed with saturated aq. sodium hydrogencarbonate solution, dried (Na$_2$SO$_4$) and concentrated. The crude residue was then treated with HCl in dioxane (2 ml, 4N) and stirred for 30 minutes after which time the reaction was concentrated to afford crude 1-[3-((3S,4S)-3-hydroxy-4-methyl-piperidin-1-yl)-propyl]-3-methyl-piperazin-2-one dihydrochloride as a white powder (0.1 g). To a solution of crude 1-[3-((3S,4S)-3-hydroxy-4-methyl-piperidin-1-yl)-propyl]-3-methyl-piperazin-2-one dihydrochloride (0.03 g, 0.1 mmol) in N,N-dimethylformamide (0.8 ml) was added 3,4-dichlorocinnamic acid (0.02 g, 0.1 mmol), triethylamine (0.05 ml, 0.4 mmol) and O-(7-azabenzotriazol-1-yl)-N,N,N',N'-tetramethyluronium hexafluoro-phosphate (0.04 g, 0.1 mmol) and the reaction shaken for 1 h, after which time the reaction mixture was directly purified by preparative HPLC. This afforded the titled product as a colorless gum. MS (ISP)=468.1 (M+H)$^+$.

Example 42

4-[(E)-3-(3-Chloro-4-fluoro-phenyl)-acryloyl]-1-[3-((3S,4S)-3-hydroxy-4 methyl-piperidin-1-yl)-propyl]-3-methyl-piperazin-2-one

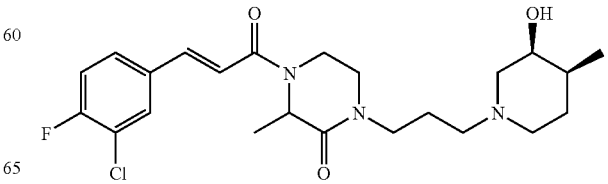

To a solution of crude 1-[3-((3S,4S)-3-hydroxy-4-methyl-piperidin-1-yl)-propyl]-3-methyl-piperazin-2-one dihydrochloride (example 41; 0.03 mg, 0.1 mmol) in N,N-dimethylformamide (0.8 ml) was added 3-chloro-4-fluorocinnamic acid (0.02 g, 0.1 mmol), triethylamine (0.05 ml, 0.4 mmol) and O-(7-azabenzotriazol-1-yl)-N,N,N',N'-tetramethyluronium hexafluoro-phosphate (0.04 g, 0.1 mmol) and the reaction shaken for 1 h, after which time the reaction mixture was directly purified by preparative HPLC. This afforded the titled product as a colorless gum. MS (ISP)=452.2 (M+H)+.

Example 43

4-[(E)-3-(3-Chloro-phenyl)-acryloyl]-1-[3-((3S,4S)-3-hydroxy-4-methyl-piperidin-1-yl)-propyl]-3-methyl-piperazin-2-one

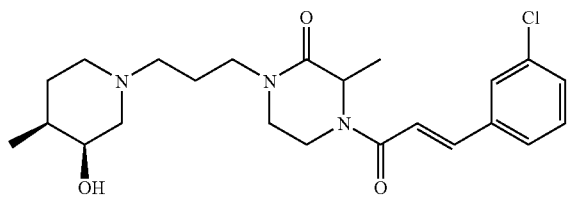

To a solution of crude 1-[3-((3S,4S)-3-hydroxy-4-methyl-piperidin-1-yl)-propyl]-3-methyl-piperazin-2-one dihydrochloride (example 41; 0.03 g, 0.1 mmol) in N,N-dimethylformamide (0.8 ml) was added 3-chloro-cinnamic acid (0.02 g, 0.1 mmol), triethylamine (0.05 ml, 0.4 mmol) and O-(7-azabenzotriazol-1-yl)-N,N,N',N'-tetramethyluronium hexafluoro-phosphate (0.04 g, 0.1 mmol) and the reaction shaken for 1 h, after which time the reaction mixture was directly purified by preparative HPLC. This afforded the titled product as a colorless gum. MS (ISP)=434.3 (M+H)+.

Example 44

4-[(E)-3-(3,4-Dichloro-phenyl)-acryloyl]-1-[3-((S)-4-hydroxy-6-aza-spiro[2.5]oct-6-yl)-propyl]-piperazin-2-one

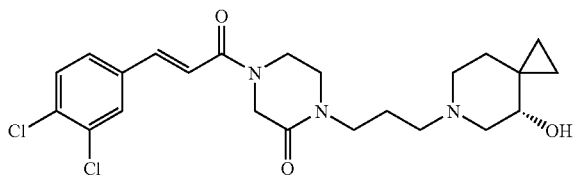

The title compound was prepared analogously to example 38 starting from crude 3-oxo-4-(3-oxo-propyl)-piperazine-1-carboxylic acid tert-butyl ester (intermediate 7b) and (S)-6-aza-spiro[2.5]octan-4-ol hydrochloride (intermediate 25). MS (ISP)=466.1 (M+H)+.

Example 45

4-[(E)-3-(3-Chloro-4-fluoro-phenyl)-acryloyl]-1-[3-((S)-4-hydroxy-6-aza-spiro[2.5]oct-6-yl)-propyl]-piperazin-2-one

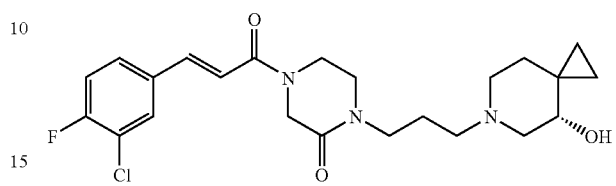

The title compound was prepared analogously to example 40 starting from crude 3-oxo-4-(3-oxo-propyl)-piperazine-1-carboxylic acid tert-butyl ester (intermediate 7b) and (S)-6-aza-spiro[2.5]octan-4-ol hydrochloride (intermediate 25). MS (ISP)=450.2 (M+H)+.

Example 46

4-[(E)-3-(3-Chloro-phenyl)-acryloyl]-1-[3-((S)-4-hydroxy-6-aza-spiro[2.5]oct-6-yl)-propyl]-piperazin-2-one

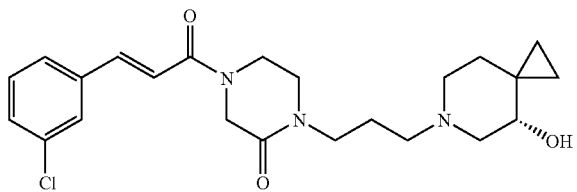

The title compound was prepared analogously to example 43 starting from crude 3-oxo-4-(3-oxo-propyl)-piperazine-1-carboxylic acid tert-butyl ester (intermediate 7b) and (S)-6-aza-spiro[2.5]octan-4-ol hydrochloride (intermediate 25). MS (ISP)=432.2 (M+H)+.

Example 47

4-[(E)-3-(3,4-Dichloro-phenyl)-acryloyl]-1-[3-((3S,5S)-3-hydroxy-5-methyl-piperidin-1-yl)-propyl]-3-methyl-piperazin-2-one

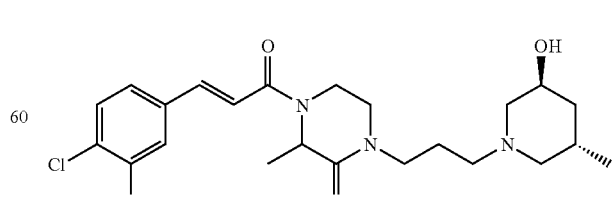

The title compound was prepared analogously to example 38 starting from crude 2-methyl-3-oxo-4-(3-oxo-propyl)- piperazine-1-carboxylic acid tert-butyl ester (intermediate 14c) and (3S,5S)-5-methyl-piperidin-3-ol hydrochloride (intermediate 27). MS (ISP)=468.1 (M+H)⁺.

Example 48

4-[(E)-3-(3,4-Dichloro-phenyl)-acryloyl]-1-[3-((3S, 5S)-3-hydroxy-5-methyl-piperidin-1-yl)-propyl]-3-methyl-piperazin-2-one

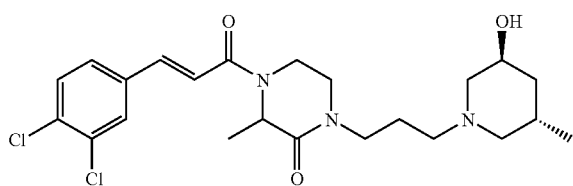

The title compound was prepared analogously to example 40 starting from crude 2-methyl-3-oxo-4-(3-oxo-propyl)-piperazine-1-carboxylic acid tert-butyl ester (intermediate 14c) and (3S,5S)-5-methyl-piperidin-3-ol hydrochloride (intermediate 27). MS (ISP)=452.2 (M+H)⁺.

Example 49

4-[(E)-3-(3-Chlorophenyl)-acryloyl]-1-[3-((3S,5S)-3-hydroxy-5-methyl-piperidin-1-yl)-propyl]-3-methyl-piperazin-2-one

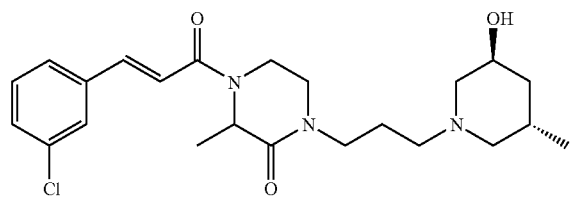

The title compound was prepared analogously to example 43 starting from crude 2-methyl-3-oxo-4-(3-oxo-propyl)-piperazine-1-carboxylic acid tert-butyl ester (intermediate 14c) and (3S,5S)-5-methyl-piperidin-3-ol hydrochloride (intermediate 27). MS (ISP)=434.2 (M+H)⁺.

Example 50

(S)-4-[(F)-3-(3-Chloro-4-fluoro-phenyl)-acryloyl]-1-[3-((S)-4-hydroxy-6-aza-spiro[2.5]oct-6-yl)-propyl]-3-methyl-piperazin-2-one

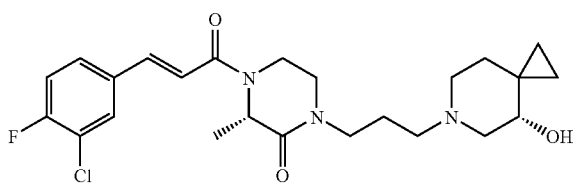

Saturated aqueous sodium hydrogencarbonate solution (15 ml) was added to a solution of (S)-4-[(E)-3-(3-chloro-4-fluoro-phenyl)-acryloyl]-1-(3-hydroxy-propyl)-3-methyl-piperazin-2-one (intermediate 28; 5.70 g, 16.1 mmol), potassium bromide (191 mg, 1.61 mmol), and 2,2,6,6-tetramethylpiperidin-1-oxyl (25 mg, 0.16 mmol). Sodium hypochlorite solution (10% in water, 9.6 ml, 16 mmol) was added portionwise at 0° C., and the course of the oxidation was monitored by thin layer chromatography. After all starting material had reacted, the reaction mixture was washed with sodium hydrogencarbonate, and the aqueous layer was extracted twice with dichloromethane. The organic phases were pooled, dried (MgSO₄), filtered, and evaporated, thus affoding 3-{(S)-4-[(E)-3-(3-chloro-4-fluoro-phenyl)-acryloyl]-3-methyl-2-oxo-piperazin-1-yl}-propionaldehyde (5.15 g). This was dissolved in dichloromethane (100 ml) and added over 20 min to a suspension of (S)-6-aza-spiro[2.5]oct-4-ol hydrochloride (intermediate 25; 2.37 g, 14.4 mmol) triethylamine (1.46 g, 14.4 mmol), acetic acid (1.74 g, 28.8 mmol) and sodium triacetoxyborohydride (90% purity; 3.78 g, 16 mmol). After 45 min the reaction mixture was partitioned between ice water and 2 M aq. sodium carbonate solution. The organic layer was dried (MgSO₄), filtered, and evaporated. Chromatography (SiO₂; dichloromethane/methanol/ammonium hydroxide 90:10:0.25) produced the title compound (5.92 g, 79%). White foam, MS (ISP)=464.2 (M+H)⁺.

Example 51

(S)-4-[(E)-3-(3-Chloro-phenyl)-acryloyl]-1-[3-((S)-4-hydroxy-6-aza-spiro[2.5]oct-6-yl)-propyl]-3-methyl-piperazin-2-one

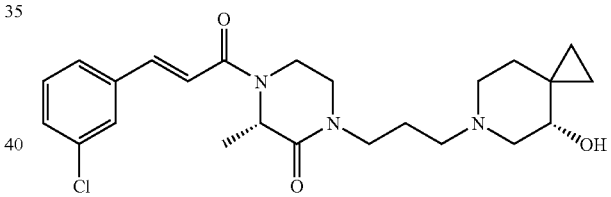

The title compound was produced in analogy to example 50 from (S)-4-[(E)-3-(3-chloro-phenyl)-acryloyl]-1-(3-hydroxy-propyl)-3-methyl-piperazin-2-one (intermediate 29) and (S)-6-aza-spiro[2.5]octan-4-ol hydrochloride (intermediate 25). White foam, MS (ISP)=446.2 (M+H)⁺.

Example 52

(R)-4-[(E)-3-(3-Chloro-4-fluoro-phenyl)-acryloyl]-1-[3-((S)-4-hydroxy-6-aza-spiro[2.5]oct-6-yl)-propyl]-3-methyl-piperazin-2-one

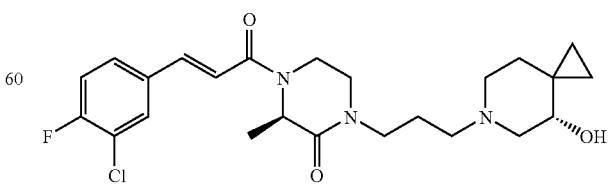

The title compound was produced in analogy to example 50 from (R)-4-[(E)-3-(3-chloro-phenyl)-acryloyl]-

1-(3-hydroxy-propyl)-3-methyl-piperazin-2-one (intermediate 30) and (S)-6-aza-spiro[2.5]octan-4-ol hydrochloride (intermediate 25). White foam, MS (ISP)=464.2 (M+H)+.

Example 53

2-[1-[(E)-3-(3,4-Dichloro-phenyl)-acryloyl]-3-oxo-4-(3-piperidin-1-yl-propyl)-piperazin-2-yl]-N,N-dimethyl-acetamide

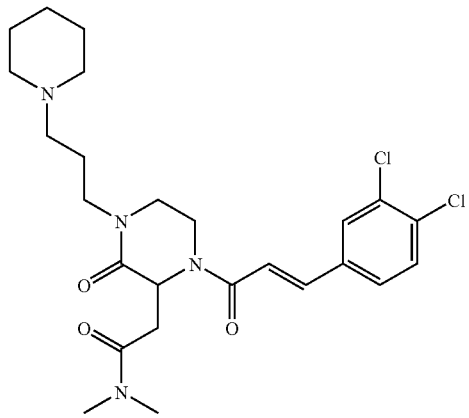

Potassium hydroxide solution (2 M in water, 90 μL, 0.18 mmol) was added to a solution of [1-[(E)-3-(3,4-dichlorophenyl)-acryloyl]-3-oxo-4-(3-piperidin-1-yl-propyl)-piperazin-2-yl]-acetic acid ethyl ester (example 33; 92 mg, 0.18 mmol) in ethanol (1 ml). The reaction mixture was stirred at room temperature for 18 h, then after evaporation potassium [1-[(E)-3-(3,4-dichloro-phenyl)-acryloyl]-3-oxo-4-(3-piperidin-1-yl-propyl)-piperazin-2-yl]-acetate was obtained. This was dissolved in N,N-dimethylformamide (1 ml), then dimethylamine hydrochloride (14 mg, 0.17 mmol), 4-methylmorpholine (81 mg, 0.99 mmol), and O-(7-azabenzotriazol-1-yl)-N,N,N',N'-tetramethyluronium hexafluoro-phosphate (92 mg, 0.24 mmol) were added. The reaction mixture was stirred for 16 h at room temperature, then partitioned between ethyl acetate and water. The organic layer was dried (MgSO4), filtered, and evaporated. Chromatography (SiO2; dichloromethane/methanol/ammonium hydroxide 90:10:0.25) afforded the title compound (73 mg, 79%). Off-white foam, MS (ISP)=509.1 (M+H)+.

Example 54

3-Aminomethyl-4-[(E)-3-(3,4-dichloro-phenyl)-acryloyl]-1-(3-piperidin-1-yl-propyl)-piperazin-2-one

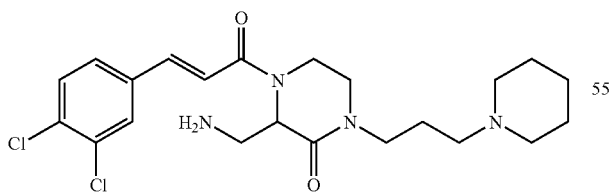

Potassium hydroxide solution (2 M in water, 80 μL, 0.16 mmol) was added to a solution of [1-[(E)-3-(3,4-dichlorophenyl)-acryloyl]-3-oxo-4-(3-piperidin-1-yl-propyl)-piperazin-2-yl]-acetic acid ethyl ester (example 33; 83 mg, 0.16 mmol) in ethanol (1 ml). The reaction mixture was stirred at room temperature for 18 h, then after evaporation potassium [1-[(E)-3-(3,4-dichloro-phenyl)-acryloyl]-3-oxo-4-(3-piperidin-1-yl-propyl)-piperazin-2-yl]-acetate was obtained. This was dissolved in 1,4-dioxane (2 ml), then triethylamine (16 mg, 0.16 mmol) and diphenylphosphoryl azide (47 mg, 0.17 mmol) were added. The reaction mixture was heated to 80° C., whereupon gas evolution was observed. After gas evolution had ceased the reaction mixture was cooled to room temperature and treated with 2 M aq. potassium hydroxide solution (2 ml), then after 1 h concentrated under vacuum. Residual water was azeotroped with toluene. Chromatography (SiO2; dichloromethane/methanol/ammonium hydroxide 90:10:0.25) afforded the title compound (13 mg, 16%). White solid, MS (ISP)=453.2 (M+H)+.

Example 55

(R)-4-[(E)-3-(3,4-Dichloro-phenyl)-acryloyl]-3-methyl-1-(3-piperidin-1-yl-propyl)-piperazin-2-one

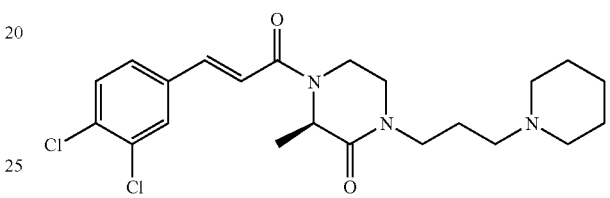

The title compound was produced in analogy to example 8 from (R)-2-methyl-3-oxy-4-(3-piperidin-1-yl-propyl)-piperazine-1-carboxylic acid tert-butyl ester (intermediate 31) and 3,4-dichlorocinnamic acid. Light yellow gum, MS (ISP)=438.3 (M+H)+.

Example 56

(S)-4-[(E)-3-(3,4-Dichloro-phenyl)-acryloyl]-3-methyl-1-(3-piperidin-1-yl-propyl)-piperazin-2-one

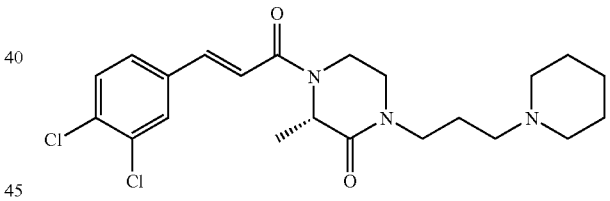

The title compound was produced in analogy to example 8 from (S)-2-methyl-3-oxo-4-(3-piperidin-1-yl-propyl)-piperazine-1-carboxylic acid tert-butyl ester (intermediate 32) and 3,4-dichlorocinnamic acid. Light yellow gum, MS (ISP)=438.3 (M+H)+.

Example 57

(R)-4-[(E)-3-(3,4-Dichloro-phenyl)-acryloyl]-3-hydroxymethyl-1-(3-piperidin-1-yl-propyl)-piperazin-2-one

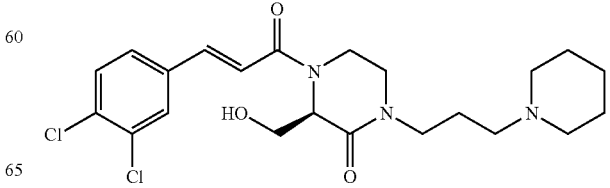

The title compound was produced in analogy to example 8 from (R)-2-hydroxymethyl-3-oxo-4-(3-piperidin-1-yl-propyl)-piperazine-1-carboxylic acid tert-butyl ester (intermediate 33) and 3,4-dichlorocinnamic acid. Colorless gum, MS (ISP)=454.2 (M+H)⁺.

Example 58

(S)-4-[(E)-3-(3,4-Dichloro-phenyl)-acryloyl]-3-hydroxymethyl-1-(3-piperidin-1-yl-propyl)-piperazin-2-one

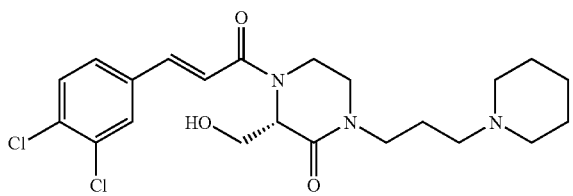

The title compound was produced in analogy to example 8 from (S)-2-hydroxymethyl-3-oxo-4-(3-piperidin-1-yl-propyl)-piperazine-1 carboxylic acid tert-butyl ester (intermediate 34) and 3,4-dichlorocinnamic acid. Off-white foam, MS (ISP)=454.2 (M+H)⁺.

Example 59

4-[(E)-3-(3,4-Dichloro-phenyl)-acryloyl]-7-(3-piperidin-1-yl-propyl)-4,7-diaza-spiro[2.5]octan-8-one

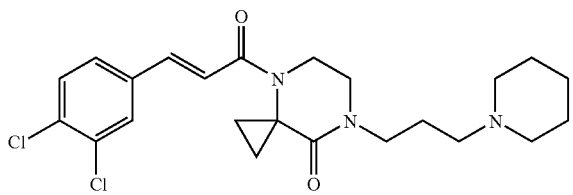

The title compound was produced in analogy to example 8 from 8-oxo-7-(3-piperidin-1-yl-propyl)-4,7-diaza-spiro[2.5]octane-4-carboxylic acid tert-butyl ester (intermediate 35) and 3,4-dichlorocinnamic acid. Light brown gum, MS (ISP)=450.1 (M+H)⁺.

Example A

Film coated tablets containing the following ingredients can be manufactured in a conventional manner:

| Ingredients | Per tablet | |
|---|---|---|
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Polyvinylpyrrolidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titanium dioxide | 0.8 mg | 1.6 mg |

The active ingredient is sieved and mixed with microcrystalline cellulose and the mixture is granulated with a solution of polyvinylpyrrolidone in water. The granulate is mixed with sodium starch glycolate and magesiumstearate and compressed to yield kernels of 120 or 350 mg respectively. The kernels are lacquered with an aqueous solution/suspension of the above mentioned film coat.

Example B

Capsules containing the following ingredients can be manufactured in a conventional manner:

| Ingredients | Per capsule |
|---|---|
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example C

Injection solutions can have the following composition:

| | |
|---|---|
| Compound of formula (I) | 3.0 mg |
| Polyethylene glycol 400 | 150.0 mg |
| Acetic acid | q.s. ad pH 5.0 |
| Water for injection solutions | Ad 1.0 ml |

The active ingredient is dissolved in a mixture of polyethylene glycol 400 and water for injection (part). The pH is adjusted to 5.0 by acetic acid. The volume is adjusted to 1.0 ml by addition of the residual amount of water. The solution is filtered, filled into vials using an appropriate overage and sterilized.

Example D

Soft gelatin capsules containing the following ingredients can be manufactured in a conventional manner:

| Capsule contents | |
|---|---|
| Compound of formula (I) | 5.0 mg |
| Yellow wax | 8.0 mg |

| | |
|---|---|
| Hydrogenated soya bean oil | 8.0 mg |
| Partially hydrogenated plant oils | 34.0 mg |
| Soya bean oil | 110.0 mg |
| Weight of capsule contents | 165.0 mg |
| Gelatin capsule | |
| Gelatin | 75.0 mg |
| Glycerol 85% | 32.0 mg |
| Karion 83 | 8.0 mg (dry matter) |
| Titanium dioxide | 0.4 mg |
| Iron oxide yellow | 1.1 mg |

The active ingredient is dissolved in a warm melting of the other ingredients and the mixture is filled into soft gelatin capsules of appropriate size. The filled soft gelatin capsules are treated according to the usual procedures.

Example E

Sachets containing the following ingredients can be manufactured in a conventional manner:

| | |
|---|---|
| Compound of formula (I) | 50.0 mg |
| Lactose, fine powder | 1015.0 mg |
| Microcrystalline cellulose (AVICEL PH 102) | 1400.0 mg |
| Sodium carboxymethyl cellulose | 14.0 mg |
| Polyvinylpyrrolidone K 30 | 10.0 mg |
| Magnesiumstearate | 10.0 mg |
| Flavoring additives | 1.0 mg |

The active ingredient is mixed with lactose, microcrystalline cellulose and sodium carboxymethyl cellulose and granulated with a mixture of polyvinylpyrrolidone in water. The granulate is mixed with magnesiumstearate and the flavouring additives and filled into sachets.

What is claimed:
1. A Compound of formula (I)

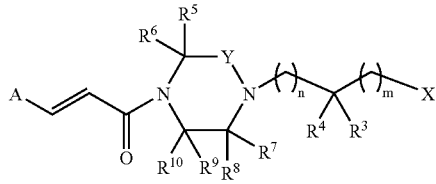

(I)

wherein
A is phenyl or naphthyl, said phenyl and said naphthyl being optionally substituted by one to three halogens;
X is —N($R^1$)($R^2$) and $R^1$ and $R^2$, together with the nitrogen atom to which they are attached, form a heterocyclyl wherein the heterocyclyl formed by $R^1$ and $R^2$, together with the nitrogen atom to which they are attached, is piperidyl or pyrrolidinyl, and said piperidyl and pyrrolidinyl being optionally substituted by one or two substituents independently selected from the group consisting of hydroxy, $C_{1-6}$ alkyl and hydroxy $C_{1-6}$ alkyl, and/or
one of the ring carbon atoms of said piperidyl and pyrrolidinyl formed by $R^1$ and $R^2$ may be shared by $C_{3-7}$ cycloalkyl ring;
Y is C(O) or S(O)$_2$;

$R^5$ and $R^6$ are independently hydrogen, $C_{1-6}$ alkyl or $C_{3-7}$ cycloalkyl, said $C_{1-6}$ alkyl and said $C_{3-7}$ cycloalkyl being optionally substituted by one to three substituents independently selected from the group consisting of amino, hydroxy, carboxyl, carbamoyl, mono or di-$C_{1-6}$ alkyl substituted carbamoyl and $C_{1-6}$ alkoxycarbonyl;
$R^7$, $R^8$, $R^9$ and $R^{10}$ are independently hydrogen, $C_{1-6}$ alkyl or $C_{3-7}$ cycloalkyl;
n is an integer of 0 to 3;
m is an integer of 0 to 3;
m+n is an integer of 1 to 5;
or a pharmaceutically acceptable salt thereof.

2. The compound of claim 1, wherein A is phenyl substituted by one or two halogen atoms independently selected from the group consisting of chlorine and fluorine.

3. The compound of claim 2, wherein A is phenyl substituted by two halogen atoms independently selected from the group consisting of chlorine and fluorine, at 3 and 4 positions of the phenyl group.

4. The compound of claim 3, wherein A is phenyl substituted by two chlorine atoms or one chlorine atom and one fluorine atom at 3 and 4 positions of the phenyl group.

5. The compound of claim 1, wherein the heterocyclyl formed by $R^1$ and $R^2$, together with the nitrogen atom to which they are attached, is piperidyl or pyrrolidinyl, and said piperidyl and pyrrolidinyl being optionally substituted by hydroxy or hydroxymethyl, and
one of the ring carbon atoms of said piperidyl and pyrrolidinyl formed by $R^1$ and $R^2$ may be shared by a cyclopropane ring.

6. The compound of claim 5, wherein X is (S)-2-hydroxymethyl-pyrrolidin-1-yl or piperidin-1-yl.

7. The compound of claim 6, wherein m+n is an integer of 1, 2 or 3.

8. The compound of claim 7, wherein m+n is 2.

9. The compound of claim 8, wherein one of $R^3$ and $R^4$ is hydrogen, and the other is hydrogen or hydroxy.

10. The compound of claim 9, wherein both $R^3$ and $R^4$ are hydrogen.

11. The compound of claim 10, wherein one or two of $R^5$, $R^6$, $R^7$, $R^8$, $R^9$ and $R^{10}$ are $C_{1-6}$ alkyl and the others are hydrogen.

12. The compound of claim 11, wherein one of $R^5$ and $R^6$ is hydrogen or $C_{1-6}$ alkyl, the other is hydrogen, and $R^7$, $R^8$, $R^9$ and $R^{10}$ are hydrogen.

13. The compound of claim 12 wherein one of $R^5$ and $R^6$ is methyl, the other is hydrogen, and $R^7$, $R^8$, $R^9$ and $R^{10}$ are hydrogen.

14. The compound of claim 13, wherein Y is C(O).

15. The compound of claim 13, wherein Y is S(O)$_2$.

16. A compound claim 1 selected from the group consisting of
4-[(E)-3-(3,4-Dichloro-phenyl)-acryloyl]-1-[3-((S)-2-hydroxymethyl-pyrrolidin-1-yl)-propyl]-piperazin-2-one,
4-[(E)-3-(3,4-Dichloro-phenyl)-acryloyl]-1-[3((S)-2-hydroxymethyl-pyrrolidin-1-yl)-propyl]-3-methyl-piperazin-2-one,
(E)-3-(3,4-Dichloro-phenyl)-1-[1,1-dioxo-2-(3-piperidin-1-yl-propyl)-1-l-6-[1,2,5]thiadiazinan-5-yl]-propenone,
4-[(E)-3-(3,4-Dichloro-phenyl)-acryloyl]-1-[3-((S)-4-hydroxy-6-aza-spiro[2.5]oct-6-yl)-propyl]-3-methyl-piperazin-2-one,
4-[(E)-3-(3-Chloro-4-fluoro-phenyl)-acryloyl]-1-[3-((S)-4-hydroxy-6-aza-spiro[2.5]oct-6-yl)-propyl]-3-methyl-piperazin-2-one, (S)-4-[(E)-3-(3-Chloro-4-fluoro-phenyl)-acryloyl]-1-[3-((S)-4-hydroxy-6-aza-spiro[2.5]oct-6-yl)-propyl]-3-methyl-piperazin-2-one, (S)-4-[(E)-3-(3-Chloro-phenyl)-acryloyl]-1-[3-((S)-4-hydroxy-6-aza-spiro[2.5]oct-6-yl)-propyl]-3-methyl-piperazin-2-one and (S)-4-[(E)-3-(3,4-Dichloro-phenyl)-acryloyl]-3-methyl-1-(3-piperidin-1-yl-propyl)-piperazin-2-one.

17. A pharmaceutical composition comprising a compound of the formula

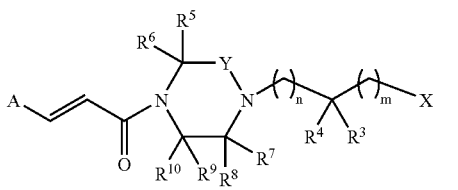

(I)

wherein

A is phenyl or naphthyl, said phenyl and said naphthyl being optionally substituted by one to three halogens;

X is —N(R$^1$)(R$^2$) and R$^1$ and R$^2$, together with the nitrogen atom to which they are attached, form a heterocyclyl wherein the heterocyclyl formed by R$^1$ and R$^2$, together with the nitrogen atom to which they are attached, is piperidyl or pyrrolidinyl, and said piperidyl and pyrrolidinyl being optionally substituted by one or two substituents independently selected from the group consisting of hydroxy, $C_{1-6}$ alkyl and hydroxy $C_{1-6}$ alkyl, and/or one of the ring carbon atoms of said piperidyl and pyrrolidinyl formed by R$^1$ and R$^2$ may be shared by $C_{3-7}$ cycloalkyl ring;

R$^3$ and R$^4$ are, independently hydrogen, hydroxy, $C_{1-6}$ alkyl, $C_{1-6}$ alkoxy, $C_{3-7}$ cycloalkyl, $C_{3-7}$ cycloalkyl $C_{1-6}$ alkyl, $C_{1-6}$ alkoxycarbonyl, carboxyl, carbamoyl, mono or di-$C_{1-6}$ alkyl substituted carbamoyl, $C_{1-6}$ alkoxycarbonyloxy, mono or di-$C_{1-6}$ alkyl substituted aminocarbonyloxy, hydroxy-$C_{1-6}$ alkyl, $C_{1-6}$ alkoxy-$C_{1-6}$ alkyl, halogen or halo $C_{1-6}$ alkyl; or R$^3$ and R$^4$, together with the carbon atom to which they are attached, form $C_{3-7}$ cycloalkyl or heterocyclyl optionally substituted by one to three substituents independently selected from the group consisting of $C_{1-4}$ alkyl, halo $C_{1-4}$ alkyl and halogen;

Y is C(O) or S(O)$_2$;

R$^5$ and R$^6$ are independently hydrogen, $C_{1-6}$ alkyl or $C_{3-7}$ cycloalkyl, said $C_{1-6}$ alkyl and said $C_{3-7}$ cycloalkyl being optionally substituted by one to three substituents independently selected from the group consisting of amino, hydroxy, carboxyl, carbamoyl, mono or di-$C_{1-6}$ alkyl substituted carbamoyl and $C_{1-6}$ alkoxycarbonyl;

R$^7$, R$^8$, R$^9$ and R$^{10}$ are independently hydrogen, $C_{1-6}$ alkyl or $C_{3-7}$ cycloalkyl;

n is an integer of 0 to 3;

m is an integer of 0 to 3;

m+n is an integer of 1 to 5;

or a pharmaceutically acceptable salt thereof and a pharmaceutically acceptable excipient.

* * * * *